(12) United States Patent
Strobel et al.

(10) Patent No.: US 7,179,839 B2
(45) Date of Patent: Feb. 20, 2007

(54) ACYLATED INDANYL AMINES AND THEIR USE AS PHARMACEUTICALS

(75) Inventors: Hartmut Strobel, Liederbach (DE); Paulus Wohlfart, Bensheim (DE); Alena Safarova, Tucson, AZ (US); Armin Walser, Tucson, AZ (US); Teri Suzuki, Tucson, AZ (US); Karl Schönafinger, Alzenau (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/073,160

(22) Filed: Feb. 13, 2002

(65) Prior Publication Data

US 2003/0055093 A1   Mar. 20, 2003

(30) Foreign Application Priority Data

Feb. 13, 2001   (EP) .................................. 01102850

(51) Int. Cl.
  *A61K 31/357*   (2006.01)
  *C07D 317/46*   (2006.01)
(52) U.S. Cl. ..................................... 514/465; 549/436
(58) Field of Classification Search ................ 549/436; 514/465
  See application file for complete search history.

(56) References Cited

U.S. PATENT DOCUMENTS

| | | | |
|---|---|---|---|
| 3,565,897 | A | 2/1971 | Heerdt et al. |
| 4,192,888 | A | 3/1980 | Bondinell et al. |
| 4,474,692 | A | 10/1984 | Oka et al. |
| 5,583,221 | A | 12/1996 | Hu et al. |
| 6,617,359 | B2 | 9/2003 | Wohlfart et al. |
| 6,759,412 | B2 | 7/2004 | Strobel |
| 6,812,253 | B2 | 11/2004 | Wohlfart et al. |
| 6,949,556 | B2 | 9/2005 | Strobel et al. |
| 2004/0082628 | A1 | 4/2004 | Strobel |
| 2004/0092513 | A1 | 5/2004 | Strobel |
| 2004/0110808 | A1 | 6/2004 | Strobel |
| 2004/0225013 | A1 | 11/2004 | Strobel |
| 2005/0054729 | A1 | 3/2005 | Strobel |
| 2005/0101599 | A1 | 5/2005 | Zeiher |

FOREIGN PATENT DOCUMENTS

| | | |
|---|---|---|
| EP | 0399422 | 11/1990 |
| JP | 9071534 | 3/1997 |
| JP | 9255592 | 9/1997 |
| WO | WO 91/17162 | 11/1991 |
| WO | WO 95/30640 | 11/1995 |
| WO | WO 96/24588 | 8/1996 |
| WO | WO 97/06158 | 2/1997 |
| WO | WO 99/26927 | 6/1999 |
| WO | WO 99/47153 | 9/1999 |
| WO | WO 00/03746 | 1/2000 |
| WO | WO 00/51970 | 8/2000 |
| WO | WO 02/20530 | 3/2002 |
| ZA | 6806875 | 3/1969 |

OTHER PUBLICATIONS

Robert S. Atkinson et al., Ring-opening of Chiral N-(3,4-dihydro-4-oxoquinazolin-3-yl)-substituted azirdines (Q*-substituted aziridines): access to Q*-free chirons, Tetrahedron Letters 39 (1998) 497-500.

Joseph G. Cannon et al., Centrally Acting Emetics. 6. Derivatives of β-Naphthylamine and 2-Indanamine, Journal of Medicinal Chemistry, 1972, vol. 15, No. 4, 348-350.

(Continued)

*Primary Examiner*—Kamal A. Saeed
(74) *Attorney, Agent, or Firm*—Ronald G. Ort

(57) ABSTRACT

The present invention relates to acylated indanyl amines according to the general formula (I)

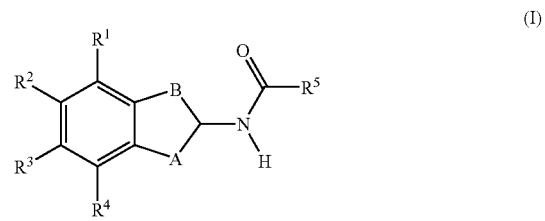

(I)

wherein $R^1$–$R^4$ have the meanings given in the description, A is $CH_2$, CHOH or CH—($C_1$–$C_3$-alkyl), B is $CH_2$ or CH—($C_1$–$C_3$-alkyl), and $R^5$ is an aryl or heteroaryl group, possibly substituted by the substituents listed in the description. These compounds are useful in the upregulation of endothelial nitric oxide synthase (eNOS), and may therefore be useful for the manufacture of medicaments for the treatment of cardiovascular diseases, stable or unstable angina pectoris, coronary heart disease, Prinzmetal angina, acute coronary syndrome, heart failure, myocardial infarction, stroke, thrombosis, peripheral artery occlusive disease, endothelial dysfunction, atherosclerosis, restenosis, endothelial damage after PTCA, hypertension, essential hypertension, pulmonary hypertension, secondary hypertension, renovascular hypertension, chronic glomerulonephritis, erectile dysfunction, ventricular arrhythmia, diabetes or diabetes complications, nephropathy or retinopathy, angiogenesis, asthma bronchiale, chronic renal failure, cirrhosis of the liver, osteoporosis, restricted memory performance, a restricted ability to learn, or for the lowering of cardiovascular risk of postmenopausal women or after intake of contraceptives.

34 Claims, No Drawings

OTHER PUBLICATIONS

Joseph G. Cannon et al., Conformationally Restricted Congeners of Dopamine Derived from 2-Aminoindan, Journal of Medicinal Chemistry, 1982, 25, 1442-1446.

Peter A. Crooks, A new synthesis of 2-aminoindanes, Chemistry and Industry, Jun. 15, 1974, 495.

E. Dornhege, Absolute Konfiguration der isomeren 2-Amino-indanole-(1) und 2-N-Isoindolinyl-indanole-(1), Liebigs Ann. Chem., 743, 42-49 (1971).

Endres et al., Stroke protection by 3-hydroxy-3-methylglutaryl (HMG)-CoA reductase inhibitors mediated by endothelial nitric oxide synthase, Proc. Natl. Acad. Sci. USA, Jul. 1998, vol. 95, pp. 8880-8885.

Hong Hu et al., Synthesis and Protein Kinase C Inhibitory Activities of Indane Analogs of Balanol, Bioorganic & Medicinal Chemistry Letters, 1996, vol. 6, No. 8, pp. 973-978.

Charles F. Huebner et al., The Azodiformate Adduct of Indene and the Stereochemistry of Some 1,2-Disubstituted Indans, The Journal of Organic Chemistry, Apr. 1970, vol. 35, No. 4, 1149-1154.

Huige Li et al., Activation of Protein Kinase Cα and/or ε Enhances Transcription of the Human Endothelial Nitric Oxide Synthase Gene, Molecular Pharmacology (1998), 53:630-637.

Béatrice Malapel-Andrieu et al., Palladium-Catalyzed Reactions of Indolic Triflate with Allylic Alcohols, Tetrahedron Letters 39 (1998) 39-42.

Moriyasu Masui et al., Stereoselective Synthesis of 1,2-Amino Alcohols by Asymmetric Borane Reduction of α-Oxoketoxime Ethers, Tetrahedron Letters 39 (1998) 5195-5198.

M. Colette et al., Étude Des Nitrosochlorures De L'Indéne Et De Ses Homologues, Ann. Chim. 1976, 269-276.

Masao Moroi et al., Interaction of Genetic Deficiency of Endothelial Nitric Oxide, Gender, and Pregnancy in Vascular Response to Injury in Mice, The Journal of Clinical Investigation, vol. 101, No. 6, Mar. 1998, 1225-1232.

Masafumi Nakayama et al., $T^{786} \rightarrow C$ Mutation in the 5'-Flanking Region of the Endothelial Nitric Oxide Synthase Gene Is Associated With Coronary Spasm, Clinical Investigation and Reports, 2864-2870 (1999).

E. Schmitz et al., Epimination of Olefins by Means of 3,3-Pentamethyleneoxaziridine—A One-Step Synthesis of Azirdines, Khimiya Geterotsiklicheskikh Soedinenni, Dec. 1974, No. 12, pp. 1629-1638.

William C. Sessa et al., Chronic Exercise in Dogs Increases Coronary Vascular Nitric Oxide Production and Endothelial Cell Nitric Oxide Synthase Gene Expression, Circulation Research, 1994, 74:349-353.

Olivier Varenne, et al., Percutaneous Gene Therapy Using Recombinant Adenoviruses Encoding Human Herpes Simplex Virus Thymidine Kinase, Human PAI-1, and Human NOS3 in Balloon-Injured Porcine Coronary Arteries, Human Gene Therapy 11:1329-1339 (Jun. 10, 2000).

Maurice Colette et al., 209. Etude de l'action de l'oxyde d'azote (III) sur l'indéne et ses homologues, Helvetica Chimica Acta, vol. 60, Fasc. 6 (1977) 2089-2098.

ACYLATED INDANYL AMINES AND THEIR USE AS PHARMACEUTICALS

The present invention relates to acylated indanyl amines of the general formula (I), with the definitions of $R^1$ to $R^5$ and A and B given below in the text, in any of their stereoisomeric forms or mixtures thereof in any ratio and/or pharmaceutically acceptable salts thereof, and their use as pharmaceutical agents.

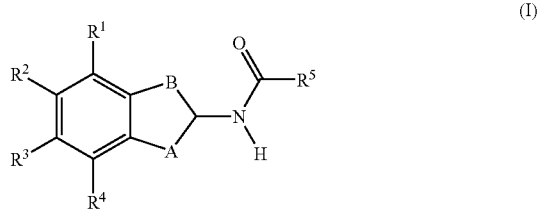

(I)

Endothelial NO synthase (eNOS, NOS-III) belongs to a group of three isoenzymes which produce nitric oxide (NO) by oxidation of arginine. Endothelially released NO is of central importance in a number of key cardiovascular mechanisms. It has a vasodilating effect and inhibits the aggregation of platelets, the adhesion of leukocytes to the endothelium and the proliferation of intimal smooth muscle cells.

Endothelial NO synthase is subject to physiological and pathophysiological regulation both at the transcriptional and at the post-transcriptional level. Enzyme already present in the endothelium may undergo calcium-dependent and calcium-independent activation through phosphorylation of specific amino acids, but also by direct interactions with specific proteins. Stimulators of this, usually transient, NO release are, extracellular arginine, 17β-estrogen and the mechanical stimulus exerted on the luminal surface of the endothelium by the blood flow (shear stress). The latter additionally leads to regulation of eNOS at the transcriptional level. Thus, for example, Sessa et al. (Circ. Research 74 (1994) 349–353) were able by means of exercise training and the increase in shear stress associated therewith to obtain a marked increase in ecNOS.

Whether regulation at the post-transcriptional level is relevant in vivo, is not unambiguously proved. Thus, for example, administration of a high arginine dose is followed by only a transient improvement in the endothelium-dependent vasorelaxation in patients with coronary heart disease.

On the other hand, the significance of the upregulation of the eNOS protein is scientifically accepted. Thus, there are findings which show that the protective properties of the HMG-CoA reductase inhibitor simvastatin can be attributed, besides the lipid lowering, also in part to an increase in eNOS expression in vivo (Endres et al., Proc. Natl. Acad. Sci. USA 95 (1998) 8880–8885). It is additionally known that single point mutations in the 5'-flanking region of the eNOS gene ("eNOS promoter"), and the reduction in the rate of eNOS gene transcription associated therewith, in the Japanese population is associated with an increase in the risk of coronary spasms (Nakayama et al., Circulation 99 (1999) 2864–2870).

The current assumption therefore is that the transcriptional and post-transcriptional mechanisms of eNOS regulation are seriously disturbed in a large number of disorders, especially in cardiovascular disorders. Even in very early stages of a wide variety of cardiovascular disorders it is possible for a dysfunction of this type in the endothelium lining the blood vessels to lead to a deficiency of bioactive NO, which is manifested as the disorder progresses in the form of measurable pathophysiological and morphological changes. Thus, critical steps in early atherogenesis are speeded up by a decrease in endothelial NO release, such as, for example, the oxidation of low density lipoproteins, the recruitment and deposition of monocytes in the intima of vessels, and the proliferation of intimal cells. A consequence of atherogenesis is the formation of plaques on the inside of the blood vessels, which may in turn lead, through a diminution in the shear stress, to a further decrease in endothelial NO release and a further deterioration in the pathology. Since endothelial NO is also a vasodilator, a decrease thereof frequently also leads to hypertension, which may, as an independent risk factor, cause further organ damage.

The aim of a therapeutic approach to the treatment of these disorders must accordingly be to interrupt this chain of events by increasing the endothelial NO expression. Gene transfer experiments which lead in vitro to overexpression of NO synthase in previously damaged vessels are in fact able to counteract the described processes and are thus evidence of the correctness of this approach (Varenne et al., Hum. Gene Ther. 11 (2000) 1329).

Some low molecular weight compounds which, in cell cultures, may lead to a direct effect on eNOS transcription and expression are disclosed in the literature. The statins which have already been mentioned are, however, the only substances for which it has been possible to date to show such an increase in eNOS in vivo as a side effect. In view of the known range of side effects of this class of substances, however, it is unclear how far this effect is present in a toxicologically unproblematic dose.

Liao et al. claim in WO 99/47153 and WO 00/03746 the use of rhoGTPase inhibitors and agents which influence the organization of the actin cytoskeleton for increasing eNOS in endothelial cells and for the therapy of various disorders such as, for example, strokes or pulmonary hypertension, without, however, indicating a specific way of achieving this.

Thus, there exists a strong need for compounds which upregulate eNOS-expression in endothelial cells. The object of the present invention is to provide compounds showing this ability.

This object is attained by acylated indanyl amines in any of their stereoisomeric forms or mixtures thereof in any ratio or pharmaceutically acceptable salt thereof according to the general formula (I).

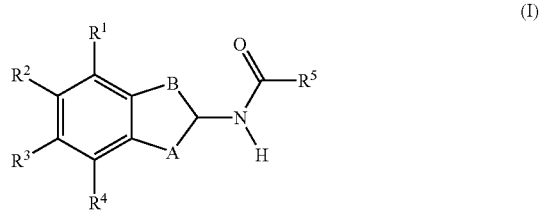

(I)

In the above formula, $R^1$ and $R^4$ are independently from each other selected from the group consisting of:

H; unsubstituted and at least monosubstituted $C_1$–$C_{10}$-alkyl, $C_2$–$C_{10}$-alkenyl and $C_2$–$C_{10}$-alkynyl, the substituents of which are selected from the group consisting of F, OH, $C_1$–$C_8$-alkoxy, ($C_1$–$C_8$-alkyl)mercapto, CN, $COOR^6$, $CONR^7R^8$, and unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$; unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$; $R^9CO$; $CONR^{10}R^{11}$; $COOR^{12}$; $CF_3$; halogens; pseudohalogens; $NR^{13}R^{14}OR^{15}$; $S(O)_mR^{16}$; $SO_2NR^{17}R^{18}$; and $NO_2$;

$R^2$ and $R^3$ are independently from each other selected from the group consisting of: H; halogens; pseudohalogens; unsubstituted and at least monosubstituted $C_1$–$C_{10}$-alkyl the substituents of which are selected from the group consisting of OH, phenyl, and heteroaryl; OH; $C_1$–$C_{10}$-alkoxy; phenoxy; $S(O)_mR^{19}$; $CF_3$; CN; $NO_2$; ($C_1$–$C_{10}$-alkyl)amino; di($C_1$–$C_{10}$-alkyl)amino ($C_1$–$C_6$-alkyl)-CONH—; unsubstituted and at least monosubstituted phenyl-CONH— and phenyl-$SO_2$—O—, the substituents of which are selected from the group consisting of halogens, pseudohalogens, $CH_3$ and methoxy; ($C_1$–$C_6$-alkyl)$SO_2$—O—; unsubstituted and at least monosubstituted ($C_1$–$C_6$-alkyl)CO, the substituents of which are selected from the group consisting of F, di($C_1$–$C_3$-alkyl)amino, pyrrolidinyl and piperidinyl; and phenyl-CO, the phenyl part of which can be substituted by one or more substituents from the group consisting of $C_1$–$C_3$-alkyl, halogens and methoxy;

A is selected from the group consisting of $CH_2$, CHOH and CH—($C_1$–$C_3$-alkyl);

B is selected from the group consisting of $CH_2$ and CH—($C_1$–$C_3$-alkyl);

$R^5$ is a group Ar or a group Hetar both of which can be unsubstituted or carry one or more substituents selected from the group consisting of: halogens; pseudohalogens; $NH_2$; unsubstituted and at least monosubstituted $C_1$–$C_{10}$-alkyl, $C_2$–$C_{10}$-alkenyl, $C_2$–$C_{10}$-alkynyl, $C_1$–$C_{10}$-alkoxy, ($C_1$–$C_{10}$-alkyl)amino, di($C_1$–$C_{10}$-alkyl)amino, the substituents of which are selected from the group consisting of F, OH, $C_1$–$C_8$-alkoxy, aryloxy, ($C_1$–$C_8$-alkyl)mercapto, $NH_2$, ($C_1$–$C_8$-alkyl)amino, and di($C_1$–$C_8$-alkyl)amino; $C_3$–$C_5$-alkandiyl; phenyl; heteroaryl; aryl- or heteroaryl-substituted $C_1$–$C_4$-alkyl; $CF_3$; $NO_2$; OH; phenoxy; benzyloxy; ($C_1$–$C_{10}$-alkyl)COO; $S(O)_mR^{20}$; SH; phenylamino; benzylamino; ($C_1$–$C_{10}$-alkyl)-CONH—; ($C_1$–$C_{10}$-alkyl)-CON($C_1$–$C_4$-alkyl)-; phenyl-CONH—; phenyl-CON($C_1$–$C_4$-alkyl)-; heteroaryl-CONH—; heteroaryl-CON($C_1$–$C_4$-alkyl)-; ($C_1$–$C_{10}$-alkyl)-CO; phenyl-CO; heteroaryl-CO; $CF_3$—CO; —$OCH_2O$—; —$OCF_2O$—; —$OCH_2CH_2O$—; —$CH_2CH_2O$—; $COOR^{21}$; $CONR^{22}R^{23}$; $CNH(NH_2)$; $SO_2NR^{24}R^{25}$; $R^{26}SO_2NH$—; $R^{27}SO_2N(C_1$–$C_6$-alkyl)-; and saturated or at least monounsaturated aliphatic, mononuclear 5- to 7-membered heterocycles containing 1 to 3 heteroatoms selected from the group consisting of N, O and S, which heterocycles can be substituted by one or more substituents selected from the group consisting of halogens, $C_1$–$C_3$-alkyl, $C_1$–$C_3$-alkoxy, OH, oxo and $CF_3$, where said heterocycles can optionally be condensed to the said group Ar or the said group Hetar; wherein all aryl, heteroaryl, phenyl, aryl-containing, heteroaryl-containing and phenyl-containing groups, which are optionally present in the said substituents of the said group Ar or the said group Hetar, can be substituted by one or more substituents selected from the group consisting of halogens, pseudohalogens, $C_1$–$C_3$-alkyl, OH, $C_1$–$C_3$-alkoxy, and $CF_3$;

$R^6$ is selected from the group consisting of: H; $C_1$–$C_{10}$-alkyl, which can be substituted by one or more substituents selected from the group consisting of F, $C_1$–$C_8$-alkoxy, and di($C_1$–$C_8$-alkyl)amino; aryl-($C_1$–$C_4$-alkyl) and heteroaryl-($C_1$–$C_4$-alkyl), which can be substituted by one or more substituents selected from the group consisting of halogens, $C_1$–$C_4$-alkoxy, and di($C_1$–$C_6$-alkyl)amino;

$R^7$ is selected from the group consisting of: H; $C_1$–$C_{10}$-alkyl which can be substituted by one or more substituents selected from the group consisting of F, $C_1$–$C_8$-alkoxy, di($C_1$–$C_8$-alkyl)amino and phenyl; phenyl; indanyl; and heteroaryl; and wherein each of the aforementioned aromatic groups can be unsubstituted or carry one or more substituents from the group consisting of halogens, pseudohalogens, $C_1$–$C_3$-alkyl, $C_1$–$C_3$-alkoxy and $CF_3$;

$R^8$ is H or $C_1$–$C_{10}$-alkyl;

$R^9$ is selected from the group consisting of: $C_1$–$C_{10}$-alkyl which can be unsubstituted or carry one or more substituents from the group consisting of: F, ($C_1$–$C_4$)-alkoxy, di($C_1$–$C_3$-alkyl)amino; and unsubstituted and at least monosubstituted phenyl and heteroaryl, the substituents of which are selected from the group consisting of $C_1$–$C_3$-alkyl, $C_1$–$C_3$-alkoxy, halogens, pseudohalogens, and $CF_3$;

$R^{10}$ independently has the same meaning as $R^7$;
$R^{11}$ independently has the same meaning as $R^8$;
$R^{12}$ independently has the same meaning as $R^6$;
$R^{13}$ is selected from the group consisting of: H; $C_1$–$C_6$-alkyl; unsubstituted and substituted phenyl, benzyl, heteroaryl, ($C_1$–$C_6$-alkyl)-CO, phenyl-CO, and heteroaryl-CO, the substituents of which are selected from the group consisting of halogens, pseudohalogens, $C_1$–$C_3$-alkyl, $C_1$–$C_3$-alkoxy, and $CF_3$, and wherein one or more of these substituents can be present;

$R^{14}$ independently has the same meaning as $R^{13}$;
$R^{15}$ is selected from the group consisting of: H; $C_1$–$C_{10}$-alkyl; ($C_1$–$C_3$-alkoxy)-$C_1$–$C_3$-alkyl; and substituted and unsubstituted benzyl, phenyl and heteroaryl, the substituents of which are selected from the group consisting of halogens, pseudohalogens, $C_1$–$C_3$-alkyl, $C_1$–$C_3$-alkoxy, and $CF_3$, and wherein one or more of these substituents can be present;

$R^{16}$ is selected from the group consisting of: $C_1$–$C_{10}$-alkyl which can be substituted by one or more substituents selected from the group consisting of F, OH, $C_1$–$C_8$-alkoxy, aryloxy, ($C_1$–$C_8$-alkyl)mercapto, ($C_1$–$C_8$-alkyl)amino and di($C_1$–$C_8$-alkyl)amino; $CF_3$; and substituted and unsubstituted phenyl and heteroaryl, the substituents of which are selected from the group consisting of halogens, pseudohalogens, $C_1$–$C_3$-alkyl, $C_1$–$C_3$-alkoxy and $CF_3$, and wherein one or more of these substituents can be present;

$R^{17}$ independently has the same meaning as $R^7$;
$R^{18}$ independently has the same meaning as $R^8$;
$R^{19}$ independently has the same meaning as $R^{16}$;
$R^{20}$ independently has the same meaning as $R^{16}$;
$R^{21}$ independently has the same meaning as $R^6$;
$R^{22}$ independently has the same meaning as $R^7$;
$R^{23}$ independently has the same meaning as $R^8$;
$R^{24}$ independently has the same meaning as $R^7$;
$R^{26}$ independently has the same meaning as $R^8$;
$R^{27}$ independently has the same meaning as $R^{16}$;

heteroaryl is a 5 to 10-membered, aromatic, mono- or bicyclic heterocycle containing one or more heteroatoms selected from the group consisting of N, O, and S;

the group Hetar is a 5 to 10-membered, aromatic, mono- or bicyclic heterocycle containing one or more heteroatoms selected from the group consisting of N, O, and S;

aryl is phenyl, naphth-1-yl or naphth-2-yl;
the group Ar is phenyl, naphth-1-yl or naphth-2-yl;
m is 0, 1 or 2;
with the proviso that, in case $R^1$, $R^2$, $R^3$ and $R^4$ are all H, $R^5$ is not unsubstituted phenyl, unsubstituted pyridyl, phenyl monosubstituted with halogen, 5-chloro-2-ethoxyphenyl, 5-chloro-2-methoxyphenyl, 5-bromo-2-methoxyphenyl, or quinoxalin-2-yl; in case $R^5$ is phenyl, A is not CHOH, $R^1$ is not methoxy or methyl, $R^2$ is not methyl or B is not CH—CH$_3$; in case $R^2$ is NO$_2$, $R^5$ is not 3-chlorophenyl.

If, in the compounds of formula (I), groups or substituents such as, for example, aryl, heteroaryl, alkyl etc., can be present several times, they all independently from each other have the meanings indicated and can hence, in each individual case, be identical with or different from each other. One example is the di($C_1$–$C_{10}$-alkyl)amino group in which the alkyl substituents can be identical or different.

Alkyl, alkenyl and alkynyl residues can be linear or branched, acyclic or cyclic. This also applies when they are part of other groups, for example in alkoxy groups, alkoxycarbonyl groups or amino groups, or when they are substituted.

Examples for alkyl groups are methyl, ethyl, propyl, butyl, pentyl, hexyl, heptyl, octyl, nonyl, decyl, the n-isomers of these residues, isopropyl, isobutyl, isopentyl, sec-butyl, tert-butyl, neopentyl, 3,3-dimethylbutyl. The term alkyl here also expressly includes cycloalkyl residues and cycloalkyl-alkyl-residues (alkyl substituted by cycloalkyl) containing at least three carbon atoms. Examples for such cycloalkyl residues are cyclopropyl, cyclobutyl, cyclopentyl, cyclohexyl, cycloheptyl and cyclooctyl. All cycloalkyl groups can be substituted by one or more identical or different ($C_1$–$C_4$)-alkyl residues, in particular by methyl. Examples for substituted cycloalkyl residues are 4-methylcyclohexyl, 4-tert-butylcyclohexyl or 2,3-dimethylcyclopentyl. Furthermore, unless stated otherwise, the term alkyl here also includes unsubstituted alkyl residues as well as alkyl residues which are substituted by one or more, for example one, two, three or four, identical or different residues, for example aryl groups. In substituted alkyl residues, for example arylalkyl, hydroxyalkyl such as —($C_1$–$C_3$)-alkyl-OH or alkoxyalkyl such as —($C_1$–$C_3$)-alkyl-O—($C_1$–$C_4$)-alkyl, the substituents can be present in any desired position.

Examples for alkenyl and alkynyl groups are the vinyl residue, the 1-propenyl residue, the 2-propenyl residue (allyl residue), the 2-butenyl residue, the 2-methyl-2-propenyl residue, the 3-methyl-2-butenyl residue, the ethynyl residue, the 2-propynyl residue (propargyl residue), the 2-butynyl residue or the 3-butynyl residue. The term alkenyl here also expressly includes cycloalkenyl residues and cycloalkenyl-alkyl-residues (alkyl substituted by cycloalkenyl) containing at least three carbon atoms. Examples for cycloalkenyl residues are cyclopentenyl, cyclohexenyl, cycloheptenyl and cyclooctenyl. All cycloalkenyl groups can be substituted by one or more identical or different ($C_1$–$C_4$)-alkyl residues, in particular by methyl. Furthermore, unless stated otherwise, the term alkenyl and alkynyl here also includes unsubstituted alkenyl and alkynyl residues as well as alkenyl and alkynyl residues which are substituted by one or more, for example one, two, three or four, identical or different residues, for example aryl groups. In substituted alkenyl and alkynyl residues, for example arylalkenyl, hydroxyalkenyl such as —($C_2$–$C_3$)-alkenyl-OH or alkoxyalkenyl such as ($C_1$–$C_3$-alkyl)-O—($C_2$–$C_4$-alkenyl)-, the substituents can be present in any desired position.

Examples for $C_3$–$C_5$-alkandiyl are —CH$_2$CH$_2$CH$_2$—, —CH$_2$—CH(CH$_3$)—, —CH$_2$CH$_2$CH$_2$CH$_2$— and —CH$_2$CH$_2$CH$_2$CH$_2$CH$_2$— groups.

If not stated otherwise, the above-mentioned phenyl residues, naphthyl and indanyl residues and heterocyclic residues (including heteroaryl residues) can be unsubstituted or can carry one or more, for example one, two, three or four, of the substituents indicated in the above definition which can be in any desired position. If in compounds of the formula (I) nitro groups are present as substituents, in total only up to two nitro groups are preferably present in the molecule. In monosubstituted phenyl residues the substituent can be in the 2-position, the 3-position or the 4-position, in disubstituted phenyl residues the substituents can be in 2,3-position, 2,4-position, 2,5-position, 2,6-position, 3,4-position or 3,5-position. In trisubstituted phenyl residues the substituents can be in 2,3,4-position, 2,3,5-position, 2,3,6-position, 2,4,5-position, 2,4,6-position or 3,4,5-position. In fourfold substituted phenyl residues, the substituents can be in the 2,3,4,5-position, the 2,3,4,6-position, or the 2,3,5,6-position. Tolyl (=methylphenyl) can be 2-tolyl, 3-tolyl or 4-tolyl. Naphthyl can be 1-naphthyl or 2-naphthyl. In monosubstituted 1-naphthyl residues the substituent can be in the 2-position, the 3-position, the 4-position, the 5-position, the 6-position, the 7-position or the 8-position, in monosubstituted 2-naphthyl residues in the 1-position, the 3-position, the 4-position, the 5-position, the 6-position, the 7-position or the 8-position. In higher substituted naphthyl radicals, for example 1-naphthyl radicals or 2-naphthyl radicals which carry two or three substituents, the substituents can also be situated in all possible positions. Indanyl residues include indan-1-yl residues and indan-2-yl residues which can be unsubstituted or carry one or more of the substituents indicated. In case the indanyl residues are substituted, the substituent or substituents can be in any of the positions possible.

The above definitions as well as the following definitions relating to monovalent residues equally apply to the divalent residues phenylene, naphthylene and heteroarylene. Those divalent residues can be attached to the adjacent groups by any ring carbon atom. In the case of a phenylene residue, these can be in 1,2-position (ortho-phenylene), 1,3-position (meta-phenylene) or 1,4-position (para-phenylene). In the case of a naphthylene residue the free bonds can be in 1,2-position (=1,2-naphthylene or 1,2-naphthalinediyl) or in 1,3-position, 1,4-position, 1,5-position, 1,6-position, 1,7-position, 1,8-position, 2,3-position, 2,6-position or 2,7-position. In the case of 5-membered ring aromatics containing one heteroatom such as, for example, thiophene or furan, the two free bonds can be in 2,3-position, 2,4-position, 2,5-position or 3,4-position. A divalent residue derived from pyridine can be a 2,3-, 2,4-, 2,5-, 2,6-, 3,4- or 3,5-pyridinediyl residue. In the case of unsymmetrical divalent residues the present invention includes all positional isomers, i.e., in the case of a 2,3-pyridinediyl residue, for example, it includes the compound in which the one adjacent group is present in the 2-position and the other adjacent group is present in the 3-position as well as the compound in which the one adjacent group is present in the 3-position and the other adjacent group is present in the 2-position.

Unless stated otherwise, heteroaryl residues, heteroarylene residues, heterocyclyl residues and rings which are formed by two groups bonded to a nitrogen are preferably derived from heterocycles which contain one, two, three or four heteroatoms which can be identical or different; more preferably they are derived from heterocycles which contain one, two, or three, in particular one or two, heteroatoms which can be identical or different. Unless stated otherwise, the heterocycles can be monocyclic or polycyclic, for example monocyclic, bicyclic or tricyclic. Preferably they are monocyclic or bicyclic. The rings preferably are 5-membered rings, 6-membered rings or 7-membered rings. Examples of monocyclic and bicyclic heterocyclic systems from which residues occuring in the compounds of the formula (I) can be derived, are pyrrole, furan, thiophene, imidazole, pyrazole, 1,2,3-triazole, 1,2,4-triazole, 1,3-dioxole, 1,3-oxazole (=oxazole), 1,2-oxazole (=isoxazole), 1,3-thiazole (=thiazole), 1,2-thiazole (=isothiazole), tetrazole, pyridine, pyridazine, pyrimidine, pyrazine, pyran, thiopyran, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, 1,2,4,5-tetrazine, azepine, 1,2-diazepine, 1,3-diazepine, 1,4-diazepine, 1,3-oxazepine, 1,3-thiazepine, indole, benzothiophene, benzofuran, benzothiazole, benzimidazole, benzodioxol, quinoline, isoquinoline, cinnoline, quinazoline, quinoxaline, phthalazine, thienothiophenes, 1,8-naphthyridine and other naphthyridines, pteridin, or phenothiazine, each of them in saturated form (perhydro form) or in partially unsaturated form (for example in the dihydro form or the tetrahydro form) or in maximally unsaturated form, in case the respective forms are known and stable. The term "aryl" and the term "heteroaryl" as used herein comprise bicyclic residues in which both cycles are aromatic as well as bicyclic residues in which only one cycle is aromatic. Independently, the same applies to the term "group Ar" or the term "group Hetar", respectively. Suitable heterocycles include, for example, the saturated heterocycles pyrrolidine, piperidine, piperazine, morpholine and thiomorpholine. The degree of saturation of heterocyclic groups is indicated in their individual definitions. Unsaturated heterocycles can contain, for example, one, two or three double bonds within the ring system. 5-membered rings and 6-membered rings can in particular also be aromatic.

Substituents which may be derived from these heterocycles can be attached via any suitable carbon atom. Residues derived from nitrogen heterocycles can carry a hydrogen atom or a substituent on a ring nitrogen atom, and examples include pyrrole, imidazole, pyrrolidine, morpholine, piperazine residues, etc. Those nitrogen heterocyclic residues can also be attached via a ring nitrogen atom, in particular if the respective heterocyclic residue is bonded to a carbon atom. For example, a thienyl residue can be present as 2-thienyl residue or 3-thienyl residue, a furyl residue as 2-furyl residue or 3-furyl residue, a pyridyl residue as 2-pyridyl residue, 3-pyridyl residue or 4-pyridyl residue, a piperidinyl residue as 1-piperidinyl residue (=piperidino residue), 2-piperidinyl residue, 3-piperidinyl residue or 4-piperidinyl residue, a (thio)morpholinyl residue as 2-(thio)morpholinyl residue, 3-(thio)morpholinyl residue or 4-(thio)morpholinyl residue (=thiomorpholino residue). A residue derived from 1,3-thiazole or imidazole which is attached via a carbon atom can be attached via the 2-position, the 4-position or the 5-position.

In case a heterocyclic groups is substituted, it can carry one or more, for example one, two, three or four, identical or different substituents. Substituents in heterocycles can be present in any desired positions, for example in a 2-thienyl residue or 2-furyl residue in the 3-position and/or in the 4-position and/or in the 5-position, in a 3-thienyl residue or 3-furyl residue in the 2-position and/or in the 4-position and/or in the 5-position, in a 2-pyridyl residue in the 3-position and/or in the 4-position and/or in the 5-position and/or in the 6-position, in a 3-pyridyl residue in the 2-position and/or in the 4-position and/or in the 5-position and/or in the 6-position, in a 4-pyridyl residue in the 2-position and/or in the 3-position and/or in the 5-position and/or in the 6-position. Suitable nitrogen heterocycles can also be present as N-oxides or as quarternary salts containing a counterion which is derived from a pharmaceutically acceptable acid. Pyridyl residues, for example, can be present as pyridine-N-oxides.

Halogen is fluorine, chlorine, bromine or iodine, preferably fluorine or chlorine.

Examples for pseudohalogens are CN and $N_3$, a preferred pseudohalogen is CN.

The present invention includes all stereoisomeric forms of the compounds of the formula (I). Centers of asymmetry that are present in the compounds of formula (I) all independently of one another have S configuration or R configuration. The invention includes all possible enantiomers and diastereomers and mixtures of two or more stereoisomers, for example mixtures of enantiomers and/or diastereomers, in all ratios. Thus, compounds according to the present invention which can exist as enantiomers can be present in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. All these forms are an object of the present invention. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at the stage of the compounds of the formula (I) or at the stage of an intermediate during the synthesis. The present invention also includes all tautomeric forms of the compounds of formula (I).

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be present on these groups and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

The present invention furthermore includes all solvates of compounds of the formula (I), for example hydrates or adducts with alcohols, active metabolites of the compounds of the formula (II), and also derivatives and prodrugs of the compounds of the formula (I) which contain physiologically tolerable and cleavable groups, for example esters, amides and compounds in which the N—H group depicted in formula (I) is replaced with an N-alkyl group, such as N-methyl, or with an N-acyl group, such as N-acetyl or N-argininyl, including pharmaceutically acceptable salts formed on functional groups present in the N-acyl group.

Preferred compounds of the formula (I) are those compounds in which one or more of the residues contained therein have the meanings given below, with all combinations of preferred substituent definitions being a subject of the present invention. With respect to all preferred compounds of the formula (I) the present invention also includes all stereoisomeric forms and mixtures thereof in all ratios, and their pharmaceutically acceptable salts.

In preferred embodiments of the present invention, the substituents $R^1$ to $R^5$, A and B and the groups aryl and heteroaryl of the formula (I) independently from each other have the following meanings. Hence, one or more of the substituents $R^1$ to $R^5$ and A and B can have the preferred meanings, the more preferred meanings, the even more preferred meanings, the most preferred meanings, or the particularly preferred meanings given below.

$R^1$ is preferably selected from the group consisting of: H; $C_1$–$C_4$-alkyl; $C_1$–$C_4$-alkoxy; $CF_3$; halogens; pseudohalogens; $(C_1$–$C_4$-alkyl)-$S(O)_m$—; and unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$, where heteroaryl is selected from the group consisting of 5- and 6-membered heterocycles containing one or more heteroatoms selected from the group consisting of N, O, and S; $R^1$ is more preferably H, halogen or $C_1$–$C_4$-alkyl.

$R^2$ is preferably selected from the group consisting of: H; halogens; pseudohalogens; and $C_1$–$C_3$-alkyl; $R^2$ is more preferably H.

$R^3$ is preferably selected from the group consisting of: H; halogens; pseudohalogens; and $C_1$–$C_3$-alkyl; $R^3$ is more preferably H.

$R^4$ is preferably selected from the group consisting of: H; $C_1$–$C_4$-alkyl; $C_1$–$C_4$-alkoxy; $CF_3$; halogens; pseudohalogens; $(C_1$–$C_4$-alkyl)-$S(O)_m$—; and unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$, where heteroaryl is selected from the group consisting of 5- and 6- membered heterocycles containing one or more heteroatoms selected from the group consisting of N, O, and S; $R^4$ is more preferably H, halogen or $C_1$–$C_4$-alkyl; $R^4$ is most preferably H.

$R^1$ to $R^4$ are in particular each H.

A is preferably selected from the group consisting of $CH_2$ and CHOH; A is in particular $CH_2$.

B is preferably selected from the group consisting of $CH_2$ and CH—$CH_3$; B is in particular $CH_2$.

$R^5$ is preferably selected from the group consisting of: a group Ar or a group Hetar both of which can be unsubstituted or carry one or more substituents selected from the group consisting of: halogens; CN; $NH_2$; unsubstituted and at least monosubstituted $C_1$–$C_8$-alkyl, $C_2$–$C_8$-alkenyl, $C_2$–$C_8$-alkynyl, $C_1$–$C_8$-alkoxy, ($C_1$–$C_8$-alkyl)amino, di($C_1$–$C_8$-alkyl)amino, the substituents of which are selected from the group consisting of F, $C_1$–$C_6$-alkoxy, phenoxy, ($C_1$–$C_6$-alkyl)mercapto, $NH_2$, ($C_1$–$C_6$-alkyl)amino, and di($C_1$–$C_6$-alkyl)amino; $C_3$–$C_5$-alkandiyl; phenyl; heteroaryl; phenyl- or heteroaryl-substituted $C_1$–$C_2$-alkyl; $CF_3$; OH; phenoxy; benzyloxy; ($C_1$–$C_6$-alkyl)COO; $S(O)_m$($C_1$–$C_6$)-alkyl; $S(O)_m$-phenyl; $S(O)_m$-heteroaryl; SH; phenylamino; benzylamino; ($C_1$–$C_6$-alkyl)-CONH—; ($C_1$–$C_6$-alkyl)-CON($C_1$–$C_4$-alkyl)-; phenyl-CONH—; phenyl-CON($C_1$–$C_4$-alkyl)-; heteroaryl-CONH—; heteroaryl-CON($C_1$–$C_4$-alkyl)-; ($C_1$–$C_6$-alkyl)-CO; phenyl-CO; heteroaryl-CO; $CF_3$—CO; —$OCH_2O$—; —$OCF_2O$—; —$OCH_2CH_2O$—; —$CH_2CH_2O$—; COO($C_1$–$C_6$-alkyl); —$CONH_2$; —CONH($C_1$–$C_6$-alkyl); —CON(di($C_1$–$C_6$-alkyl)); $CNH(NH_2)$; —$SO_2NH_2$; —$SO_2NH(C_1$–$C_6$-alkyl); —$SO_2NH$(phenyl); —$SO_2N$(di($C_1$–$C_6$-alkyl)); ($C_1$–$C_6$-alkyl)$SO_2NH$—; ($C_1$–$C_6$-alkyl)$SO_2N(C_1$–$C_6$-alkyl)-; phenyl-$SO_2NH$—; phenyl-$SO_2N(C_1$–$C_6$-alkyl)-; heteroaryl-$SO_2NH$—; heteroaryl-$SO_2N(C_1$–$C_6$-alkyl)-; and saturated or at least monounsaturated aliphatic, mononuclear 5- to 7-membered heterocycles containing 1 to 3 heteroatoms selected from the group consisting of N, O, and S, which heterocycles can be substituted by one or more substituents selected from the group consisting of halogens, $C_1$–$C_3$-alkyl, $C_1$–$C_3$-alkoxy, OH, oxo and $CF_3$, where said heterocycles can optionally be condensed to the said group Ar or the said group Hetar; wherein all heteroaryl, phenyl, heteroaryl-containing and phenyl-containing groups, which are optionally present in the said substituents of the said group Ar or the said group Hetar, can be substituted by one or more substituents selected from the group consisting of halogens, pseudohalogens, $C_1$–$C_3$-alkyl, OH, $C_1$–$C_3$-alkoxy, and $CF_3$;

$R^5$ is more preferably selected from the group consisting of: phenyl or a group Hetar both of which can be unsubstituted or carry one or more substituents selected from the group consisting of: halogens; CN; $NH_2$; unsubstituted and at least monosubstituted $C_1$–$C_6$-alkyl, $C_2$–$C_6$-alkenyl, $C_2$–$C_6$-alkynyl, $C_1$–$C_3$-alkoxy, ($C_1$–$C_4$-alkyl)amino, di($C_1$–$C_4$-alkyl)amino, the substituents of which are selected from the group consisting of F, $C_1$–$C_3$-alkoxy, ($C_1$–$C_3$-alkyl)mercapto, and $NH_2$; $C_3$–$C_5$-alkandiyl; phenyl; heteroaryl; phenyl- or heteroaryl-substituted $C_1$–$C_2$-alkyl; $CF_3$; OH; ($C_1$–$C_4$-alkyl)COO; $S(O)_m$($C_1$–$C_4$)-alkyl; ($C_1$–$C_4$-alkyl)-CONH—; ($C_1$–$C_4$-alkyl)-CON($C_1$–$C_4$-alkyl)-; ($C_1$–$C_4$-alkyl)-CO; phenyl-CO; heteroaryl-CO; $CF_3$—CO; —$OCH_2O$—; —$OCF_2O$—; —$OCH_2CH_2O$—; —$CH_2CH_2O$—; COO($C_1$–$C_6$-alkyl); —$CONH_2$; —CONH($C_1$–$C_4$-alkyl); —CON(di($C_1$–$C_4$-alkyl)); $CNH(NH_2)$; —$SO_2NH_2$; —$SO_2NH(C_1$–$C_4$-alkyl); —$SO_2NH$(phenyl); —$SO_2N$(di($C_1$–$C_4$-alkyl)); ($C_1$–$C_4$-alkyl)$SO_2NH$—; ($C_1$–$C_4$-alkyl)$SO_2N(C_1$–$C_4$-alkyl)-; and saturated or at least monounsaturated aliphatic, mononuclear 5- to 7-membered heterocycles containing 1 to 3 heteroatoms selected from the group consisting of N, O and S, which heterocycles can be substituted by one or more substituents selected from the group consisting of halogens, $C_1$–$C_3$-alkyl, $C_1$–$C_3$-alkoxy, OH, oxo and $CF_3$, where said heterocycles can optionally be condensed to the said phenyl or the said group Hetar; wherein all heteroaryl, phenyl, heteroaryl-containing and phenyl-containing groups, which are optionally present in the said substituents of the said phenyl or the said group Hetar, can be substituted by one or more substituents selected from the group consisting of halogens, pseudohalogens, $C_1$–$C_3$-alkyl, OH, $C_1$–$C_3$-alkoxy, and $CF_3$;

$R^5$ is even more preferably selected from the group consisting of: phenyl or a group Hetar both of which can be unsubstituted or carry one or more substituents selected from the group consisting of: F; Cl; Br; $C_1$–$C_3$-alkyl; $C_1$–$C_3$-alkoxymethyl; 2-amino-3,3,3-trifluoro-propyl-; $CF_3$; $C_3$–$C_5$-alkandiyl; phenyl; heteroaryl; benzyl; heteroaryl-methyl; OH; $C_1$–$C_3$-alkoxy; phenoxy; trifluoromethoxy; 2,2,2-trifluoroethoxy; ($C_1$–$C_4$-alkyl)COO; ($C_1$–$C_3$-alkyl)mercapto; phenylmercapto; ($C_1$–$C_3$-alkyl)sulfonyl; phenylsulfonyl; $NH_2$; ($C_1$–$C_4$-alkyl)amino; di($C_1$–$C_4$-alkyl)amino; ($C_1$–$C_3$-alkyl)-CONH—; ($C_1$–$C_3$-alkyl)-$SO_2NH$—; ($C_1$–$C_3$-alkyl)-CO; phenyl-CO; —$OCH_2O$—; —$OCF_2O$—; —$CH_2CH_2O$—; COO($C_1$–$C_4$-alkyl); —$CONH_2$; —CONH($C_1$–$C_4$-alkyl); —CON(di($C_1$–$C_4$alkyl)); CN; —$SO_2NH_2$; —$SO_2NH(C_1$–$C_4$-alkyl); —$SO_2N(di(C_1$–$C_4$-alkyl)); pyrrolidinyl; piperidinyl; morpholinyl; and thiomorpholinyl; wherein all heteroaryl, phenyl, heteroaryl-containing and phenyl-containing groups, which are optionally present in the said substituents of the said phenyl or the said group Hetar, can be substituted by one or more substituents selected from the group consisting of halogens, pseudohalogens, $C_1$–$C_3$-alkyl, OH, $C_1$–$C_3$-alkoxy, and $CF_3$;

$R^5$ is most preferably selected from the group consisting of: 4-fluorophenyl, 4-chlorophenyl, 4-bromophenyl, 4-($C_1$–$C_3$-alkoxy)-phenyl, 4-trifluoromethoxyphenyl, 2-bromo-4-fluorophenyl, 2-chloro-4-fluorophenyl, 3,4-dimethylphenyl, 2,4-dimethylphenyl, 4-chloro-2-methylphenyl, 2-hydroxy-4-methylphenyl, 2-hydroxy-4-ethoxyphenyl, 2-methoxy-4-methylphenyl, 4-phenoxyphenyl, 3-fluoro-4-methylphenyl, benzo[1,3]dioxol-5-yl, 2,2-difluoro-benzo[1,3]dioxol-5-yl, 2,3-dihydrobenzofuran-5-yl, 1-(4-chlorophenyl)-5-trifluoromethyl-1H-pyrazole-4-yl, 1-(4-fluorophenyl)-3,5-dimethyl-1H-pyrazole-4-yl, 1H-benzotriazole-5-yl, 1H-indole-4-yl, 1H-indole-6-yl, 1-isopropyl-2-trifluoromethyl-1H-benzoimidazole-5-yl, 1-methyl-3-oxo-1,2,3,4-tetrahydro-quinoxaline-6-yl, 1-phenyl-5-trifluoromethyl-1H-pyrazole-4-yl, 2-(2-hydroxy-pyridin-4-yl)-1H-benzoimidazole-5-yl, 2-(4-cyano-phenyl)-1H-benzoimidazole-5-yl, 2,4-dimethyl-oxazole-5-yl, 2,4-dimethyl-pyrimidine-5-yl, 2,4-dimethyl-thiazole-5-yl, 2,5-dimethyl-1H-pyffole-3-yl, 2,5-dimethyl-1-phenyl-1H-pyrrole-3-yl, 2,5-dimethyl-1-pyridin-4-ylmethyl-1H-pyrrole-3-yl, 2,5-dimethyl-2H-pyrazole-3-yl, 2,6-dichloro-pyrid-3-yl, 2,6-dimethoxy-pyrid-3-yl, 2,6-dimethyl-pyrid-3-yl, 2-amino-4,6-dimethyl-pyrid-3-yl, 2-amino-6-chloro-pyrid-3-yl, 2-amino-pyrid-3-yl, 2-chloro-6methyl-pyrid-3-yl, 2-chloro-pyrid-4-yl, 2-cyclopropyl-4-methyl-thiazole-5-yl, 2-dimethylamino-4-methyl-thiazole-5-yl, 2-dimethylamino-pyrid-4-yl, 2-ethyl-5-methyl-2H-pyrazole-3-yl, 2-hydroxy-6-methyl-pyrid-3-yl, 2-methyl-1H-benzoimidazole-5-yl, 2-methyl-3H-benzoimidazole-5-yl, 2-methyl-pyrid-3-yl, 2-methyl-6-trifluoromethyl-pyrid-3-yl, 2-methyl-thiazole-5-yl, 2-morpholin-4-yl-pyridin-4-yl, 2-morpholin-4-yl-pyrimidine-5-yl, 2-pyrrolidin-1-yl-pyridin-4-yl, 3,5-dimethyl-1H-pyrazole-4-yl, 3-amino-5,6-dimethyl-pyrazine-2-yl, 3-amino-5-methyl-pyrazine-2-yl, 3-amino-pyrazine-2-yl, 3-dimethylamino-4-methyl-phenyl, 3-dimethylamino-phenyl, 3H-benzoimidazole-5-yl, 1H-benzoimidazole-5-yl, 3-methanesulfonylamino-2-methyl-phenyl, 3-methanesulfonylamino-phenyl, 3-methyl-isoxazole-4-yl, 3-morpholin-4-yl-phenyl, 3-piperidin-1-yl-phenyl, 3-pyrrolidin-1-yl-phenyl, 4-(2,2,2-trifluoro-ethoxy)-phenyl, 4,6-dimethyl-pyrid-3-yl, 4-amino-2-ethylsulfanyl-pyrimidine-5-yl, 4-amino-2-methyl-pyrimidine-5-yl, 4-chloro-3-methanesulfonylamino-phenyl, 4-chloro-3-sulfamoyl-phenyl, 4-methyl-3-methylamino-phenyl, 4-methyl-thiazole-5-yl, pyridine-2-yl, 5,6,7,8-tetrahydro-quinoline-3-yl, 5-amino-1-phenyl-1H-pyrazole-4-yl, 5-methanesulfonyl-2-methyl-phenyl, 5-methyl-1-phenyl-1H-pyrazole-4-yl, 5-methyl-isoxazole-3-yl, 5-methyl-pyrid-3-yl, 5-methyl-pyrazine-2-yl, 6-chloro-pyrid-3-yl, 6-cyano-pyrid-3-yl, 6-dimethylamino-pyrid-3-yl, 6-ethynyl-pyrid-3-yl, 6-methoxymethyl-pyrid-3-yl, 6-methoxy-pyrid-3-yl, 6-methyl-2-methylamino-pyrid-3-yl, 6-methylamino-pyrazine-2-yl, 6-methyl-pyrid-3-yl, 6-morpholin-4-yl-pyrid-3-yl, 6-pyrrolidin-1-yl-pyrid-3-yl, imidazo[1,2-a]pyridine-2-yl, 6-trifluoromethyl-pyrid-3-yl, pyrimidine-4-yl, 4-methylsulfanylphenyl, 4-ethylsulfanylphenyl, 3-methoxycarbonylphenyl, 4-methoxycarbonylphenyl, 3-ethoxycarbonylphenyl, 4-ethoxycarbonylphenyl, 2-bromo-4-chlorophenyl, 2,3-dichlorophenyl, 3-chloro-4-(propane-2-sulfonyl)-thiophene-2-yl, 4-bromo-2-chlorophenyl, 4-methoxyphenyl, 4-ethoxyphenyl, 3-methoxyphenyl, 3-ethoxyphenyl, 2-methyl-thiophene-3-yl, 3-chloro-4-methyl-thiophene-2-yl, 5-bromo-thiophene-2-yl, 5-chloro-thiophene-2-yl, 5-methyl-thiophene-2-yl, 4-methyl-thiophene-2-yl, 3-methyl-thiophene-2-yl, 5-acetyl-thiophene-2-yl, pyridine-3-yl, pyridine-4-yl, 4-trifluoromethyl-phenyl, 4-ethylaminophenyl, 4-methylaminophenyl, 2-aminophenyl, 4-bromo-2-fluorophenyl, 2-chloro-phenyl, 3-chloro-4-methyl-phenyl, 4-chloro-3-methyl-phenyl, 2-chloro-3-methyl-phenyl, 2-methyl-phenyl, 2-acetoxy-4-methyl-phenyl, 2-acetoxy-4-ethoxy-phenyl, 2-acetoxy-4-methoxy-phenyl, 4-trifluoromethylsulfanyl-phenyl, naphthalene-2-yl, 1,1-dimethyl-indan-4-yl, 3-isobutyrylamino-phenyl, 3-(2,2-dimethylpropionylamino)-phenyl, 2-bromophenyl, 2-fluorophenyl, 3-bromo-5-methyl-thiophene-2-yl, 3-chloro-6-fluoro-benzo[b]thiophene-2-yl and 3,4-dichloro-benzo[b]thiophene-2-yl.

Heteroaryl is preferably a 5 to 10-membered, aromatic, mono- or bicyclic heterocycle containing one, two or three heteroatoms selected from the group consisting of N, O and S; heteroaryl is most preferably selected from the group consisting of: furyl, pyrrolyl, thienyl, thiazolyl, isothiazolyl, oxazolyl, isoxazolyl, pyrazolyl, imidazolyl, pyridazinyl, pyrazinyl, pyridyl, pyrimidinyl, benzoimidazolyl, benzthiazolyl, benzoxazolyl, quinolinyl, isoquinolinyl, quinoxalinyl, quinazolyl, indolyl, benzofuranyl, benzodioxolyl, benzothiophenyl, and indazolyl.

The group Hetar is preferably a 5 to 10-membered, aromatic, mono- or bicyclic heterocycle containing one, two or three heteroatoms selected from the group consisting of N, O, and S; the group Hetar is most preferably selected from the group consisting of: faryl, pyrrolyl, thienyl, thiazolyl, isothiazolyl, oxazolyl, isoxazolyl, pyrazolyl, imidazolyl, pyridazinyl, pyrazinyl, pyridyl, pyrimidinyl, benzoimidazolyl, benzthiazolyl, benzoxazolyl, quinolinyl, isoquinolinyl, quinoxalinyl, quinazolyl, indolyl, benzofuranyl, benzodioxolyl, benzothiophenyl, and indazolyl.

Aryl is preferably phenyl.

m is preferably 0 or 2.

Compounds of the formula (I) in which some or all of the above-mentioned groups have the preferred meanings, the more preferred meanings, the even more preferred meanings, the most preferred meanings, or the particularly preferred meanings defined above are also an object of the present invention.

Most preferred compounds according to the general formula (I), in any of their stereoisomeric forms or mixtures thereof in any ratio or the pharmaceutically acceptable salts thereof, are selected from the group consisting of:

N-indan-2-yl-4-trifluoromethyl-benzamide, 5-bromo-thiophene-2-carboxylic acid indan-2-ylamide, 2-hydroxy-N-indan-2-yl-4-methyl-benzamide, 4-ethylsulfanyl-N-indan-2-yl-benzamide, 2,2-difluoro-benzo[1,3]dioxole-5-carboxylic acid indan-2-ylamide, 2,5-dimethyl-1-pyridin-4-ylmethyl-1H-pyrrole-3-carboxylic acid indan-2-ylamide, 2,3-dihydro-benzofuran-5-carboxylic acid indan-2-ylamide, 1H-indole-6-carboxylic acid indan-2-ylamide, acetic acid 2-(indan-2-ylcarbamoyl)-5-methyl-phenyl ester, 2-amino-N-indan-2-yl-benzamide, 2,5-dimethyl-1H-pyrrole-3-carboxylic acid indan-2-ylamide, 5-methyl-thiophene-2-carboxylic acid indan-2-ylamide, 3-chloro-4-methyl-thiophene-2-carboxylic acid indan-2-ylamide, 3-methyl-thiophene-2-carboxylic acid indan-2-ylamide, N-indan-2-yl-4-methylamino-benzamide, N-indan-2-yl-4-methylsulfanyl-benzamide, 3-chloro-4-(propane-2-sulfonyl)-thiophene-2-carboxylic acid indan-2-ylamide, 5-methyl-1-phenyl-1H-pyrazole-4-carboxylic acid indan-2-ylamide, 5-ac etyl-thiophene-2-carboxylic acid indan-2-ylamide, and 2-chloro-N-indan-2-yl-6-methyl-nicotinamide.

In another embodiment of the present invention, the substituents $R^1$ to $R^5$, A and B and the groups aryl and heteroaryl according to the formula (I) have the following meanings.

$R^1$ and $R^4$ are independently from each other selected from the group consisting of: H; unsubstituted and at least monosubstituted $C_1$–$C_{10}$-alkyl, $C_2$–$C_{10}$-alkenyl and $C_2$–$C_{10}$-alkynyl, the substituents of which are selected from the group consisting of F, OH, $C_1$–$C_6$-alkoxy, ($C_1$–$C_6$-alkyl)mercapto, CN, $COOR^6$, $CONR^7R^8$, unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$; unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$; $R^9CO$; $CONR^{10}R^{11}$; $COOR^{12}$; $CF_3$; halogens; pseudohalogens; $NR^{13}R^{14}$; $OR^{15}$; $S(O)_mR^{16}$; $SO_2NR^{17}R^{18}$; and $NO_2$;

$R^2$ and $R^3$ are independently from each other selected from the group consisting of: H; halogens; pseudohalogens; unsubstituted and at least monosubstituted $C_1$–$C_6$-alkyl the substituents of which are selected from the group consisting of OH, phenyl, and heteroaryl; OH; $C_1$–$C_6$-alkoxy; phenoxy; $S(O)_mR^{19}$; $CF_3$; CN; $NO_2$; ($C_1$–$C_6$-alkyl)amino; di($C_1$–$C_6$-alkyl)amino; ($C_1$–$C_6$-alkyl)-CONH—; unsubstituted and at least monosubstituted phenyl-CONH and phenyl-$SO_2$—O—, the substituents of which are selected from the group consisting of halogens, pseudohalogens, $CH_3$ and methoxy; ($C_1$–$C_6$-alkyl)$SO_2$—O—; unsubstituted and at least monosubstituted ($C_1$–$C_6$-alkyl)CO, the substituents of which are selected from the group consisting of F, di($C_1$–$C_3$-alkyl)amino, pyrrolidinyl and piperidinyl; and phenyl-CO, the phenyl part of which can be substituted by one or more substituents from the group consisting of $C_1$–$C_3$-alkyl, halogens and methoxy;

A is $CH_2$, CHOH or CH—($C_1$–$C_3$-alkyl);
B is $CH_2$ or CH—($C_1$–$C_3$-alkyl);
$R^5$ is an aryl or a heteroaryl group which can be unsubstituted or carry one or more substituents selected from the group consisting of: halogens; pseudohalogens; $C_1$–$C_{10}$-alkyl; $C_3$–$C_5$-alkandiyl; phenyl; phenylsubstituted $C_1$–$C_4$-alkyl; $CF_3$; OH; $C_1$–$C_{10}$-alkoxy; phenoxy; benzyloxy; $CF_3O$; ($C_1$–$C_{10}$-alkyl)COO; $S(O)_mR^{20}$; ($C_1$–$C_{10}$-alkyl)amino; di($C_1$–$C_{10}$-alkyl)amino; ($C_1$–$C_{10}$-alkyl)-CONH—; ($C_1$–$C_{10}$-alkyl)-CON($C_1$–$C_3$-alkyl)-; ($C_1$–$C_{10}$-alkyl)-CO; $CF_3$—CO; —$OCH_2O$—; —$OCF_2$—; —$OCH_2CH_2O$—; —$CH_2CH_2O$—; phenylamino; phenyl-CO; $COOR^{21}$; $CONR^{22}R^{23}$; $SO_2NR^{24}R^{25}$; and aromatic or aliphatic, mononuclear 5-to 7-membered heterocycles containing 1 to 3 heteroatoms from the group consisting of N, O, and S which can be substituted by one or more substituents from the group consisting of halogens, $C_3$–$C_3$-alkyl, $C_1$–$C_3$-alkoxy and $CF_3$; wherein all phenyl groups and phenyl-containing groups which may be present in the said substituents of the said aryl or heteroaryl groups can be substituted by one or more groups selected from halogens, pseudohalogens, $C_1$–$C_3$-alkyl, $C_1$–$C_3$-alkoxy, and $CF_3$;

$R^6$ is H, $C_1$–$C_6$-alkyl or benzyl;
$R_7$ is selected from the group consisting of: H; $C_1$–$C_6$-alkyl which can be phenyl-substituted; phenyl; indanyl; and heteroaryl; and wherein each of the aforementioned aromatic groups can be unsubstituted or carry one or more substituents from the group consisting of halogens, pseudohalogens, $C_1$–$C_3$-alkyl, $C_1$–$C_3$-alkoxy and $CF_3$;
$R^8$ is H or $C_1$–$C_6$-alkyl;
$R^9$ is $C_1$–$C_6$-alkyl which can be unsubstituted or carry one or more substituents from the group consisting of: F; di($C_1$–$C_3$-alkyl)amino; and unsubstituted and at least monosubstituted phenyl and heteroaryl, the substituents of which are selected from the group consisting of $C_1$–$C_3$-alkyl, $C_1$–$C_3$-alkoxy, halogens, pseudohalogens, and $CF_3$;
$R^{10}$ independently has the same meaning as $R^7$;
$R^{11}$ independently has the same meaning as $R^8$;
$R^{12}$ independently has the same meaning as $R^6$;
$R^{13}$ is selected from the group consisting of. H; $C_1$–$C_3$-alkyl; and unsubstituted and substituted phenyl, benzyl, heteroaryl, phenyl-CO, and heteroaryl-CO, the substituents of which are selected from the group consisting of halogens, pseudohalogens, $C_1$–$C_3$-alkyl, $C_1$–$C_3$-alkoxy, and $CF_3$, and wherein one or more of these substituents can be present;
$R^{14}$ is H or $C_1$–$C_6$-alkyl;
$R^{15}$ is selected from the group consisting of: H; $C_1$–$C_6$-alkyl; and substituted and unsubstituted benzyl, phenyl and heteroaryl, the substituents of which are selected from the group consisting of halogens, pseudohalogens, $C_1$–$C_3$-alkyl, $C_1$–$C_3$-alkoxy, and $CF_3$, and wherein one or more of these substituents can be present;
$R^{16}$ is selected from the group consisting of: $C_1$–$C_6$-alkyl; $CF_3$; and substituted and unsubstituted phenyl and heteroaryl, the substituents of which are selected from the group consisting of halogens, pseudohalogens, $C_1$–$C_3$-alkyl, $C_1$–$C_3$-alkoxy, and $CF_3$, and wherein one or more of these substitutents can be present;
$R^{17}$ independently has the same meaning as $R^7$;
$R^{18}$ independently has the same meaning as $R^8$;
$R^{19}$ independently has the same meaning as $R^{16}$;
$R^{20}$ independently has the same meaning as $R^{16}$;
$R^{21}$ independently has the same meaning as $R^6$;
$R^{22}$ independently has the same meaning as $R^7$;
$R^{23}$ independently has the same meaning as $R^8$;
$R^{24}$ independently has the same meaning as $R^7$;
$R^{25}$ independently has the same meaning as $R^8$;
heteroaryl is a 5 to 10-membered, mono- or bicyclic aromatic heterocycle containing one or more heteroatoms from the group consisting of N, O, and S;
aryl is phenyl, naphth-1-yl or naphth-2-yl;
m is 0, 1 or 2,
with the proviso that, in case $R^1$, $R^2$, $R^3$ and $R^4$ are all H, R5 is not phenyl, 5-chloro-2-ethoxyphenyl, 5-chloro-2-methoxyphenyl, 5-bromo-2-methoxyphenyl; or quinoxalin-2-yl; in case $R^5$ is phenyl, A is not CHOH, $R^1$ is not methoxy or methyl, $R^2$ is not methyl or B is not CH—$CH_3$; in case $R^2$ is $NO_2$, $R^5$ is not 3-chlorophenyl.

The compounds according to general formula (I) and their precursors can be prepared according to methods published in the literature or, respectively, analogous methods. Appropriate methods have been published in, for example, Masui et al., Tetrahedron Lett. 39 (1998) 5195, Colette et al., Ann. Chim. (Paris) 1 (1976) 269, Cannon et al., J. Med. Chem. 15 (1972) 348, Cannon et al., J. Med. Chem. 25 (1982) 1442, U.S. Pat. No. 4,192,888 and Crooks, Chem. Ind. (London) 12 (1974) 495. Indanyl amines prepared according to the disclosed methods can be dissolved in a solvent such as, for example, dichloromethane, THF, toluene or dioxane and reacted in the presence of base such as, for example, triethylamine, with an appropriate carboxylic acid derivative, for example a carboxylic acid chloride. This reaction is preferably carried out at room temperature. Alternatively, the compounds according to the general formula (I) are obtained by a coupling reaction of the respective indanyl amine with an acid, which indanyl amine and/or acid may be substituted and/or functionalized, in the presence of a base such as, for example, diisopropylethylamine, and the use of an appropriate coupling reagent like, for example, carbodiimides, HATU or TOTU. The thus obtained acyl indanyl amines can then be functionalized, in order to obtain further desired compounds according to the general formula (I). The reaction leading to the above-mentioned acyl indanyl amines and the reactions used in the functionalization are known to the person skilled in the art.

All reactions for the synthesis of the compounds of the formula (I) are per se well-known to the skilled person and can be carried out under standard conditions according to or analogously to procedures described in the literature, for example in Houben-Weyl, Methoden der Organischen Chemie (Methods of Organic Chemistry), Thieme-Verlag, Stuttgart, or Organic Reactions, John Wiley & Sons, New York. Depending on the circumstances of the individual case, in order to avoid side reactions during the synthesis of a compound of the formula (I), it can be necessary or advantageous to temporarily block functional groups by introducing protective groups and to deprotect them in a later stage of the synthesis, or introduce functional groups in the form of precursor groups which in a later reaction step are converted into the desired functional groups. Such synthesis strategies and protective groups and precursor groups which are suitable in an individual case are known to the skilled person. If desired, the compounds of the formula (I) can be purified by customary purification procedures, for example by recrystallization or chromatography. The starting compounds for the preparation of the compounds of the formula (I) are commercially available or can be prepared according to or analogously to literature procedures. The compounds obtained with the above-mentioned synthesis methods are a further object of the present invention.

Some of the compounds falling under formula (I) are disclosed in the literature. However, their use as a pharmaceutical compound is not disclosed in any of these references. The compounds are, for example, disclosed in Tetrahedron. Lett. (1998), 39(29), 5195–5198; Tetrahedron. Lett. (1998), 39(5/6), 497–500; JP 09255592; WO 99/26927; WO 97/06158, U.S. Pat. No. 5,583,221; WO 96/24588; Biorg. Med. Chem. Lett. (1996),6(8), 973–978; WO 95/30640; EP-A 0 399 422; Helv. Chim. Acta (1977), 60(6), 2089–98; Ann. Chim. (Paris) (1976), 1(5), 269–76; Khim. Geterosikl. Soedin. (1974),(12), 1629–38; Chem:Ind (1974),(12), 495; Liebigs Ann. Chem. (1971), 743, 42–49; J. Org. Chem. (1970), 35(4), 1149–54; and ZA-A 6806875.

WO 00/51970 discloses compounds according to the general formula (II) and their use for the potentation of cholinergic activity.

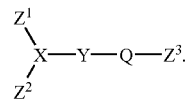

In the above formula:

$Z^1$ and $Z^2$ are each aryl or ar(lower)alkyl, or are taken together to form lower alkylene or lower alkenylene, each of which may be substituted with aryl or may be condensed with a cyclic hydrocarbon optionally substituted with lower alkyl, lower alkoxy, aryl, aryloxy or halogen, $Z^3$ is lower alkyl, lower alkoxy, aryl, arylamino or aryloxy, each of which may be substituted with lower alkoxy or halogen, pyridyl, or pyridylamino, X is CH or N, Y is a single bond or —NH—, and

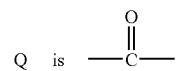

Referring to the definition of $Z^1$ and $Z^2$ in formula (II), it is stated that preferred lower alkylenes are tetramethylene or pentamethylene, preferred lower alkenylenes are butenylene, pentenylene or methylpentenylene, a preferred cyclic hydrocarbon is benzene and a preferred aryl is phenyl.

Furthermore, it is stated that, among other, preferred compounds according to the general formula (II) are those having lower alkenylene which may be substituted with aryl or may be condensed with benzene optionally substituted with lower alkoxy for $Z^1$ and $Z^2$ to be taken together to form, aryl or arylamino, each of which may be substituted with halogen, pyridyl, or pyridylamino for $Z^3$, CH or N for X, a single bond or —NH— for Y, and

for Q.

More preferred compounds according to the general formula (II) are those having $Z^1$ and $Z^2$ taken together to form methylpentenylene, butenylene condensed with benzene, or pentenylene which may be condensed with benzene optionally substituted with lower alkoxy.

As an example, 4-fluoro-N-(indan2-yl)benzamide is provided.

Compounds explicitly disclosed by WO 00/51970 are not an object of the present invention.

The present invention also relates to acylated indanyl amines according to the general formula (I) in any of their stereoisomeric forms or mixtures thereof in any ratio and their pharmaceutically acceptable salts for use as pharmaceuticals.

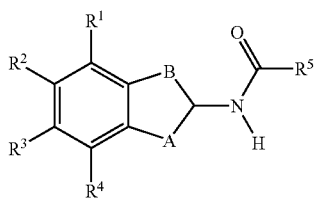

(I)

In the above formula (I), $R^1$ and $R^4$ are independently from each other selected from the group consisting of: H; unsubstituted and at least monosubstituted $C_1$–$C_{10}$-alkyl, $C_2$–$C_{10}$-alkenyl and $C_2$–$C_{10}$-alkynyl, the substituents of which are selected from the group consisting of F, OH, $C_1$–$C_8$-alkoxy, ($C_1$–$C_8$-alkyl)mercapto, CN, $COOR^6$, $CONR^7R^8$, and unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$; unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$; $R^9CO$; $CONR^{10}R^{11}$; $COOR^{12}$; $CF_3$; halogens; pseudohalogens; $NR^{13}R^{14}$; $OR^{15}$; $S(O)_mR^{16}$; $SO_2NR^{17}R^{18}$; and $NO_2$;

$R^2$ and $R^3$ are independently from each other selected from the group consisting of: H; halogens; pseudohalogens; unsubstituted and at least monosubstituted $C_1$–$C_{10}$-alkyl the substituents of which are selected from the group consisting of OH, phenyl, and heteroaryl; OH; $C_1$–$C_{10}$-alkoxy; phenoxy; $S(O)_mR^{19}$; $CF_3$; CN; $NO_2$; ($C_1$–$C_{10}$-alkyl)amino; di($C_1$–$C_{10}$-alkyl)amino; ($C_1$–$C_6$-alkyl)-CONH—; unsubstituted and at least monosubstituted phenyl-CONH— and phenyl-$SO_2$—O—, the substituents of which are selected from the group consisting of halogens, pseudohalogens, $CH_3$ and methoxy; ($C_1$–$C_6$-alkyl)$SO_2$—O—; unsubstituted and at least monosubstituted ($C_1$–$C_6$-alkyl)CO, the substituents of which are selected from the group consisting of F, di($C_1$–$C_3$-alkyl)amino, pyrrolidinyl and piperidinyl; and phenyl-CO, the phenyl part of which can be substituted by one or more substituents from the group consisting of $C_1$–$C_3$-alkyl, halogens and methoxy;

A is selected from the group consisting of $CH_2$, CHOH and CH—($C_1$–$C_3$-alkyl);

B is selected from the group consisting of $CH_2$ and CH—($C_1$–$C_3$-alkyl);

$R^5$ is a group Ar or a group Hetar both of which can be unsubstituted or carry one or more substituents selected from the group consisting of: halogens; pseudohalogens; $NH_2$; unsubstituted and at least monosubstituted $C_1$–$C_{10}$-alkyl, $C_2$–$C_{10}$-alkenyl, $C_2$–$C_{10}$-alkynyl, $C_1$–$C_{10}$-alkoxy, ($C_1$–$C_{10}$-alkyl)amino, di($C_1$–$C_{10}$-alkyl)amino, the substituents of which are selected from the group consisting of F, OH, $C_1$–$C_8$-alkoxy, aryloxy, ($C_1$–$C_8$-alkyl)mercapto, $NH_2$, ($C_1$–$C_8$-alkyl)amino, and di($C_1$–$C_8$-alkyl)amino; $C_3$–$C_5$-alkandiyl; phenyl; heteroaryl; aryl- or heteroaryl-substituted $C_1$–$C_4$-alkyl; $CF_3$; $NO_2$; OH; phenoxy; benzyloxy; ($C_1$–$C_{10}$-alkyl)COO; $S(O)_mR^{20}$; SH; phenylamino; benzylamino; ($C_1$–$C_{10}$-alkyl)-CONH—; ($C_1$–$C_{10}$-alkyl)-CON($C_1$–$C_4$-alkyl)-; phenyl-CONH—; phenyl-CON($C_1$–$C_4$-alkyl)-; heteroaryl-CONH—; heteroaryl-CON($C_1$–$C_4$-alkyl)-; ($C_1$–$C_{10}$-alkyl)-CO; phenyl-CO; heteroaryl-CO; $CF_3$—CO; —$OCH_2O$—; —$OCF_2O$—; —$OCH_2CH_2O$—; —$CH_2CH_2O$—; $COOR^{21}$; $CONR^{22}R^{23}$; $CNH(NH_2)$;

$SO_2NR^{24}R^{25}$; $R^{26}SO_2NH$—; $R^{27}SO_2N(C_1$–$C_6$-alkyl)-; and saturated or at least monounsaturated aliphatic, mononuclear 5- to 7-membered heterocycles containing 1 to 3 heteroatoms selected from the group consisting of N, O and S, which heterocycles can be substituted by one or more substituents selected from the group consisting of halogens, $C_1$–$C_3$-alkyl, $C_1$–$C_3$-alkoxy, OH, oxo and $CF_3$, where said heterocycles can optionally be condensed to the said group Ar or the said group Hetar; wherein all aryl, heteroaryl, phenyl, aryl-containing, heteroaryl-containing and phenyl-containing groups, which are optionally present in the said substituents of the said group Ar or the said group Hetar, can be substituted by one or more substituents selected from the group consisting of halogens, pseudohalogens, $C_1$–$C_3$-alkyl, OH, $C_1$–$C_3$-alkoxy, and $CF_3$;

$R^6$ is selected from the group consisting of: H; $C_1$–$C_{10}$-alkyl, which can be substituted by one or more substituents selected from the group consisting of F, $C_1$–$C_8$-alkoxy, and di($C_1$–$C_8$-alkyl)amino; aryl-($C_1$–$C_4$-alkyl) and heteroaryl-($C_1$–$C_4$-alkyl), which can be substituted by one or more substituents selected from the group consisting of halogens, $C_1$–$C_4$-alkoxy, and di($C_1$–$C_6$-alkyl)amino;

$R^7$ is selected from the group consisting of: H; $C_1$–$C_{10}$-alkyl which can be substituted by one or more substituents selected from the group consisting of F, $C_1$–$C_8$-alkoxy, di($C_1$–$C_8$-alkyl)amino and phenyl; phenyl; indanyl; and heteroaryl; and wherein each of the aforementioned aromatic groups can be unsubstituted or carry one or more substituents from the group consisting of halogens, pseudohalogens, $C_1$–$C_3$-alkyl, $C_1$–$C_3$-alkoxy and $CF_3$;

$R^8$ is H or $C_1$–$C_{10}$-alkyl;

$R^9$ is selected from the group consisting of: $C_1$–$C_{10}$-alkyl which can be unsubstituted or carry one or more substituents from the group consisting of: F, ($C_1$–$C_4$)-alkoxy, di($C_1$–$C_3$-alkyl)amino; and unsubstituted and at least monosubstituted phenyl and heteroaryl, the substituents of which are selected from the group consisting of $C_1$–$C_3$-alkyl, $C_1$–$C_3$-alkoxy, halogens, pseudohalogens, and $CF_3$;

$R^{10}$ independently has the same meaning as $R^7$;

$R^{11}$ independently has the same meaning as $R^8$;

$R^{12}$ independently has the same meaning as $R^6$;

$R^{13}$ is selected from the group consisting of: H; $C_1$–$C_6$-alkyl; unsubsiituted and substituted phenyl, benzyl, heteroaryl, ($C_1$–$C_6$-alkyl)-CO, phenyl-CO, and heteroaryl-CO, the substituents of which are selected from the group consisting of halogens, pseudohalogens, $C_1$–$C_3$-alkyl, $C_1$–$C_3$-alkoxy, and $CF_3$, and wherein one or more of these substituents can be present;

$R^{14}$ independently has the same meaning as $R^{13}$;

$R^{15}$ is selected from the group consisting of: H; $C_1$–$C_{10}$-alkyl; ($C_1$–$C_3$-alkoxy)-$C_1$–$C_3$-alkyl; and substituted and unsubstituted benzyl, phenyl and heteroaryl, the substituents of which are selected from the group consisting of halogens, pseudohalogens, $C_1$–$C_3$-alkyl, $C_1$–$C_3$-alkoxy, and $CF_3$, and wherein one or more of these substituents can be present;

$R^{16}$ is selected from the group consisting of: $C_1$–$C_{10}$-alkyl which can be substituted by one or more substituents selected from the group consisting of F, OH, $C_1$–$C_8$-alkoxy, aryloxy, ($C_1$–$C_8$-alkyl)mercapto, ($C_1$–$C_8$-alkyl)amino and di($C_1$–$C_8$-alkyl)amino; $CF_3$; and substituted and unsubstituted phenyl and heteroaryl, the substituents of which are selected from the group consisting of halogens, pseudohalogens, $C_1$–$C_3$-alkyl, $C_1$–$C_3$-alkoxy and $CF_3$, and wherein one or more of these substitutents can be present;

$R^{17}$ independently has the same meaning as $R^7$;

$R^{18}$ independently has the same meaning as $R^8$;

$R^{19}$ independently has the same meaning as $R^{16}$;

$R^{20}$ independently has the same meaning as $R^{16}$;
$R^{21}$ independently has the same meaning as $R^6$;
$R^{22}$ independently has the same meaning as $R^7$;
$R^{23}$ independently has the same meaning as $R^8$;
$R^{24}$ independently has the same meaning as $R^7$;
$R^{25}$ independently has the same meaning as $R^8$;
$R^{26}$ independently has the same meaning as $R^{16}$;
$R^{27}$ independently has the same meaning as $R^{16}$;

heteroaryl is a 5 to 10-membered, aromatic, mono- or bicyclic heterocycle containing one or more heteroatoms selected from the group consisting of N, O, and S;

the group Hetar is a 5 to 1 0-membered, aromatic, mono- or bicyclic heterocycle containing one or more heteroatoms selected from the group consisting of N, O, and S;

aryl is phenyl, naphth-1-yl or naphth-2-yl;

the group Ar is phenyl, naphth-1-yl or naphth-2-yl; and m is 0, 1 or 2;

With respect to the definitions given above in the context of the compounds for use as pharmaceuticals according to the general formula (I), the same explanations as laid out above in the context with the compounds as such apply.

Compounds of the formula (I) for use as pharmaceutical, in which one or more, including all, of the above-mentioned groups have the preferred meanings, the more preferred meanings, the even more preferred meanings, the most preferred meanings, or the particularly preferred meanings defined above are also an object of the present invention.

In a further embodiment, the object of the present invention is attained by compounds of the formula (I) for use as pharmaceutical wherein the substituents $R^1$ to $R^5$, A and B and the groups aryl and heteroaryl have the following meanings.

$R^1$ and $R^4$ are independently from each other selected from the group consisting of: H; unsubstituted and at least monosubstituted $C_1$–$C_{10}$-alkyl, $C_2$–$C_{10}$-alkenyl and $C_2$–$C_{10}$-alkynyl, the substituents of which are selected from the group consisting of F, OH, $C_1$–$C_6$-alkoxy, ($C_1$–$C_6$-alkyl) mercapto, CN, $COOR^6$, $CONR^7R^8$, unsubstituted and at least monosubstituted phenyl and heteroaryl, the substituents of which are selected from the group consisting of halogens, pseudohalogens, $C_{10}$–$C_3$-alkyl, $C_1$–$C_3$-alkoxy and $CF_3$; unsubstituted and at least monosubstituted phenyl and heteroaryl, the substituents of which are selected from the group consisting of halogens, pseudohalogens, $C_1$–$C_3$-alkyl, $C_1$–$C_3$-alkoxy and $CF_3$; $R^9CO$; $CONR^{10}R^{11}$; $COOR^{12}$; $CF_3$; halogens; pseudohalogens; $NR^{13}R^{14}OR^{15}$; $S(O)_mR^{16}$; $SO_2NR^{17}R^{18}$; and $NO_2$;

$R^2$ and $R^3$ are independently from each other selected from the group consisting of: H; halogens; pseudohalogens; unsubstituted and at least monosubstituted $C_1$–$C_6$-alkyl the substituents of which are selected from the group consisting of OH, phenyl, and heteroaryl; OH; $C_1$–$C_6$-alkoxy; phenoxy; $S(O)_mR^{19}$; $CF_3$; CN; $NO_2$; ($C_1$–$C_6$-alkyl)amino; di($C_1$–$C_6$-alkyl)amino; ($C_1$–$C_6$-alkyl)-CONH—; unsubstituted and at least monosubstituted phenyl-CONH and phenyl-$SO_2$—O—, the substituents of which are selected from the group consisting of halogens, pseudohalogens, $CH_3$ and methoxy; ($C_1$–$C_6$-alkyl)$SO_2$—O—; unsubstituted and at least monosubstituted ($C_1$–$C_6$-alkyl)CO, the substituents of which are selected from the group consisting of F, di($C_1$–$C_3$-alkyl)amino, pyrrolidinyl. and piperidinyl. and phenyl-CO, the phenyl part of which can be substituted by one or more substituents from the group consisting of $C_1$–$C_3$-alkyl, halogens and methoxy;

A is $CH_2$, CHOH or CH—($C_1$–$C_3$-alkyl);

B is $CH_2$ or CH—($C_1$–$C_3$-alkyl);

$R^5$ is an aryl or a heteroaryl group which can be unsubstituted or carry one or more substituents selected from the group consisting of: halogens; pseudohalogens; $C_1$–$C_{10}$-alkyl; $C_3$–$C_5$-alkandiyl; phenyl; phenylsubstituted $C_1$–$C_4$-alkyl; $CF_3$; OH; $C_1$–$C_{10}$-alkoxy; phenoxy; benzyloxy; $CF_3O$; ($C_1$–$C_{10}$-alkyl)COO; $S(O)_mR^{20}$; ($C_1$–$C_{10}$-alkyl) amino; di($C_1$–$C_{10}$-alkyl)amino; ($C_1$–$C_{10}$-alkyl)-CONH—; ($C_1$–$C_{10}$-alkyl)-CON($C_1$–$C_3$-alkyl)-; ($C_1$–$C_{10}$-alkyl)-CO; $CF_3$—CO; —$OCH_2O$—; —$OCF_2O$—; —$OCH_2CH_2O$—; —$CH_2CH_2O$—; phenylamino; phenyl-CO; $COOR^{21}$; $CONR^{22}R^{23}$; $SO_2NR^{24}R^{25}$; and aromatic or aliphatic, mononuclear 5- to 7-membered heterocycles containing 1 to 3 heteroatoms from the group consisting of N, O, and S which can be substituted by one or more substituents from the group consisting of halogens, $C_1$–$C_3$-alkyl, $C_1$–$C_3$-alkoxy and $CF_3$; wherein all phenyl groups and phenyl-containing groups which may be present in the said substituents, of the said aryl or heteroaryl groups can be substituted by one or more groups selected from halogens, pseudohalogens, $C_1$–$C_3$-alkyl, $C_1$–$C_3$-alkoxy, and $CF_3$;

$R^6$ is H, $C_1$–$C_6$-alkyl or benzyl;

$R^7$ is selected from the group consisting of: H; $C_1$–$C_6$-alkyl which can be phenyl-substituted; phenyl; indanyl; and heteroaryl; and wherein each of the aforementioned aromatic groups can be unsubstituted or carry one or more substituents from the group consisting of halogens, pseudohalogens, $C_1$–$C_3$-alkyl, $C_1$–$C_3$-alkoxy and $CF_3$;

$R^8$ is H or $C_1$–$C_6$-alkyl;

$R^9$ is $C_1$–$C_6$-alkyl which can be unsubstituted or carry one or more substituents from the group consisting of: F; di($C_1$–$C_3$-alkyl)amino; and unsubstituted and at least monosubstituted phenyl and heteroaryl, the substituents of which are selected from the group consisting of $C_1$–$C_3$-alkyl, $C_1$–$C_3$-alkoxy, halogens, pseudohalogens, and $CF_3$;

$R^{10}$ independently has the same meaning as $R^7$;
$R^{11}$ independently has the same meaning as $R^8$;
$R^{12}$ independently has the same meaning as $R^6$;
$R^{13}$ is selected from the group consisting of: H; $C_1$–$C_6$-alkyl; and unsubstituted and substituted phenyl, benzyl, heteroaryl, phenyl-CO, and heteroaryl-CO, the substituents of which are selected from the group consisting of halogens, pseudohalogens, $C_1$–$C_3$-alkyl, $C_1$–$C_3$-alkoxy, and $CF_3$, and wherein one or more of these substituents can be present;

$R^{14}$ is H or $C_1$–$C_6$-alkyl;

$R^{15}$ is selected from the group consisting of: H; $C_1$–$C_6$-alkyl; and substituted and unsubstituted benzyl, phenyl and heteroaryl, the substituents of which are selected from the group consisting of halogens, pseudohalogens, $C_1$–$C_3$-alkyl, $C_1$–$C_3$-alkoxy, and $CF_3$, and wherein one or more of these substituents can be present;

$R^{16}$ is selected from the group consisting of: $C_1$–$C_6$-alkyl; $CF_3$; and substituted and unsubstituted phenyl and heteroaryl, the substituents of which are selected from the group consisting of halogens, pseudohalogens, $C_1$–$C_3$-alkyl, $C_1$–$C_3$-alkoxy, and $CF_3$, and wherein one or more of these substitutents, can be present;

$R^{17}$ independently has the same meaning as $R^7$;
$R^{18}$ independently has the same meaning as $R^8$;
$R^{19}$ independently has the same meaning as $R^{16}$;
$R^{20}$ independently has the same meaning as $R^{16}$;
$R^{21}$ independently has the same meaning as $R^6$;
$R^{22}$ independently has the same meaning as $R^7$;
$R^{23}$ independently has the same meaning as $R^8$;
$R^{24}$ independently has the same meaning as $R^7$;
$R^{25}$ independently has the same meaning as $R^8$;

heteroaryl is a 5 to 10-membered, mono- or bicyclic aromatic heterocycle containing one or more heteroatoms from the group consisting of N, O, and S;

aryl is phenyl, naphth-1-yl or naphth-2-yl;

m is 0, 1 or 2.

The compounds according to the general formula (I) can be used to upregulate the expression of the endothelial NO synthase and are helpful pharmaceutical compounds for the treatment of various diseases. In the context of the present invention, treatment includes the therapy as well as the prophylaxis of the respective diseases.

Examples of diseases which can be treated with the compounds according to the present invention include cardiovascular diseases like stable and unstable angina pectoris, coronary heart disease, Prinzmetal angina (spasm), acute coronary syndrome, heart failure, myocardial infarction, stroke, thrombosis, peripheral artery occlusive disease (PAOD), endothelial dysfunction, atherosclerosis, restenosis, endothelial damage after PTCA, hypertension including essential hypertension, pulmonary hypertension, and secondary hypertension (renovascular hypertension, chronic glomerulonephritis), erectile dysfunction, ventricular arrhythmia, and the lowering of cardiovascular risk of postmenopausal women or after intake of contraceptives.

Compounds of the formula (I) can additionally be used in the therapy and prophylaxis of diabetes and diabetes complications (nephropathy, retinopathy), angiogenesis, asthma bronchiale, chronic renal failure, cirrhosis of the liver, osteoporosis, restricted memory performance or a restricted ability to learn.

Preferred indications are stable angina pectoris, coronary heart disease, hypertension, endothelial dysfunction, atherosclerosis and diabetes complications.

The compounds according to the formula (I) can also be used in combination with other pharmaceutically active compounds, preferably compounds which are able to enhance the effect of the compounds according to the general formula (I). Examples of such compounds include: statins; ACE-inhibitors; ATI-antagonists; argininase-inhibitors; PDE V-inhibitors; Ca-antagonists; alpha-blockers; beta-blockers; metimazol and analogous compounds; arginine; tetrahydrobiopterin; vitamins, in particular vitamin C and vitamin B6; and niacin.

The compounds of the formula (1) and their pharmaceutically acceptable salts, optionally in combination with other pharmaceutically active compounds, can be administered to animals, preferably to mammals, and in particular to humans, as pharmaceuticals by themselves, in mixtures with one another or in the form of pharmaceutical preparations. Further subjects of the present invention therefore also are the compounds of the formula (I) and their pharmaceutically acceptable salts for use as pharmaceuticals, their use as transcription stimulating agent for endothelial NO synthase and in particular their use in the therapy and prophylaxis of the above-mentioned syndromes as well as their use for preparing medicaments for these purposes. Furthermore, subjects of the present invention are pharmaceutical preparations (or pharmaceutical compositions) which comprise an effective dose of at least one compound of the formula (I) and/or a pharmaceutically acceptable salt thereof and a pharmaceutically acceptable carrier, i.e. one or more pharmaceutically acceptable carrier substances and/or additives.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The amount of compounds of the formula (I) and/or its pharmaceutically acceptable salts in the pharmaceutical preparations normally ranges from 0.2 to 800 mg, preferably from 0.5 to 500 mg, in particular from 1 to 200 mg, per dose, but depending on the type of the pharmaceutical preparation it may also be higher. The pharmaceutical preparations usually comprise 0.5 to 90 percent by weight of the compounds of the formula (I) and/or their pharmaceutically acceptable salts. The preparation of the pharmaceutical preparations can be carried out in a manner known per se. To this end, one or more compounds of the formula (I) and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the formula (I) and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the compound or compounds according to the invention and carriers, the pharmaceutical preparations can also contain additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the compound of the formula (I) to be administered and/or of a pharmaceutically acceptable salt thereof depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of the formula (I). In general, a daily dose of approximately 0.01 to 100 mg/kg, preferably 0.1 to 10 mg/kg, in particular 0.3 to 5 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose.

The compounds according to the formula (I) can also be used for other purposes than those indicated in the foregoing. Non-limiting examples include diagnostic purposes, the use as biochemical tools, and as intermediates for the preparation of further compounds, e.g. pharmaceutically active compounds.

The present invention will now be illustrated in the following examples:

EXAMPLES

Ex 1

4-FLUORO-N-(4-METHYL-INDAN-2-YL)-BENZAMIDE 370 mg (2.52 mmol) 2-amino-4-methylindane and 257mg (2.52 mmol) triethylamine were dissolved in 5 ml dioxane, 400 mg (2.52 mmol) 4-fluorobenzoylchloride were added, and the mixture was stirred for 2 h at room temperature (RT).

The resulting mixture was then poured onto an ice/HCl-mixture, extracted with ethyl acetate and concentrated. The thus-obtained residue was fractionated with prep. HPLC (RP 18, acetonitrile/water, 0.1% trifluoroacetic acid). Yield: 370 mg (87%), mp.: 154° C. $^1$H (d6-DMSO, 300 MHz): 2.20 (s, 3H, CH$_3$) 2.80–3.00 (m, 2H, —CH$_2$—) 3.16–3.30 (m, 2H, —CH$_2$—), 4.69 (quint, 1H, CH—N), 6.92–7.10 (m, 3H, H$^5$, H$^6$, H$^7$), 7.39 (t, 2H, H$^{31}$, H$^{51}$), 7.94 (dd, 2H, H$^{21}$, H$^{61}$), 8.67 (d, 1H, NH)

The enantiomers were separated by prep. HPLC (Chiralpeak AD, elution agent n-heptane:isopropanol 10:1):, a) (−)-4-Fluoro-N-(4-methyl-indan-2-yl)-benzamide retention-time: 8.69 b) (+)-4-Fluoro-N-(4-methyl-indan-2-yl)-benzamide retention-time: 9.46

The following compounds were obtained in an analogous way:

Ex 2

4-FLUORO-N-(5-METHOXY-INDAN-2-YL)-BENZAMIDE mp.: 160° C.

Ex 3

4-FLUORO-N-(5,6-DIMETHOXY-INDAN-2-YL)-BENZAMIDE mp.: 160° C.

Ex 4

4-FLUORO-N-(5-FLUORO-INDAN-2-YL)-BENZAMIDE mp.: 144° C.

Ex 5

4-FLUORO-N-(5-METHYL-INDAN-2-YL)-BENZAMIDE mp.: 143° C.

Ex 6

ACETIC ACID 5-ETHOXY-2-(INDAN-2-YL-CARBAMOYL)-PHENYL ESTER mp.: 139° C.

Ex 7

ACETIC ACID 2-(INDAN-2-YL-CARBAMOYL)-5-METHYL-PHENYLESTER mp.: 116° C.

Ex 8

4-FLUORO-N-(TRANS-1-HYDROXY-INDAN-2-YL)-BENZAMIDE mp.: 247° C.

Ex 9

BENZO[1,3]DIOXOL-5-CARBOXYLIC-ACID (5-NITRO-INDAN-2-YL)-AMIDE mp: 229° C.

Ex 10

BENZO[1,3]DIOXOL-5-CARBOXYLIC-ACID (6-CHLOR-1-HYDROXY-INDAN-2-YL)-AMIDE mp: 255° C.

Ex 11

4-FLUORO-N-(4-FLUORO-INDAN-2-YL)-BENZAMIDE

[M+H$^+$] measured: 274 retention-time: 4.91

Ex 12

4-FLUORO-N-(4-HYDROXY-INDAN-2-YL)-BENZAMIDE

[M+H$^+$] measured: 272 retention-time: 4.37

Ex 13

4-FLUORO-N-(4-ISOPROPOXY-INDAN-2-YL)-BENZAMIDE

[M+H$^+$] measured: 314 retention-time: 5.21

Ex 14

N-(5,6-DICHLORO-INDAN-2-YL)-
4-FLUORO-BENZAMIDE

[M+H$^+$] measured: 324 retention-time: 5.01

Ex 15A

N-(4-CHLORO-INDAN-2-YL)-
4-FLUORO-BENZAMIDE

[M+H$^+$] measured: 290 retention-time: 4.94 (Rf on prep. HPLC (Chiralpeak AD, solvent acetonitrile:isopropanol 9:1))

Ex 15B

N-(4-CHLORO-INDAN-2-YL)-
4-FLUORO-BENZAMIDE

[M+H$^+$] measured: 290 retention-time: 16.79 (Rf on prep. HPLC (Chiralpeak AD, solvent acetonitrile:isopropanol 9:1))

One of the compounds of examples 15A and 15B is the R enantiomer and the other one is the S enantiomer.

Ex 16A

N-(5-CHLORO-INDAN-2-YL)-
4-FLUORO-BENZAMIDE

[M+H$^+$] measured: 290 retention-time: 7.21 (Rf on prep. HPLC (Chiralpeak AD, solvent acetonitrile:isopropanol 9:1))

Ex 16B

N-(5-CHLORO-INDAN-2-YL)-
4-FLUORO-BENZAMIDE

[M+H$^+$] measured: 290 retention-time: 20.12 (Rf on prep. HPLC (Chiralpeak AD, solvent acetonitrile:isopropanol 9:1))

One of the compounds of examples 16A and 16B is the R enantiomer and the other one is the S enantiomer.

Ex 17

N-(4,7-DIMETHOXY-INDAN-2-YL)-
4-FLUORO-BENZAMIDE

[M+H$^+$] measured: 316 retention-time: 4.81

Ex 18

4-FLUORO-N-(2-METHYL-INDAN-
2-YL)-BENZAMIDE

[M+H$^+$] measured: 270 retention-time: 2.49 condition: b

Ex 19

2-AMINO-N-(2-METHYL-INDAN-
2-YL)-NICOTINAMIDE

[M+H$^+$] measured: 268 retention-time: 1.75 condition: b

Ex 20

2,5-DIMETHYL-1-PYRIDIN-4-YLMETHYL-1H-
PYRROLE-3-CARBOXYLIC ACID (2-METHYL-
INDAN-2-YL)-AMIDE

[M+H$^+$] measured: 360 Retention-time: 1.89 condition: b

Ex 21

4-FLUORO-N-(INDAN-2-YL)-BENZAMIDE 43.70 g (258 mol) 2-aminoindane hydrochloride and 53.43 g (528 mmol) triethylamine were added to 250 ml of tetrahydrofuran, 42.89 g (270 mmol) 4-fluorobenzoylchloride were added, and the mixture was stirred for 2 h at RT.

The resulting mixture was then poured onto an ice/HCl-mixture, the obtained precipitate was filtered, washed with a NaHCO$_3$-solution and water and dried in vacuo. The crude product was crystallized from methanol. There were obtained 47.8 g (73%) of a white, crystalline product.

mp.: 167° C. MS: [M+H$^+$]:256.1 $^1$H-NMR (300 MHz, d$_6$-DMSO): 2.96 (dd, 2H, H1/3), 3.25 (dd, 2H, H3/1), 4.70 (sextett, 1H, H2), 7.12–7.19 (m, 2H, H4,7/5,6), 7.20–7.28 (m., 2H, H5,6/4,7), 7.30 (t, 2H, H3', 5'), 7.95 (dd, 2H, H2',6'), 8.68 (d, 1H, NH)

Coupling of Indanyl Amines with Various Aromatic Carboxylic Acids

Method A:

0.5 mmol (96 mg) 1-ethyl-3-(3-(dimethylaimno)propyl) carbodiimide hydrochloride and 0.5 mmol (87 μl diisopropylethyl amine (DIPEA) were dissolved in 2.5 ml of dichloromethane, added to a solution of 0.5 mmol of the respective acid in 2.5 ml of dichloromethane (DCM) and stirred for 10 min at room temperature. There were then added 0.7 mmol of the respective indanyl amine and stirring was continued overnight.

The resulting solution was then washed 2× with 2N HCl and once with a saturated KHCO$_3$-solution, dried over MgSO$_4$, filtered and the residue obtained after evaporating to dryness was crystallized from ethyl acetate/hexane- or MeOH-diethylether-mixtures or purified with HPLC.

The retention times given are those obtained on a Beckmann HPLC-system using a YMC ODS-AM 4.6×250 mm-column and acetonitrile/water/0,1% TFA-gradient (0% acetonitrile to 80% acetonitrile in 40 min) under a flow of 1 ml/min. (unless stated otherwise).

Ex 22

2-HYDROXY-N-INDAN-2-YL-
4-METHYL-BENZAMIDE mp.: 163° C.

Ex 23

4-ETHOXY-2-HYDROXY-N-INDAN-
2-YL-BENZAMIDE mp.: 163° C.

Ex 24

3-FLUORO-N-INDAN-2-YL-BENZAMIDE

[M+H$^+$] measured: 256.2 retention-time: 15.48

Ex 25

3-ETHOXY-4-METHOXY-N-INDAN-2-YL-BENZAMIDE

[M+H$^+$] measured: 312.2 retention-time: 15.38

Ex 26

4-ETHOXY-N-INDAN-2-YL-BENZAMIDE

[M+H$^+$] measured: 282.2 retention-time: 16.62

Ex 27

4-CHLORO-3-METHYL-N-INDAN-2-YL-BENZAMIDE

[M+H$^+$] measured: 286.2 retention-time: 17.60

Ex 28

4-ISOPROPYLOXY-N-INDAN-2-YL-BENZAMIDE

[M+H$^+$] measured: 296.2 retention-time: 17.96

Ex 29

3,4-DIMETHYL-N-INDAN-2-YL-BENZAMIDE

[M+H$^+$] measured: 266.2 retention-time: 17.71

Ex 30

4-BUTOXY-N-INDAN-2-YL-BENZAMIDE

[M+H$^+$] measured: 310.2 retention-time: 20.83

Ex 31

3-CHLORO-4-METHOXY-N-INDAN-2-YL-BENZAMIDE

[M+H$^+$] measured: 302.2 retention-time: 17.27

Ex 32

4-PHENOXY-N-INDAN-2-YL-BENZAMIDE

[M+H$^+$] measured: 330.2 retention-time: 20.54

Ex 33

3-BROMO-4-FLUORO-N-INDAN-2-YL-BENZAMIDE

[M+H+] measured: 334.2 retention-time: 18.71

Ex 34

3-CHLORO-4-METHYL-N-INDAN-2-YL-BENZAMIDE

[M+H$^+$] measured: 286.2 retention-time: 19.23

Ex 35

3-FLUORO-4-METHOXY-N-INDAN-2-YL-BENZAMIDE

[M+H$^+$] measured: 286.2 retention-time: 15.75

Ex 36

3,4-DIMETHOXY-N-INDAN-2-YL-BENZAMIDE

[M+H$^+$] measured: 298.2 retention-time: 13.93

Ex 37

3-CHLORO-4-FLUORO-N-INDAN-2-YL-BENZAMIDE

[M+H$^+$] measured: 290.2 retention-time: 18.26

Ex 38

2,4-DIMETHYL-N-INDAN-2-YL-BENZAMIDE

[M+H$^+$] measured: 266.2 retention-time: 16.84

Ex 39

3,4-DIFLUOR-N-INDAN-2-YL-BENZAMIDE

[M+H$^+$] measured: 274.2 retention-time: 16.47

Ex 40

4-BENZYLOXY-N-INDAN-2-YL-BENZAMIDE

[M+M$^+$] measured: 344.2 retention-time: 20.38

Ex 41

5-BROMO-THIOPHEN-2-CARBOXYLIC ACID-INDAN-2-YLAMIDE

[M+H$^+$] measured: 322.2 retention-time: 18.14 M.P.: 158.5° C. IH-NMR (400 MHz, d6-DMSO): 2.90–2.98 (m, 2H, H-1/H-3), 3.21–3.29 (m, 2H, H-3/H-1), 4.63 (sext., 1H, H-2), 7.13–7.19 (m, 2H, H-4,H-7 or H-5, H-6), 7.22–7.28 (m 3H, H-4,H-7 or H-5, H-6 and H 3' or H4'), 7.64 (d, 1H,H 4' or H3'), 8.73 (d, 1H, NH)

Ex42

3-BENZYLOXY-4-METHOXY-N-INDAN-2-YL-BENZAMIDE

[M+H$^+$] measured: 374.2 retention-time: 19.62

Ex 43

4-FLUORO-NAPHTHALENE-1-CARBOXYLIC ACID-INDAN-2-YLAMIDE

[M+H$^+$] measured: 306.2 retention-time: 18.47

Ex 44

5-CHLORO-THIOPHEN-2-CARBOXYLIC ACID-INDAN-2-YLAMIDE

[M+H+] measured: 278.2 retention-time: 17.74

Ex 45

4-CHLORO-3-METHYL-N-INDAN-2-YL-BENZAMIDE

[M+H$^+$] measured: 286.2 retention-time: 19.14

Ex 46

4-CHLORO-3-METHOXY-N-INDAN-2-YL-BENZAMIDE

[M+H$^+$] measured: 302.2 retention-time: 18.42

Ex 47

3-METHOXY-4-METHYL-N-INDAN--YL-BENZAMIDE

[M+H$^+$] measured: 282.2 retention-time: 18.20

Ex 48

2-CHLORO-4,5-DIMETHOXY-N-INDAN-2-YL-BENZAMIDE

[M+H+] measured: 332.2 retention-time: 15.27

Ex 49

2-METHOXY-4-METHYL-N-INDAN-2-YL-BENZAMIDE

[M+H$^+$] measured: 282.2 retention-time: 18.10

Ex 50

4-TRIFLUOROMETHYLOXY-N-INDAN-2-YL-BENZAMIDE

[M+H$^+$] measured: 322.2 retention-time: 19.90

Ex 51

3-FLUORO-4-METHYL-N-INDAN-2-YL-BENZAMIDE

[M+H$^+$] measured: 270.2 retention-time: 18.09

Ex 52

4-METHOXY-3-METHYL-N-INDAN-2-YL-BENZAMIDE

[M+H$^+$] measured: 282.2 retention-time: 17.73

Ex 53

4-PROPYLOXY-N-INDAN-2-YL-BENZAMIDE

[M+H$^+$] measured: 296.2 retention-time: 19.60

Ex 54

3,4-DIETHOXY-N-INDAN-2-YL-BENZAMIDE

[M+H$^+$] measured: 326.2 retention-time: 17.67

Ex 55

4-(CYCLOHEX-2-ENYLOXY)-N-INDAN-2-YL-BENZAMIDE

[M+H$^+$] measured: 334.2 retention-time: 21.53

Ex 56

2,3-DIHYDRO-BENZOFURAN-5-CARBOXYLIC ACID INDAN-2-YLAMIDE

[M+H$^+$] measured: 280.2 retention-time: 15.67

Ex 57

4-FLUORO-2-TRIFLUOROMETHYL-N-INDAN-2-YL-BENZAMIDE

[M+H$^+$] measured: 324.2 retention-time: 16.54

Ex 58

3-FLUORO-2-METHYL-N-INDAN-2-YL-BENZAMIDE

[M+H$^+$] measured: 270.2 retention-time: 16.54

Ex 59

4-FLUORO-3-METHOXY-N-INDAN-2-YL-BENZAMIDE

[M+H$^+$] measured: 286.2 retention-time: 16.65

Ex 60

3,5-DIFLUORO-N-INDAN-2-YL-BENZAMIDE

[M+H$^+$] measured: 274.2 retention-time: 17.76

Ex 61

2-BROMO-4-FLUORO-N-INDAN-2-YL-BENZAMIDE

[M+H$^+$] measured: 334.2 retention-time: 16.73

Ex 62

4-FLUORO-3-TRIFLUORMETHYL-N-INDAN-2-YL-BENZAMIDE

[M+H$^+$] measured: 324.2 retention-time: 20.31

Ex 63

5-ACETYL-THIOPHEN-2-CARBOXYLIC ACID INDAN-2-YLAMIDE

[M+H$^+$] measured: 286.2 retention-time: 14.20

Ex 64

5-METHYL-THIOPHEN-2-CARBOXYLIC ACID INDAN-2-YLAMIDE

[M+H$^+$] measured: 258.2 retention-time: 15.67

Ex 65

2-CHLORO-4-FLUORO-N-INDAN-2-YL-BENZAMIDE

[M+H$^+$] measured: 290.2 retention-time: 15.70

Ex 66

2,2-DIFLUORO-BENZO[1,3]DIOXOL-5-CARBOXYLIC ACID INDAN-2-YLAMIDE

[M+H$^+$] measured: 318.2 retention-time: 18.73 MP. 147.5° C. 1H-NMR (400 MHz, d6-DMSO): 2.91–2.99 (m, 2H, H-1/H-3), 3.22–3.30 (m, 2H, H-3/H-1), 4.69 (sext., 1H, H-2), 7.13–7.19 (m, 2H, H-4,H-7 or H-5, H-6), 7.21–7.28 (m, 2H, H-4,H-7 or H-5, H-6), 7.50 (d, 1H, H-6'/H7'), 7.80 (d, 1H, H-7'/H6), 7.88 (s, 1H, H4'), 8.71(d, 1H, NH)

Ex 67

2-PHENOXY-N-INDAN-2-YL-BENZAMIDE

[M+H$^+$] measured: 330.2 retention-time: 20.77

Ex 68

2,4-DIFLUORO-N-INDAN-2-YL-BENZAMIDE

[M+H$^+$] measured: 274.2 retention-time: 15.93

Ex 69

4-CHLORO-N-INDAN-2-YL-BENZAMIDE

[M+H$^+$] measured: 272.2 retention-time: 17.00

Ex 70

4-CHLORO-2-HYDROXY-N-INDAN-2-YL-BENZAMIDE

[M+H$^+$] measured: 288.2 retention-time: 20.87

Ex 71

2-HYDROXY-N-INDAN-2-YL-BENZAMIDE

[M+H$^+$] measured: 254.1 retention-time: 17.15

Ex 72

N,N'-DI-INDAN-2-YL-PHTHALAMIDE

[M+H$^+$] measured: 397.2 Retention-time: 16.89

Ex 73

2-AMINO-N-INDAN-2-YL-BENZAMIDE

[M+H$^+$] measured: 253.1 retention-time: 19.26

Ex 74

2-(INDAN-2-YLAMINOCARBONYL)-BENZOIC ACID

[M+H$^+$] measured: 282.2 retention-time: 18.48

Ex 75

2-ACETYLAMINO-N-INDAN-2-YL-BENZAMIDE

[M+H$^+$] measured: 295.2 retention-time: 13.39

Ex 76

BENZO[1,3]DIOXOL-5-CARBOXYLIC ACID INDAN-2-YL AMIDE mp.: 175.4 ° C.
Method B:

To 0.75 mmol of the respective acid and 271 µl (1.575 mmole) diisopropylethylamine, (DIPEA) in 5 ml tetrahydrofuran were added 271 mg (0.825 mmol) O-[(cyano-ethoxycarbonylmethylene)-amino]-N,N,N',N'-tetramethyluronium tetrafluoroborate (TOTU) (dissolved in 1 ml DMF). After 15 min stirring at room temperature a mixture of 0.900 mmol of the respective amine hydrochloride and 172 µl (1.000 mmol) DIPEA in 1 ml DMF was added. After stirring for 6 h the mixture was filtered and evaporated. The residue was taken up in ethyl acetate and washed successively with 20 ml 1 n HCL and 20 ml 5% sodium hydrogen-carbonate solution. The resulting organic phase was evaporated and purified via prep. HPLC. (RP 18, acetonitrile/water).

The retention times given were obtained on a HPLC-MS-System (HP 1100, Detector: HP DAD G1315A) using a Merck Lichro CART 55-2 Purosphere STAR RP 18e 3µ, an acetonitrile/water+0.1% formic acid (B) gradient (95% B to 5% B in 1.25 min, 5% B for 3.5 min, 5% B bis 95% B in 0.25 min, and 95% B for 0.5 min under a flow of 0.75 ml/min

Ex 77

2,5-DIFLUORO-N-INDAN-2-YL-BENZAMIDE

[M+H$^+$] measured: 274 retention-time: 3.13

Ex 78

2,6-DIFLUORO-N-INDAN-2-YL-BENZAMIDE

[M+H$^+$] measured: 274 retention-time: 3.09

Ex 79

2-CHLORO-6-FLUORO-N-INDAN-2-YL-BENZAMIDE

[M+H$^+$] measured: 290 retention-time: 3.18

Ex 80

N-INDAN-2-YL-2-PHENYLAMINO-BENZAMIDE

[M+H$^+$] measured: 329 retention-time: 3.45

Ex 81

N-INDAN-2-YL-2,3-DIMETHOXY-BENZAMIDE

[M+H$^+$] measured: 298 retention-time: 3.17

Ex 82

N-INDAN-2-YL-2,3,4-TRIMETHOXY-BENZAMIDE

[M+H$^+$] measured: 328 retention-time: 3.32

Ex 83

N-INDAN-2-YL-2,4-DIMETHOXY-BENZAMIDE

[M+H$^+$] measured: 298 retention-time: 3.17

Ex 84

N-INDAN-2-YL-2,6-DIMETHOXY-BENZAMIDE

[M+H$^+$] measured: 298 retention-time: 3.01

Ex 85

2-ETHOXY-N-INDAN-2-YL-BENZAMIDE

[M+H$^+$] measured: 282 retention-time: 3.31

Ex 86

BIPHENYL-2-CARBOXYLIC ACID INDAN-2-YLAMIDE

[M+H$^+$] measured: 314 retention-time: 3.24

Ex 87

N-INDAN-2-YL-PHTHALAMIC ACID METHYL ESTER

[M+H$^+$] measured: 296 retention-time: 3.01

Ex 88

2-(4-FLUORO-BENZOYL)-N-INDAN-2-YL-BENZAMIDE

[M+H$^+$] measured: 360 retention-time: 3.29

Ex 89

2-ACETYL-N-INDAN-2-YL-BENZAMIDE

[M+H$^+$] measured: 280 retention-time: 3.10

Ex 90

N-INDAN-2-YL-2,3-DIMETHYL-BENZAMIDE

[M+H$^+$] measured: 266 retention-time: 3.18

Ex 91

N-INDAN-2-YL-2,6-DIMETHYL-BENZAMIDE

[M+H$^+$] measured: 266 retention-time: 3.20

Ex 92

2-BENZYL-N-INDAN-2-YL-BENZAMIDE

[M+H$^+$] measured: 328 retention-time: 3.28

Ex 93

N-INDAN-2-YL-2-(2-PHENETHYL)-BENZAMIDE

[M+H$^+$] measured: 342 retention-time: 3.36

Ex 94

3-BROMO-N-INDAN-2-YL-4-METHYL-BENZAMIDE

[M+H$^+$] measured: 331 retention-time: 3.32

Ex 95

N-INDAN-2-YL-3,4,5-TRIMETHOXY-BENZAMIDE

[M+H$^+$] measured: 328 retention-time: 3.10

Ex 96

N-INDAN-2-YL-3-TRIFLUOROMETHYL-BENZAMIDE

[M+H$^+$] measured: 306 retention-time: 3.27

Ex 97

4-CYANO-N-INDAN-2-YL-BENZAMIDE

[M+H$^+$] measured: 263 retention-time: 3.06

Ex 98

4-ACETYLAMINO-N-INDAN-2-YL-BENZAMIDE

[M+H$^+$] measured: 295 retention-time: 2.88

Ex 99

4-ETHYLSULFANYL-N-INDAN-2-YL-BENZAMIDE

[M+H$^+$] measured: 298 retention-time: 3.25

Ex 100

N-INDAN-2-YL-TEREPHTHALAMIC ACID METHYL ESTER

[M+H$^+$] measured: 296 retention-time: 3.12

Ex 101

4-BENZOYL-N-INDAN-2-YL-BENZAMIDE

[M+H$^+$] measured: 342 retention-time: 3.25

Ex 102

4-ACETYL-N-INDAN-2-YL-BENZAMIDE

[M+H$^+$] measured: 280 retention-time: 3.02

Ex 103

5-FLUORO-1H-INDOLE-2-CARBOXYLIC ACID INDAN-2-YLAMIDE

[M+H$^+$] measured: 295 retention-time: 3.14

Ex 104

1H-INDOLE-3-CARBOXYLIC ACID INDAN-2-YLAMIDE

[M+H$^+$] measured: 277 retention-time: 3.06

Ex 105

1H-INDOLE-5-CARBOXYLIC ACID INDAN-2-YLAMIDE

[M+H$^+$] measured: 277 retention-time: 3.05

Ex 106

1-METHYL-1H-INDOLE-2-CARBOXYLIC ACID INDAN-2-YLAMIDE

[M+H$^+$] measured: 291 retention-time: 3.29

Ex 107

PYRAZINE-2-CARBOXYLIC ACID INDAN-2-YLAMIDE

[M+H$^+$] measured: 240 retention-time: 2.92

Ex 108:

2-CHLORO-N-INDAN-2-YL-NICOTINAMIDE

[M+H$^+$] measured: 273 retention-time: 2.95

Ex 109

2-HYDROXY-N-INDAN-2-YL-6-METHYL-NICOTINAMIDE

[M+H$^+$] measured: 269 retention-time: 2.86

Ex 110

PYRIDINE-2-CARBOXYLIC ACID INDAN-2-YLAMIDE

[M+H$^+$] measured: 239 retention-time: 3.14

Ex 111

5-BUTYL-PYRIDINE-2-CARBOXYLIC ACID INDAN-2-YLAMIDE

[M+H$^+$] measured: 295 retention-time: 3.49

Ex 112:

2-PHENYL-QUINOLINE-4-CARBOXYLIC ACID INDAN-2-YLAMIDE

[M+H$^+$] measured: 365 retention-time: 3.40

Ex 113

QUINOLINE-2-CARBOXYLIC ACID INDAN-2-YLAMIDE

[M+H$^+$] measured: 289 retention-time: 3.30

Ex 114

QUINOLINE-4-CARBOXYLIC ACID INDAN-2-YLAMIDE

[M+H$^+$] measured: 289 retention-time: 2.98

Ex 115

N-INDAN-2-YL-4-METHANESULFONYL-BENZAMIDE

[M+H$^+$] measured: 316 retention-time: 2.99

Ex 116

N-INDAN-2-YL-4-SULFAMOYL-BENZAMIDE

[M+H$^+$] measured: 317 retention-time: 2.98

Ex 117

2-HYDROXY-N-INDAN-2-YL-NICOTINAMIDE

[M+H$^+$] measured: 255 retention-time: 2.80

Ex 118

N-INDAN-2-YL-2-METHOXY-4-METHYLSULFANYL-BENZAMIDE

[M+H$^+$] measured: 314 retention-time: 3.33

Ex 119

1H-BENZIMIDAZOLE-5-CARBOXYLIC ACID INDAN-2-YLAMIDE

[M+H$^+$] measured: 278 retention-time: 2.51

Ex 120

1H-BENZOTRIAZOLE-5-CARBOXYLIC ACID INDAN-2-YLAMIDE

[M+H$^+$] measured: 279 retention-time: 2.89

Ex 121

2,4,5-TRIFLUORO-N-INDAN-2-YL-BENZAMIDE

[M+H$^+$] measured: 292 retention-time: 3.21

Ex 122

N-INDAN-2-YL-N'-(S)-1-PHENYL-ETHYL)-PH-THALAMIDE

[M+H$^+$] measured: 385 retention-time: 3.13

Ex 123

N-INDAN-2-YL-2-(4-METHYL-BENZOYL)-BENZAMIDE

[M+H$^+$] measured: 356 retention-time: 3.29

Ex 124

3-(2-CHLORO-PHENYL)-5-METHYL-ISOXAZOLE-4-CARBOXYLIC ACID INDAN-2-YLAMIDE

[M+H$^+$] measured: 353 retention-time: 3.16

Ex 125

4-ACETYL-3,5-DIMETHYL-1H-PYRROLE-2-CARBOXYLIC ACID INDAN-2-YLAMIDE

[M+H$^+$] measured: 297 retention-time: 2.93

Ex 126

4-CYCLOHEXYL-N-INDAN-2-YL-BENZAMIDE

[M+H$^+$] measured: 320 retention-time: 3.48

Ex 127

4-BROMO-N-INDAN-2-YL-2-METHYL-BENZAMIDE

[M+H$^+$] measured: 330 retention-time: 3.21

Ex 128

N-INDAN-2-YL-3-TRIFLUOROMETHOXY-BENZAMIDE

[M+H$^+$] measured: 322 retention-time: 3.23

Ex 129

2,4,6-TRIFLUORO-N-INDAN-2-YL-BENZAMIDE

[M+H$^+$] measured: 292 retention-time: 3.01

Ex 130

4-CHLORO-2-FLUORO-N-INDAN-2-YL-BENZAMIDE

[M+H$^+$] measured: 290 retention-time: 3.21

Ex 131

N-INDAN-2-YL-PHTHAILAMIC ACID TERT-BUTYL ESTER

[M+H$^+$] measured: 281 (-tert.-butyl) retention-time: 3.14

Ex 132

3-CHLORO-THIOPHENE-2-CARBOXYLIC ACID INDAN-2-YLAMIDE

[M+H$^+$] measured: 278 retention-time: 3.25

Ex 133

N-INDAN-2-YL-2-PYRROL-1-YL-BENZAMIDE

[M+H$^+$] measured: 303 retention-time: 3.18

Ex 134

5-METHYL-2-PHENYL-2H-[1,2,3]TRIAZOLE-4-CARBOXYLIC ACID INDAN-2-YLAMIDE

[M+H$^+$] measured: 319 retention-time: 3.42

Ex 135

3,5-DIMETHYL-ISOXAZOLE-4-CARBOXYLIC ACID INDAN-2-YLAMIDE

[M+H$^+$] measured: 257 retention-time: 2.98

Ex 136

2-ETHYLSULFANYL-N-INDAN-2-YL-NICOTINAMIDE

[M+H$^+$] measured: 299 retention-time: 3.11

Ex 137

2-(2,3-DIMETHYL-PHENYLAMINO)-N-INDAN-2-YL-BENZAMIDE

[M+H$^+$] measured: 357 retention-time: 3.68

Ex 138

4-DIMETHYLAMINO-NAPHTHALENE-1-CARBOXYLIC ACID INDAN-2-YLAMIDE

[M+H$^+$] measured: 331 retention-time: 3.20

Ex 139

2-ACETYLAMINO-6-CHLORO-N-INDAN-2-YL-BENZAMIDE

[M+H$^+$] measured: 329 retention-time: 2.97

Ex 140

2-CHLORO-N-INDAN-2-YL-6-METHYL-ISONICOTINAMIDE

[M+H$^+$] measured: 287 retention-time: 3.11

Ex 141

5-CHLORO-6-HYDROXY-N-INDAN-2-YL-NICOTINAMIDE

[M+H$^+$] measured: 289 retention-time: 2.80

Ex 142

7-METHOXY-BENZOFURAN-2-CARBOXYLIC ACID INDAN-2-YLAMIDE

[M+H$^+$] measured: 308 retention-time: 3.20

Ex 143

2-FLUORO-N-INDAN-2-YL-5-TRIFLUOROMETHYL-BENZAMIDE

[M+H$^+$] measured: 324 retention-time: 3.29

Ex 144

5-METRYL-1-PHENYL-1H-PYRAZOLE-4-CARBOXYLIC ACID INDAN-2-YLAMIDE

[M+H$^+$] measured: 318 retention-time: 3.14

Ex 145

5-METHYL-PYRAZINE-2-CARBOXYLIC ACID INDAN-2-YLAMIDE

[M+H$^+$] measured: 254 retention-time: 2.97

Ex 146

2-(2-CYANO-PHENYLSULFANYL)-N-INDAN-2-YL-BENZAMIDE

[M+H$^+$] measured: 371 retention-time: 3.23

Ex 147

N-INDAN-2-YL-2,6-DIMETHOXY-NICOTINAMIDE

[M+H$^+$] measured: 299 retention-time: 3.23

Ex 148

2-CHLORO-4,5-DIFLUORO-N-INDAN-2-YL-BENZAMIDE

[M+H$^+$] measured: 308 retention-time: 3.20

Ex 149

N-INDAN-2-YL-4-PYRROL-1-YL-BENZAMIDE

[M+H$^+$] measured: 303 retention-time: 3.20

Ex 150

3,5-DI-TERT-BUTYL-N-INDAN-2-YL-BENZAMIDE

[M+H$^+$] measured: 351 retention-time: 3.62

Ex 151

2-CHLORO-N-INDAN-2-YL-6-METHYL-NICOTINAMIDE

[M+H$^+$] measured: 287 retention-time: 3.01

Ex 152

3-BENZOYL-PYRIDINE-2-CARBOXYLIC ACID INDAN-2-YLAMIDE

[M+H$^+$] measured: 343 retention-time: 3.21

Ex 153

1H-INDOLE-6-CARBOXYLIC ACID INDAN-2-YLAMIDE

[M+H$^+$] measured: 277 retention-time: 3.00

Ex 154

1H-INDAZOLE-3-CARBOXYLIC ACID INDAN-2-YLAMIDE

[M+H$^+$] measured: 278 retention-time: 3.02

Ex 155

5-(4-CHLORO-PHENYL)-FURAN-2-CARBOXYLIC ACID INDAN-2 YLAMIDE

[M+H$^+$] measured: 338 retention-time: 3.40

Ex 156

2,6-DICHLORO-N-INDAN-2-YL-ISONICOTINAMIDE

[M+H$^+$] measured: 307 retention-time: 3.22

Ex 157

N-INDAN-2-YL-4-METHYLAMINO-BENZAMIDE

[M+H$^+$] measured: 267 retention-time: 3.55

Ex 158

4-BUTYLAMINO-N-INDAN-2-YL-BENZAMIDE

[M+H$^+$] measured: 309 retention-time: 6.06

Ex 159

4-DIMETHYLAMINO-N-INDAN-2-YL-BENZAMIDE

[M+H$^+$] measured: 281 retention-time: 5.44

Ex 160

BIPHENYL-4-CARBOXYLIC ACID INDAN-2-YLAMIDE

[M+H$^+$] measured: 314 retention-time: 3.94

Ex 161

N-INDAN-2-YL-4-TRIFLUOROMETHYL-BENZAMIDE

[M+H$^+$] measured: 306 retention-time: 3.36

Ex 162

4-ETHYL-N-INDAN-2-YL-BENZAMIDE

[M+H$^+$] measured: 266 retention-time: 3.19

Ex 163

1-METHYL-IH-PYRROLE-2-CARBOXYLIC ACID INDAN-2-YLAMIDE

[M+H$^+$] measured: 241 retention-time: 3.00

Ex 164

5-BROMO-FURAN-2-CARBOXYLIC ACID INDAN-2-YLAMIDE

[M+H$^+$] measured: 306 retention-time: 3.08

Ex 165

2-ETHOXY-NAPHTHALENE-1-CARBOXYLIC ACID INDAN-2-YLAMIDE

[M+H$^+$] measured: 332 retention-time: 3.19

Ex 166

1H-PYRROLE-2-CARBOXYLIC ACID INDAN-2-YLAMIDE

[M+H$^+$] measured: 227 retention-time: 2.88

Ex 167

3-METHYL-THIOPHENE-2-CARBOXYLIC ACID INDAN-2-YLAMIDE

[M+H$^+$] measured: 258 retention-time: 3.08

Ex 168

THIOPHENE-3-CARBOXYLIC ACID INDAN-2-YLAMIDE

[M+H$^+$] measured: 244 retention-time: 2.96

Ex 169

N-INDAN-2-YL-1-OXY-ISONICOTINAMIDE

[M+H$^+$] measured: 255 retention-time: 2.51

Ex 170

6-HYDROXY-N-INDAN-2-YL-NICOTINAMIDE

[M+H$^+$] measured: 255 retention-time: 2.60

Ex 171

2-AMINO-N-INDAN-2-YL-NICOTINAMIDE

[M+H$^+$] measured: 254 retention-time: 1.55

Ex 172

6-AMINO-N-INDAN-2-YL-NICOTINAMIDE

[M+H$^+$] measured: 254 retention-time: 1.62

Ex 173

N-INDAN-2-YL-6-METHYL-NICOTINAMIDE

[M+H$^+$] measured: 253 retention-time: 2.43

Ex 174

N-INDAN-2-YL,-NICOTINAMIDE

[M+H$^+$] measured: 239 retention-time: 2.63

Ex 175

N-INDAN-2-YL-ISONICOTINAMIDE

[M+H$^+$] measured: 239 retention-time: 2.56

Ex 176

N-INDAN-2-YL-2-METHYL-NICOTINAMIDE

[M+H$^+$] measured: 253 retention-time: 1.59

Ex 177

3-ACETYLAMINO-N-INDAN-2-YL-BENZAMIDE

[M+H$^+$] measured: 295 retention-time: 2.83

Ex 178

N-INDAN-2-YL-4-PENTYLOXY-BENZAMIDE

[M+H$^+$] measured: 324 retention-time: 3.41

Ex 179

N-INDAN-2-YL-4-PROPYL-BENZAMIDE

[M+H$^+$] measured: 280 retention-time: 3.28

Ex 180

3-CHLORO-BENZO[BITHIOPHENE-2-CARBOXYLIC ACID INDAN-2-YLAMIDE

[M+H$^+$] measured: 328 retention-time: 3.44

Ex 181

N-INDAN-2-YL-2-PHENOXY-NICOTINAMIDE

[M+H$^+$] measured: 331 retention-time: 3.20

Ex 182

2-DIMETHYLAMINO-N-INDAN-2-YL-BENZAMIDE

[M+H$^+$] measured: 281 retention-time: 2.86

Ex 183

N-INDAN-2-YL-2,4,6-TRIMETHOXY-BENZAMIDE

[M+H$^+$] measured: 328 retention-time: 2.98

Ex 184

N-INDAN-2-YL-4-(2,2,2-TRIFLUORO-1,1-DIHYDROXY-ETHYL)-BENZAMIDE

[M+H$^+$] measured: 352 retention-time: 3.01

Ex 185

3-AMINO-PYRAZINE-2-CARBOXYLIC ACID INDAN-2-YLAMIDE

[M+H$^+$] measured: 255 retention-time: 4.71 condition: a

Ex 186

4-METHYL-2-PHENYL-THIAZOLE-5-CARBOXYLIC ACID INDAN-2-YLAMIDE

[M+H$^+$] measured: 335 retention-time: 5.32 condition: a

Ex 187

2-AMINO-N-INDAN-2-YL-4,6-DIMETRYL-NICOTINAMIDE

[M+H$^+$] measured: 282 retention-time: 3.85 condition: a

Ex 188

6-CYANO-N-INDAN-2-YL-NICOTINAMIDE

[M+H$^+$] measured: 264 retention-time: 4.31 condition: a

Ex 189

N-INDAN-2-YL-4,6-DIMETHYL-NICOTINAMIDE

[M+H$^+$] measured: 267 retention-time: 3.43 condition: a

Ex 190

N-INDAN-2-YL-1-OXY-NICOTINAMIDE

[M+H$^+$] measured: 255 retention-time: 1.44 condition: c

Ex 191

QUINOLINE-3-CARBOXYLIC ACID INDAN-2-YLAMIDE

[M+H$^+$] measured: 289 retention-time: 1.71 condition: c

Ex 192

CINNOLINE-4-CARBOXYLIC ACID INDAN-2-YLAMIDE

[M+H$^+$] measured: 290 retention-time: 1.64 condition: c

Ex 193

5-BROMO-N-INDAN-2-YL-NICOTINAMIDE

[M+H$^+$] measured: 317 retention-time: 1.74 condition: c

Ex 194

N-INDAN-2-YL-2-METHYLSULFANYL-NICOTINAMIDE

[M+H$^+$] measured: 285 retention-time: 1.68 condition: c

Ex 195

N-INDAN-2-YL-2-MERCAPTO-NICOTINAMIDE

[M+H$^+$] measured: 271

Ex 196

1H-PYRAZOLE-4-CARBOXYLIC ACID INDAN-2-YLAMIDE

[M+H$^+$] measured: 228 retention-time: 1.54 condition: c

Ex 197

QUINOXALINE-2-CARBOXYLIC ACID INDAN-2-YLAMIDE

[M+H$^+$] measured: 290 retention-time: 1.82 condition: c

Ex 198

[1,2,3]THIADIAZOLE-4-CARBOXYLIC ACID INDAN-2-YLAMIDE

[M+H$^+$] measured: 246 retention-time: 1.70 condition: c

Ex 199

N-INDAN-2-YL-2-P-TOLYLSULFANYL-NICOTINAMIDE

[M+H$^+$] measured: 361 retention-time: 1.87 condition: c

Ex 200

5-METHYL-1-(3-TRIFLUOROMETHYL-PHENYL)-IH-[1,2,3]TRIAZOLE-4-CARBOXYLIC ACID INDAN-2-YLAMIDE

[M+H$^+$] measured: 387 retention-time: 1.93 condition: c

Ex 201

4-PHENYL-[1,2,3]THIADIAZOLE-5-CARBOXYLIC ACID INDAN-2YLAMIDE

[M+H$^+$] measured: 322 retention-time: 1.84 condition: c

Ex 202

5,6-DICHLORO-N-INDAN-2-YL-NICOTINAMIDE

[M+H⁺] measured: 307 retention-time: 1.73 condition: c

Ex 203

2,6-DICHLORO-N-INDAN-2-YL-NICOTINAMIDE

[M+H⁺] measured: 307 retention-time: 1.61 condition: c

Ex 204

1H-IMIDAZOLE-4-CARBOXYLIC ACID INDAN-2-YLAMIDE

[M+H⁺] measured: 288 retention-time: 0.62 condition: c

Ex 205

N-INDAN-2-YL-4-TRIFLUOROMETHYL-NICOTINAMIDE

[M+H⁺] measured: 307 retention-time: 1.57 condition: c

Ex 206

N-INDAN-2-YL-2-METHOXY-NICOTINAMIDE

[M+H⁺] measured: 269 retention-time: 1.64 condition: c

Ex 207

5-METHYL-1H-PYRAZOLE-3-CARBOXYLIC ACID INDAN-2-YLAMIDE

[M+H⁺] measured: 242 retention-time: 1.47 condition: c

Ex 208:

4-METHYL-2-PYRAZIN-2-YL-THIAZOLE-5-CARBOXYLIC ACID INDAN-2-YLAMIDE

[M+H⁺] measured: 337 retention-time: 1.65 condition: c

Ex 209

5-METHYL-1-PHENYL-1H-PYRAZOLE-3-CARBOXYLIC ACID INDAN-2-YLAMIDE

[M+H⁺] measured: 318 retention-time: 1.75 condition: c

Ex 210

2-ETHYL-5-METHYL-2H-PYRAZOLE-3-CARBOXYLIC ACID INDAN-2-YLAMIDE

[M+H⁺] measured: 270 retention-time: 1.62 conditions: c

Ex 211

2,5-DIMETHYL-2H-PYRAZOLE-3-CARBOXYLIC ACID INDAN-2-YLAMIDE

[M+H⁺] measured: 256 retention-time: 1.64 condition: c

Ex 212

4-METHYL-[1,2,3]THIADIAZOLE-5-CARBOXYLIC ACID INDAN-2-YLAMIDE

[M+H⁺] measured: 260 retention-time: 1.60 condition: c

Ex 213

N-INDAN-2-YL-5-PHENYLETHYNYL-NICOTINAMIDE

[M+H⁺] measured: 339 retention-time: 1.90 condition: c

Ex 214

3-PHENYL-3H-[1,2,3]TRIAZOLE-4-CARBOXYLIC ACID INDAN-2 YLAMIDE

[M+H⁺] measured: 305

Ex 215

N-INDAN-2-YL-6-MERCAPTO-NICOTINAMIDE

[M+H⁺] measured: 271 retention-time: 1.59 condition: c

Ex 216

2,5-DIMETHYL-1H-PYRROLE-3-CARBOXYLIC ACID INDAN-2-YLAMIDE

[M+H⁺] measured: 255 retention-time: 1.64 condition: c

Ex 217

3-METHYL-5-TRIFLUOROMETHYL-ISOXAZOLE-4-CARBOXYLIC ACID INDAN-2-YLAMIDE

[M+H⁺] measured: 311 retention-time: 1.80 condition: c

Ex 218

2-METHYL-IMIDAZO[1,2-]PYRIDINE-3-CARBOXYLIC ACID INDAN-2-YLAMIDE

[M+H⁺] measured: 292 retention-time: 1.42 condition: c

Ex 219

2,6-DICHLORO-5-FLUORO-N-INDAN-2-YL-NICOTINAMIDE

[M+H⁺] mesured: 325 retention-time: 1.81 condition: c

Ex 220

1H-PYRROLE-3-CARBOXYLIC ACID INDAN-2-YLAMIDE

[M+H⁺] measured: 227 retention-time: 0.87 condition: c

Ex 221

N-INDAN-2-YL-5-METHYL-NICOTINAMIDE

[M+H$^+$] measured: 253 retention-time: 1.53 condition: c

Ex 222

5-HEX-1-YNYL-N-INDAN-2-YL-NICOTINAMIDE

[M+H$^+$] measured: 319 retention-time: 1.91 condition: c

Ex 223

5-METHYL-2-(4-METHYL-BENZYL)-2H-PYRAZOLE-3-CARBOXYLIC ACID INDAN-2-YLAMIDE

[M+H$^+$] measured: 346 retention-time: 1.91 condition: c

Ex 224

5-METHYL-1-(4-METHYL-BENZYL)-1H-PYRAZOLE-3-CARBOXYLIC ACID INDAN-2-YLAMIDE

[M+H$^+$] measured: 346 retention-time: 1.93 condition: c

Ex 225

2-(4-FLUORO-PHENOXY)-N-INDAN-2-YL-NICOTINAMIDE

[M+H$^+$] measured: 349 retention-time: 1.92 condition: c

Ex 226

5-METHYL-ISOXAZOLE-4-CARBOXYLIC ACID INDAN-2-YLAMIDE

[M+H$^+$] measured: 243 retention-time: 1.69 condition: c

Ex 227

3-METHYL-ISOXAZOLE-4-CARBOXYLIC ACID INDAN-2-YLAMIDE

[M+H$^+$] measured: 243 retention-time: 1.68 condition: c

Ex 228

1-METHYL-1H-INDOLE-3-CARBOXYLIC ACID INDAN-2-YLAMIDE

[M+H$^+$] measured: 291 retention-time: 1.79 condition: c

Ex 229

N-INDAN-2-YL-6-(2,2,2-TRIFLUORO-ETHOXY)-4-TRIFLUOROMETHYL-NICOTINAMIDE

[M+H$^+$] measured: 405 retention-time: 1.93 condition: c

Ex 230

2,5-DIMETHYL-1-PYRIDIN-4-YLMETHYL-1H-PYRROLE-3-CARBOXYLIC ACID INDAN-2-YLAMIDE

[M+H$^+$] measured: 346 retention-time: 1.52 condition: c

Ex 231

N-INDAN-2-YL-2-METHOXY-4,6-DIMETHYL-NICOTINAMIDE

[M+H$^+$] measured: 297 retention-time: 1.65 condition: c

Ex 232

5-METHYL-3-PHENYL-ISOXAZOLE-4-CARBOXYLIC ACID INDAN-2-YLAMIDE

[M+H$^+$] measured: 319 retention-time: 1.83 condition: c

Ex 233

2,4-DIMETHYL-THIAZOLE-5-CARBOXYLIC ACID INDAN-2-YLAMIDE

[M+H$^+$] measured: 273 retention-time: 4.18 condition: a

Ex 234

2-METHYL-4-TRIFLUOROMETHYL-THIAZOLE-5-CARBOXYLIC ACID INDAN-2-YLAMIDE

[M+H$^+$] measured: 327 retention-time: 4.61 condition: a

Ex 235

5-TRIFLUOROMETHYL-THIENO[3,2-B]PYRIDINE-6-CARBOXYLIC ACID INDAN-2-YLAMIDE

[M+H$^+$] measured: 363 retention-time: 4.69 condition: a

Ex 236

N-INDAN-2-YL-6-TRIFLUOROMETHYL-NICOTINAMIDE

[M+H$^+$] measured: 307 retention-time: 4.67 condition: a

Ex 237

N-INDAN-2-YL-2-METHYL-6-TRIFLUOROMETHYL-NICOTINAMIDE

[M+H$^+$] measured: 321 retention-time: 4.67 condition: a

Ex 238

4'-PROPYL-BIPHENYL-4-CARBOXYLIC ACID INDAN-2-YLAMIDE

[M+H$^+$] measured: 356 retention-time: 3.54 condition: c

Ex 239

3,5-DIBROMO-N-INDAN-2-YL-4-METHYL-BENZAMIDE

[M+H⁺] measured: 408 retention-time: 3.50 condition: c

Ex 240

3-BROMO-N-INDAN-2-YL-4-METHOXY-BENZAMIDE

[M+H⁺] measured: 346 retention-time: 3.09 condition: c

Ex 241

5-BROMO-1H-INDOLE-2-CARBOXYLIC ACID INDAN-2YLAMIDE

[M+H⁺] measured: 355 retention-time: 3.18 condition: c

Ex 242

4-(1,3-DIOXO-1,3-DIHYDRO-ISOINDOL-2-YL)-N-INDAN-2-YL-BENZAMIDE

[M+H⁺] measured: 383

Ex 243

N-INDAN-2-YL-ISOPHTHALAMIC ACID METHYL ESTER

[M+H⁺] measured: 296 retention-time: 3.01 condition: c

Ex 244

4,5-DIBROMO-THIOPHENE-2-CARBOXYLIC ACID INDAN-2-YLAMIDE

[M+H⁺] measured: 400 retention-time: 3.31 condition: c

Ex 245

2-(2,6-DIFLUORO-PHENYL)-N-INDAN-2-YL-ACETAMIDE

[M+H⁺] measured: 288 retention-time: 3.02 condition: c

Ex 246

N-INDAN-2-YL-4-TRIFLUOROMETHYLSULFANYL-BENZAMIDE

[M+H⁺] measured: 338 retention-time: 3.25 condition: c

Ex 247

2-FLUORO-N-INDAN-2-YL-3-TRIFLUOROMETHYL-BENZAMIDE

[M+H⁺] measured: 324 retention-time: 3.16 condition: c

Ex 248

5-FLUORO-N-INDAN-2-YL-2-METHYL-BENZAMIDE

[M+H⁺] measured: 270 retention-time: 3.04 condition: c

Ex 249

2-FLUORO-N-INDAN-2-YL-3-METHYL-BENZAMIDE

[M+H⁺] measured: 270 retention-time: 3.10 condition: c

Ex 250

3-CHLORO-2-FLUORO-N-INDAN-2-YL-BENZAMIDE

[M+H⁺] measured: 290 retention-time: 3.10 condition: c

Ex 251

3-METHYL-1H-INDENE-2-CARBOXYLIC ACID INDAN-2-YLAMIDE

[M+H⁺] measured: 290 retention-time: 3.15 condition: c

Ex 252

7-NITRO-1H-INDOLE-2-CARBOXYLIC ACID INDAN-2-YLAMIDE

[M+H⁺] measured: 322 retention-time: 3.10 condition: c

Ex 253

3-BROMO-N-INDAN-2-YL-2-METHOXY-BENZAMIDE

[M+H⁺] measured: 346 retention-time: 3.07 condition: c

Ex 254

5-METHYL-1H-INDOLE-2-CARBOXYLIC ACID INDAN-2-YLAMIDE

[M+H⁺] measured: 291 retention-time: 3.11 condition: c

Ex 255

7-METHYL-1H-INDOLE-2-CARBOXYLIC ACID INDAN-2-YLAMIDE

[M+H⁺] measured: 291 retention-time: 3.11 condition: c

Ex 256

N-INDAN-2-YL-4-(2,2,2-TRIFLUORO-ACETYL)-BENZAMIDE

[M+H⁺] measured: 334 retention-time: 2.88 condition: c

Ex 257

3-CHLORO-N-INDAN-2-yl-2-METHYL-BENZAMIDE

[M+H$^+$] measured: 286 retention-time: 3.09 condition: c

Ex 258

N-INDAN-2-yl-2,4,6-TRIISOPROPYL-BENZAMIDE

[M+H$^+$] measured: 365

Ex 259

2,3,5-TRICHLORO-N-INDAN-2-YL-BENZAMIDE

[M+H$^+$] measured: 340 retention-time: 3.21 condition: c

Ex 260

5-ETHYL-1H-INDOLE-2-CARBOCXYLIC ACID INDAN-2-YLAMIDE

[M+H$^+$] measured: 305 retention-time: 3.18 condition: c

Ex 261

1-PHENYL-5-PROPYL-1H-PYRAZOLE-4-CARBOXYLIC ACID INDAN-2-YLAMIDE

[M+H$^+$] measured: 346 retention-time: 3.13 condition: c

Ex 262

2,4-DICHLORO-5-FLUORO-N-INDAN-2-YL-BENZAMIDE

[M+H$^+$] measured: 324 retention-time: 3.13 condition: c

Ex 263

4-CHLORO-2,5-DIFLUORO-N-INDAN-2-YL-BENZAMIDE

[M+H$^+$] measured: 308 retention-time: 3.17 condition: c

Ex 264

2-CHLORO-N-INDAN-2-YL-3-METHYL-BENZAMIDE

[M+H$^+$] measured: 286 retention-time: 1.95 condition: c

Ex 265

3-CHLORO-4-(PROPANE-2-SULFONYL)-THIOPHENE-2-CARBOXYLIC ACID INDAN-2-YLAMIDE

[M+H$^+$] measured: 385 retention-time: 3.04 condition: c

Ex 266

2-FLUORO-N-INDAN-2-YL-5-METHYL-BENZAMIDE

[M+H$^+$] measured: 270 retention-time: 3.08 condition: c

Ex 267

3-ACETYLAMINO-2-CHLORO-N-INDAN-2-YL-BENZAMIDE

[M+H$^+$] measured: 329 retention-time: 2.75 condition: c

Ex 268

4-ETHYLAMINO-N-INDAN-2-YL-BENZAMIDE

[M+H$^+$] measured: 281 retention-time: 2.94 condition: c

Ex 269:

N,N-DIETHYL-3,6-DIFLUORO-N'-INDAN-2-YL-PHTHALAMIDE

[M+H$^+$] measured: 373 retention-time: 2.98 condition: c

Ex 270

ACRIDINE-9-CARBOXYLOC ACID INDAN-2-YLAMIDE

[M+H$^+$] measured: 339 retention-time: 2.87 condition: c

Ex 271

9-OXO-9H-FLUORENE-4-CARBOXYLIC ACID INDAN-2 YLAMIDE

[M+H$^+$] measured: 340 retention-time: 3.09 condition: c

Ex 272

2-BROMO-N-INDAN-2-YL-BENZAMIDE

[M+H$^+$] measured: 316 retention-time: 2.98 condition: c

Ex 273

2-FLUORO-N-INDAN-2-YL-BENZAMIDE

[M+H$^+$] measured: 256 retention-time: 3.00 condition: c

Ex 274

2,3,6-TRIFLUORO-N-INDAN-2-YL-BENZAMIDE

[M+H$^+$] measured: 292 retention-time: 2.99 condition: c

Ex 275

2-CHLORO-N-INDAN-2-YL-BENZAMIDE

[M+H$^+$] measured: 272 retention-time: 2.97 condition: c

Ex 276

2,3-DICHLORO-N-INDAN-2-YL-BENZAMIDE

[M+H$^+$] measured: 306 retention-time: 3.11 condition: c

Ex 277

2,4-DICHLORO-N-INDAN-2-YL-BENZAMIDE

[M+H$^+$] measured: 306 retention-time: 3.07 condition: c

Ex 278

5-BROMO-2-CHLORO-N-INDAN-2-YL-BENZAMIDE

[M+H$^+$] measured: 351 retention-time: 3.12 condition: c

Ex 279

2,5-DICHLORO-N-INDAN-2-YL-BENZAMIDE

[M+H$^+$] measured: 306 retention-time: 3.11 condition: c

Ex 280

2,6-DICHLORO-N-INDAN-2-YL-BENZAMIDE

[M+H$^+$] measured: 306 retention-time: 3.04 condition: c

Ex 281

N-INDAN-2-YL-2-METHYL-BENZAMIDE

[M+H$^+$] measured: 252 retention-time: 2.97 condition: c

Ex 282

N-INDAN-2-YL-2,4,6-TRIMETHYL-BENZAMIDE

[M+H$^+$] measured: 280 retention-time: 3.09 condition: c

Ex 283

3-CHLORO-N-INDAN-2-YL-BENZAMIDE

[M+H$^+$] measured: 272 retention-time: 3.08 condition: c

Ex 284

3-CYANO-N-INDAN-2-YL-BENZAMIDE

[M+H$^+$] measured: 263 retention-time: 2.94 condition: c

Ex 285

3,5-DICHLORO-N-INDAN-2-YL-BENZAMIDE

[M+H$^+$] measured: 306 retention-time: 3.28 condition: c

Ex 286

N-INDAN-2-YL-3-PHENOXY-BENZAMIDE

[M+H$^+$] measured: 330 retention-time: 3.23 condition: c

Ex 287

3-BENZOYL-N-INDAN-2-YL-BENZAMIDE

[M+H$^+$] measured: 342 retention-time: 3.12 condition: c

Ex 288

N-INDAN-2-YL-3-METHYL-BENZAMIDE

[M+H$^+$] measured: 252 retention-time: 3.02 condition: c

Ex 289

4-BROMO-N-INDAN-2-YL-BENZAMIDE

[M+H$^+$] measured: 316 retention-time: 3.09 condition: c

Ex 290

4-DIETHYLAMINO-N-INDAN-2-YL-BENZAMIDE

[M+H$^+$] measured: 309 retention-time: 3.03 condition: c

Ex 291

N-INDAN-2-YL-4-METHOXY-BENZAMIDE

[M+H$^+$] measured: 268 retention-time: 2.96 retention time: c

Ex 292

N-INDAN-2-YL-4-METHYSULFANYL-BENZAMIDE

[M+H$^+$] measured: 284 retention-time: 3.04 condition: c

Ex 293

N-INDAN-2-YL-4-PENTYL-BENZAMIDE

[M+H$^+$] measured: 308 retention-time: 3.41 condition: c

Ex 294

NAPHTHALENE-1-CARBOXYLIC ACID INDAN-2-YLAMIDE

[M+H$^+$] measured: 288 retention-time: 3.09 condition: c

Ex 295

NAPHTHALENE-2-CARBOXYLIC ACID INDAN-2-YLAMIDE

[M+H$^+$] measured: 288 retention-time: 3.22 condition: c

Ex 296

FURAN-3-CARBOXYLIC ACID INDAN-2-YLAMIDE

[M+H$^+$] measured: 228 retention-time: 2.84 condition: c

Ex 297

THIOPHENE-2-CARBOXYLIC ACID INDAN-2-YLAMIDE

[M+H$^+$] measured: 244 retention-time: 2.94 condition: c

Ex 298

5-METHOXY-1H-INDOLE-2-CARBOXYLIC ACID INDAN-2-YLAMIDE

[M+H$^+$] measured: 307 retention-time: 3.00 condition: c

Ex 299

4-HYDROXY-7-TRIFLUOROMETRYL-QUINOLINE-3-CARBOXYLIC ACID INDAN-2-YLAMIDE

[M+H$^+$] measured: 373 retention-time: 3.07 condition: c

Ex 300

2-CHLORO-N-INDAN-2-YL-5-METHYLSULFANYL-BENZAMIDE

[M+H$^+$] measured: 318 retention-time: 3.09 condition: c

Ex 301

4'-ETHYL-BIPHENYL-4-CARBOXYLIC ACID INDAN-2-YLAMIDE

[M+H$^+$] measured: 342 retention-time: 3.41 condition: c

Ex 302

2,3-DIFLUORO-N-INDAN-2-YL-BENZAMIDE

[M+H$^+$] measured: 274 retention-time: 3.03 condition: c

Ex 303

N-INDAN-2-YL-2-(3-TRIFLUOROMETHYL-PHENYLAMINO)-NICOTINAMIDE

[M+H$^+$] measured: 398 retention-time: 3.54 condition: c

Ex 304

2-BROMO-5-CHLORO-N-INDAN-2-YL-BENZAMIDE

[M+H$^+$] measured: 350 retention-time: 3.10 condition: c

Ex 305

4-HEXYLOXY-N-INDAN-2-YL-BENZAMIDE

[M+H$^+$] measured: 338 retention-time: 3.45 condition: c

Ex 306

3-ETHOXY-N-INDAN-2-YL-BENZAMIDE

[M+H$^+$] measured: 282 retention-time: 3.06 condition: c

Ex 307

N-INDAN-2-YL-4-METHYLSUFANYL-3-NITRO-BENZAMIDE

[M+H$^+$] measured: 329 retention-time: 3.15 condition: c

Ex 308

4-HYDROXY-QUINOLINE-2-CARBOXYLIC ACID INDAN-2-YLAMIDE

[M+H$^+$] measured: 305 retention-time: 2.81 condition: c

Ex 309

4-(4,6-DIMETHYL-PYRIMIDIN-2-YLAMINO)-N-INDAN-2-YL-BENZAMIDE

[M+H$^+$] measured: 359 retention-time: 3.03 condition: c

Ex 310

4-[(4,6-DIMETHYL-PYRIMIDIN-2-YL)-METHYL-AMINO]-N-INDAN-2-YL-BENZAMIDE

[M+H$^+$] measured: 373 retention-time: 3.07 condition: c

Ex 311

4,6-DICHLORO-1H-INDOLE-2-CARBOXYLIC ACID INDAN-2-YLAMIDE

[M+H$^+$] measured: 345 retention-time: 3.30 condition: c

Ex 312

2-CHLORO-N-INDAN-2-YL-4-METHANESYLFONYL-BENZAMIDE

[M+H$^+$] measured: 350 retention-time: 2.88 condition: c

Ex 313

2-METHYL-1-PHENYL-1H-BENZOIMIDAZOLE-5-CARBOXYLIC ACID INDAN-2-YLAMIDE

[M+H$^+$] measured: 368 retention-time: 2.86 condition: c

Ex 314

3,4-DICHLORO-N-INDAN-2-YL-BENZAMIDE

[M+H$^+$] measured: 306 retention-time: 3.20 condition: c

Ex 315

5-CHLORO-1H-INDOLE-2-CARBOXYLIC ACID INDAN-2-YLAMIDE

[M+H$^+$] measured: 311 retention-time: 3.14 condition: c

Ex 316

2,5-DIBROMO-N-INDAN-2-YL-BENZAMIDE

[M+H$^+$] measured: 394 retention-time: 3.13 condition: c

Ex 317

4-BROMO-2-CHLORO-N-INDAN-2-YL-BENZAMIDE

[M+H$^+$] measured: 350 retention-time: 3.12 condition: c

Ex 318

5-BENZYLOXY-1H-INDOLE-2-CARBOXYLIC ACID INDAN-2-YLAMIDE

[M+H$^+$] measured: 383 retention-time: 3.23 condition: c

Ex 319

3-METHYL-BENZOFURAN-2-CARBOXYLIC ACID INDAN-2-YLAMIDE

[M+H$^+$] measured: 292 retention-time: 3.25 condition: c

Ex 320

2,3,4-TRIFLUORO-N-INDAN-2-YL-BENZAMIDE

[M+H$^+$] measured: 292 retention-time: 3.07 condition: c

Ex 321

3-CHLORO-4-METHANESULFONYL-THIOPHENE-2-CARBOXYLIC ACID INDAN-2-YLAMIDE

[M+H$^+$] measured: 356 retention-time: 2.92 condition: c

Ex 322

1-(4-CHLORO-PHENYL)-5-PROPYL-1H-PYRAZOLE-4-CARBOXYLIC ACID INDAN-2-YLAMIDE

[M+H$^+$] measured: 381 retention-time: 3.27 condition: c

Ex 323

4-DIHEXYLAMINO-N-INDAN-2-YL-BENZAMIDE

[M+H$^+$] measured: 422 retention-time: 4.26 condition: c

Ex 324

3-CHLORO-6-FLUORO-BENZO[B]THIOPHENE-2-CARBOXYLIC ACID INDAN-2-YLAMIDE

[M+H$^+$] measured: 346 retention-time: 3.40 condition: c

Ex 325

2,6-DIBROMO-N-INDAN-2-YL-BENZAMIDE

[M+H$^+$] measured: 394 retention-time: 3.06 condition: c

Ex 326

5-(INDAN-2-YLCARBAMOYL)-ISOPHTHALIC ACID DIETHYL ESTER

[M+H$^+$] measured: 382 retention-time: 3.22 condition: c

Ex 327

4-(2,5-DIMETHYL-PYRROL-1-YL)-N-INDAN-2-YL-BENZAMIDE

[M+H$^+$] measured: 331 retention-time: 3.21 condition: c

Ex 328

4-IMIDAZOL-1-YL-N-INDAN-2-YL-BENZAMIDE

[M+H$^+$] measured: 304 retention-time: 2.37 condition: c

Ex 329

3,4-DICHLORO-BENZO[B]THIOPHENE-2-CARBOXYLIC ACID INDAN-2-YLAMIDE

[M+H$^+$] measured: 362 retention-time: 3.49 condition: c

Ex 330

5-CHLORO-2-FLUORO-N-INDAN-2-YL-BENZAMIDE

[M+H$^+$] measured: 291 retention-time: 3.12 condition: c

Ex 331

2-BROMO-4-CHLORO-N-INDAN-2-YL-BENZAMIDE

[M+H$^+$] measured: 350 retention-time: 3.12 condition: c

Ex 332

3-CHLORO-6-METHYL-BENZO[B]THIOPHENE-2-CARBOXYLIC ACID INDAN-2-YLAMIDE

[M+H$^+$] measured: 342 retention-time: 3.52 condition: c

Ex 333

5-CHLORO-7-TRIFLUOROMETHYL-THIENO[3,2-B]PYRIDINE-3-CARBOXYLIC ACID INDAN-2-YLAMIDE

[M+H$^+$] measured: 397 retention-time: 3.49 condition: c

Ex 334

3,6-DICHLORO-BENZO[B]THIOPHENE-2-CARBOXYLIC ACID INDAN-2-YLAMIDE

[M+H$^+$] measured: 362 retention-time: 3.56 condition: c

Ex 335

1,1-DINETHYL-INDAN-4-CARROXYLIC ACID INDAN-2-YLAMIDE

[M+H$^+$] measured: 306 retention-time: 3.27 condition: c

Ex 336

1-(3-FLUORO-PHENYL)-CYCLOPENTANECARBOXYLIC ACID INDAN-2-YLAMIDE

[M+H$^+$] measured: 324 retention-time: 3.26 condition: c

Ex 337

2-(2-FLUORO-BIPHENYL-4-YL)-N-INDAN-2-YL-PROPIONAMIDE

[M+H$^+$] measured: 360 retention-time: 3.27 condition: c

Ex 338

3-PHENYL-6-TRIFLUOROMETHYL-THIENO[3,2-b]PYRIDINE-2-CARBOXYLIC ACID INDAN-2-YLAMIDE

[M+H$^+$] measured: 439 retention-time: 3.42 condition: c

Ex 339

5,6-DIMETHOXY-1H-INDOLE-2-CARBOXYLIC ACID INDAN-2-YLAMIDE

[M+H$^+$] measured: 337 retention-time: 2.91 condition: c

Ex 340

5-BROMO-N-INDAN-2-YL-2,3-DIMETHOXY-BENZAMIDE

[M+H$^+$] measured: 376 retention-time: 3.20 condition: c

Ex 341

1-(4-CHLORO-PHENYL)-5-METHYL-1H-PYRAZOLE-4-CARBOXYLIC ACID INDAN-2-YLAMIDE

[M+H$^+$] measured: 353 retention-time: 3.10 condition: c

Ex 342

3-CHLORO-4-METHYL-THIOPHENE-2-CARBOXYLIC ACID INDAN-2-YLAMIDE

[M+H$^+$] measured: 292 retention-time: 3.20 condition: c

Ex 343

1-ISOPROPYL-2-TRIFLUOROMETHYL-1H-BENZOIMIDAZOLE-5-CARBOXYLIC ACID INDAN-2-YLAMIDE

[M+H$^+$] measured: 388 retention-time: 3.10 condition: c

Ex 344

3-CHLORO-2,6-DIFLUORO-N-INDAN-2-YL-BENZAMIDE

[M+H$^+$] measured: 308 retention-time: 3.05 condition: c

Ex 345

2,6-DIFLUORO-N-INDAN-2-YL-3-METHYL-BENZAMIDE

[M+H$^+$] measured: 288 retention-time: 3.02 condition: c

Ex 346

2-CHLORO-6-FLUORO-N-INDAN-2-YL-3-METHYL-BENZAMIDE

[M+H$^+$] measured: 304 retention-time: 3.06 condition: c

Ex 347

6-CHLORO-2-FLUORO-N-INDAN-2-YL-3-METHYL-BENZAMIDE

[M+H$^+$] measured: 304 retention-time: 3.06 condition: c

Ex 348

N-INDAN-2-YL-2,5-DIMETHYL-BENZAMIDE

[M+H$^+$] measured: 266 retention-time: 3.07 condition: c

Ex 349

4-HEXYLAMINO-N-INDAN-2-YL-BENZAMIDE

[M+H$^+$] measured: 337 retention-time: 3.31 condition: c

Ex 350

4-BROMO-2-FLUORO-N-INDAN-2-YL-BENZAMIDE

[M+H$^+$] measured: 334 retention-time: 3.17 condition: c

Ex 351

1-(4-NITRO-PHENYL)-5-TRIFLUOROMETHYL-1H-PYRAZOLE-4-CARBOXYLIC ACID INDAN-2-YLAMIDE

[M+H$^+$] measured: 417 retention-time: 3.13 condition: c

Ex 352

2,3-DIHYDRO-BENZO[1,4]DIOXINE-5-CARBOXYLIC ACID INDAN-2-YLAMIDE

[M+H$^+$] measured: 296 retention-time: 3.01 condition: c

Ex 353

5-TRIFLUOROMETHOXY-1H-INDOLE-2-CARBOXYLIC ACID INDAN-2-YLAMIDE

[M+H$^+$] measured: 361 retention-time: 3.21 condition: c

Ex 354

5-CHLORO-3-PHENYL-1H-INDOLE-2-CARBOXYLIC ACID INDAN-2-YLAMIDE

[M+H$^+$] measured: 387 retention-time: 3.56 condition: c

Ex 355

2,5-DIOXO-2,3,4,5-TETRAHYDRO-1H-BENZO[E][1,4] DIAZEPINE-8-CARBOXYLIC ACID INDAN-2-YLAMIDE

[M+H$^+$] measured: 336 retention-time: 2.64 condition: c

Ex 356

3-PYRIDIN-2-YL-6-TRIFLUOROMETHYL-THIENO[3,2-B] PYRIDINE-2-CARBOXYLIC ACID INDAN-2-YLAMIDE; TRIFLUOR-ACETATE

[M+H$^+$] measured: 440 retention-time: 3.41 condition: c

Ex 357

2-ACETYLAMINO-5-CHLORO-THIOPHENE-3-CARBOXYLIC ACID INDAN-2-YLAMIDE

[M+H$^+$] measured: 335 retention-time: 3.20 condition: c

Ex 358

2-BROMO-6-FLUORO-N-INDAN-2-YL-BENZAMIDE

[M+H$^+$] measured: 334 retention-time: 3.01 condition: c

Ex 359

2-(2,4-DICHLORO-5-FLUORO-PHENYL)-N-INDAN-2-YL-ACETAMIDE

[M+H$^+$] measured: 338 retention-time: 3.17 condition: c

Ex 360

2-CHLORO-3,6-DIFLUORO-N-INDAN-2-YL-BENZAMIDE

[M+H$^+$] measured: 308 retention-time: 3.04 condition: c

Ex 361

N-INDAN-2-YL-2-METHYL-3-TRIFLUOROMETHYL-BENZAMIDE

[M+H$^+$] measured: 320 retention-time: 3.14 condition: c

Ex 362

2-CHLORO-5-SULFAMOYL-THIOPHENE-3-CARBOXYLIC ACID INDAN-2-YLAMIDE

[M+H$^+$] measured: 357 retention-time: 2.85 condition: c

Ex 363

2-CYANO-THIOPHENE-3-CARBOXYLIC ACID INDAN-2-YLAMIDE

[M+H$^+$] measured: 269 retention-time: 2.90 condition: c

Ex 364

3-BROMO-5-METHYL-THIOPHENE-2-CARBOXYLIC ACID INDAN-2-YLAMIDE

[M+H$^+$] measured: 336 retention-time: 3.24 condition: c

Ex 365

2-METHYL-THIOPHENE-3-CARBOXYLIC ACID INDAN-2-YLAMIDE

[M+H$^+$] measured: 258 retention-time: 3.01 condition: c

Ex 366

2-ETHYL-THIOPHENE-3-CARBOXYLIC ACID INDAN-2-YLAMIDE

[M+H$^+$] measured: 272 retention-time: 3.12 condition: c

Ex 367

2-METHANESULFINYL-THIOPHENE-3-CARBOXYLIC ACID INDAN-2-YLAMIDE

[M+H$^+$] measured: 306 retention-time: 2.77 condition: c

Ex 368

2,5-DIMETHYL-THIOPHENE-3-CARBOXYLIC ACID INDAN-2-YLAMIDE

[M+H$^+$] measured: 272 retention-time: 3.09 condition: c

Ex 369

4-(4-HEPTYL-BENZYLAMINO)-N-INDAN-2-YL-BENZAMIDE; SALT WITH TRIFLUORO-ACETIC ACID

[M+H$^{30}$] measured: 441 retention-time: 3.82 condition: c

Ex 370

1-(4-FLUORO-PHENYL)-3,5-DIMETHYL-1H-PYRAZOLE-4-CARBOXYLIC ACID INDAN-2-YLAMIDE

[M+H$^+$] measured: 350 retention-time: 3.01 condition: c

Ex 371

3-(4-FLUORO-BENZOYLAMINO)-BENZOIC ACID INDAN-2-YLAMIDE

[M+H$^+$] measured: 375 retention-time: 3.02 condition: c

Ex 372

N-INDAN-2-YL-3-ISOBUTYRYLAMINO-
BENZAMIDE

[M+H$^+$] measured: 323 retention-time: 2.93 condition: c

Ex 373

N-INDAN-2-YL-3-(2-PHENOXY-ACETYLAMINO)-
BENZAMIDE

[M+H$^+$] measured: 387 retention-time: 3.04 condition: c

Ex 374

N-INDAN-2-YL-3-PHENYLACETYLAMINO-
BENZAMIDE

[M+H$^+$] measured: 371

Ex 375

3-BUTYRYLAMINO-N-INDAN-2-YL-BENZAMIDE

[M+H$^+$] measured: 323 retention-time: 2.93 condition: c

Ex 376

3-(CYCLOPROPANECARBONYL-AMINO)-N-
INDAN-2-YL-BENZAMIDE

[M+H$^+$] measured: 321 retention-time: 2.89 condition: c

Ex 377

N-[3-(INDAN-2-YLCARBAMOYL)-PHENYL]-
NICOTINAMIDE

[M+H$^+$] measured: 358 retention-time: 2.81 condition: c

Ex 378

3-(3-METHYL-BENZOYLAMINO)-BENZOIC
ACID INDAN-2-YLAMIDE

[M+H$^+$] measured: 371 retention-time: 3.08 condition: c

Ex 379

FURAN-2-CARBOXYLIC ACID
[3-(INDAN-2-YLCARBAMOYL)-PHENYL]-AMIDE

[M+H$^+$] measured: 347 retention-time: 2.92 condition: c

Ex 380

3-(2,2-DIMETHYL-PROPIONYLAMINO)-N-IN-
DAN-2-YL-BENZAMIDE

[M+H$^+$] measured: 337 retention-time: 3.00 condition: c

Ex 381

3-(4-METHYL-BENZOYLAMINO)-BENZOIC
ACID INDAN-2-YLAMIDE

[M+H$^+$] measured: 371 retention-time: 3.06 condition: c

Ex 382

3-BROMO-N-INDAN-2-YL-BENZAMIDE

Rf (DIP)=0.38; MS (CI): 316 (M+1)+[M+H$^+$] measured: 316

Ex 383

2,2-DIMETHYL-3-OXO-3,4-DIHYDRO-2H-
BENZO[1,4] OXAZINE-6-CARBOXYLIC ACID
INDAN-2-YLAMIDE

Rf (MTB)=0.48; MS (ES−): 335 [M+H$^+$] measured: 337

Ex 384

3-(4-FLUORO-BENZENESULFONYLAMINO)-N-
INDAN-2-YL-BENZAMIDE

[M+H$^+$] measured: 411

Ex 385

5-(INDAN-2-YLCARBAMOYL)-NICOTINIC
ACID

[M+H$^+$] measured: 283 retention-time: 1.80 condition: b

Ex 386

PYRIDINE-3,5-DICARBOXYLIC ACID
BIS-INDAN-2-YLAMIDE

[M+H$^+$] measured: 398 retention-time: 2.32 condition: b

Ex 386A

5-AMINO-1-PYRIDIN-2-YL-1H-PYRAZOLE-4-
CARBOXYLIC ACID INDAN-2-YLAMIDE

[M+H$^+$] measured: 320

Ex 386B

N-INDAN-2-YL-4-(2,2,2-TRIFLUORO-ETHOXY)-
BENZAMIDE

[M+H$^+$] measured: 336 Rf (DIP)=0.20

Ex 387

6-CHLORO-N-INDAN-2-YL-NICOTINAMIDE

[M+H$^+$] measured: 273 retention-time: 2.19 condition: b

Ex 388

N-INDAN-2-YL-3-METHANESULFONYLAMINO-
BENZAMIDE

[M+H$^+$] measured: 331

Ex 389

4-FLUORO-N-(5-NITRO-INDAN-2-YL)-BENZAMIDE

To 5.0 g (19.6 mmol) 4-fluoro-N-(indan-2-yl)-benzamide was given, at 5–10° C., a nitrating mixture of 10 ml conc. nitric acid and 12 ml conc. sulfuric acid, followed by stirring over 3 h at room temperature. The mixture was worked up by pouring onto an ice/water mixture, extraction with ethyl acetate, washing of the organic phase with a solution of sodium hydrogen carbonate, drying and evaporating to dryness. The thus-obtained residue was crystallized form ethyl acetate/heptane. yield: 3.2 g (54%), mp.: 167° C.

Ex 390

N-(5-AMINO-INDAN-2-YL)-4-FLUOROBENZAMIDE 1.20 g (4.0 mmol) 4-fluoro-N-(5-nitro-indan-2-yl)-benzamide were hydrogenated in 100 ml of ethanol on a Pd/carbon catalyst at RT.

After the removal of the catalyst, 955 mg (ca.88%) product were obtained, which were used in the further reaction steps without any further purification.

Ex 391

N-(5-BENZOYLAMINO-INDAN-2-YL)-4-FLUOROBENZAMIDE 100 mg (0.37 mmol) N-(5-amino-indan-2-yl)-4-fluorobenzamide and 41.2 mg (0.41 mmol) triethylamine were dissolved in 2.5 ml THF, 57.2 mg (0.41 mmol) benzoyl chloride were added, and the whole was stirred over 6 h at RT. The mixture was then poured onto an ice/HCl mixture, the precipitate was filtered off and purified by prep. HPLC (RP18, acetonitrile/water, 1% trifluoroacetic acid). yield: 80 mg (58%)

[M+H$^+$] measured: 375.1 retention-time: 4.92 (95% H$_2$O (0.05% TFA) to 95% acetonitrile, 4 min, 95% acetonitrile 1.5 min, Merck Porospher 3µ, 2×55 mm)

There were obtained in an analogous way:

Ex 392

N-(5-ACETYLAMINO-INDAN-2-YL)-4-FLUOROBENZAMIDE

[M+H$^+$] measured: 313.1 retention-time: 4.30 (95% H$_2$O (0.05% TFA) to 95% acetonitrile, 4 min, 95% acetonitrile 1.5 min, Merck Porospher 3µ, 2×55 mm)

Ex 393

4-FLUORO-N-(5-(2-METHANSULFONYLAMINO)-INDAN-2-YL) BENZAMIDE

[M+H$^+$] measured: 341.1 retention-time: 4.68 (95% H$_2$O (0.05% TFA) to 95% acetonitrile, 4 min, 95% acetonitrile 1.5 min Merck Porospher 3µ, 2×55 mm)

Ex 394

4-FLUORO-N-(5-METHANSULFONYLAMINO-INDAN-2-YL)BENZAMIDE

[M+H$^+$] measured: 349.2 retention-time: 4.47 (95% H$_2$O (0.05% TFA) to 95% acetonitrile, 4 min, 95% acetonitrile 1.5 min, Merck Porospher 3µ, 2×55 mm)

Ex 395

N-(5-BENZENESUFONYLAMINO-INDAN-2-YL)-4-FLUOROBENZAMIDE

[M+H$^+$] measured: 411.2 retention-time: 4.89 (95% H$_2$O (0.05% TFA) to 95% acetonitrile, 4 min, 95% acetonitrile 1.5 min Merck Porospher 3µ, 2×55 mm)

Ex 396

N-(4-BROMO-INDAN-2-YL)-4-FLUORO-BENZAMIDE and N-(5-BROMO-INDAN-2-YL)-4-FLUORO-BENZAMIDE 8.0 g (31.3 mmol) N-(indan-2-yl)-4-fluoro-benzamide were dissolved in 125 ml DMF, 926 mg (3.1 mmol) Fe(III)-chloride were added, then 5.26 g (32.9 mmol) bromine were added dropwise. After 3 d stirring at RT the mixture was poured onto ice and extracted with ethyl acetate. After drying and evaporation, 6.2 g of a crystalline product were obtained. The two isomers were obtained from this mixture by means of a prep. HPLC-separation (silica, heptane/ethyl acetate).

Ex 396A

N-(4-BROMO-INDAN-2-YL)-4-FLUORO-BENZAMIDE (ENANTIOMER I)

mp.: 169° C.

Ex 396B

N-(5-BROMO-INDAN-2-YL)-4-FLUORO-BENZAMIDE (ENANTIOMER II)

mp.: 140° C.

Ex 397

N-(5,6-DIBROMO-INDAN-2-YL)-4-FLUORO-BENZAMIDE

The compound was obtained as a byproduct in the synthesis of example 396 A and B.

[M+H$^+$] measured: 412 retention-time: 5.17 condition: a

Ex 398A

4-FLUORO-N-[5-(4-FLUOROPHENYL)-INDAN-2-YL]-BENZAMIDE 251 mg (1.8 mmol) 4-fluorobenzene boronic acid, 500 mg (1.5 mmol) of a mixture of N-(4-bromo-indan-2-yl)-4-fluoro-benzamide (relative amount 20%) and N-(5-bromo-indan-2-YL)-4-fluoro-benzamide (relative amount 80%), 708 mg (2.24 mmol) barium hydroxide octahydrate and 50 mg tetrakis(triphenylphosphine)-palladium were suspended in 10 ml of water and 10 ml of dimethoxyethane, under an argon atmosphere, and stirred over 2 h at 80° C. The mixture was poured onto ice water, the formed precipitate was filtered off and crystallized from ethyl acetate/hexane. 170 mg (27%) 4-fluoro-N-[5-(4-fluorophenyl)-indan-2-yl]-benzamide, mp.: 193° C., were obtained.

Ex 398B

4-FLUORO-N-[4-(4-FLUOROPHENYL)-INDAN-2-yl]-BENZAMIDE

From the mother liquor of example 398A, there were obtained, by prep. HPLC, (RP18, acetonitrile/water, 1% trifluoroacetic acid) 71 mg (11%) 4-fluoro-N-[4-(4-fluorophenyl)-indan-2yl]-benzamide, mp.: 157° C.

Ex 399

N-(5-ACETYL-INDAN-2-YL)-4-FLUORO-BENZAMIDE 2.87 g (21.6 mmol) aluminum trichloride were suspended in 10 ml 1,2-dichloroethane, 500 mg (4.9 mmol) acetic anhydride and 1.0 g N-(indan-2-yl)-4-fluoro-benzamide added, and the whole was stirred for 2 h at RT. The resulting mixture was poured onto ice water/HCl, extracted with dichloromethane, the organic phase was dried with $Na_2SO_4$ and evaporated.

yield: 1.0 g (85%) mp.: 148° C.

There were obtained in an analogous way:

Ex 400

N-(5-BENZOYL-INDAN-2-YL)-4-FLUORO-BENZAMIDE mp.: 65° C.

Ex 401

N-[5-(3-DIMETHYLAMINO-PROPIONYL)-INDAN-2-YL]-4-FLUORO-BENZAMIDE-TRIFLUOROACETATE 340 mg (0.58 mmol) N-(5-acetyl-indan-2-yl)-4-fluoro-benzamide were dissolved in 20 ml dry ethanol, 0.1 ml conc. HCl, then 150 mg (1.74 mmol) N,N-dimethylmethylene-ammonium chloride were added, before the mixture was heated under reflux, for 8 h. The thus-obtained mixture was poured onto water, extracted with ethyl acetate, and the residue obtained after evaporation was fractionated by means of prep. HPLC (RP18, acetonitrile/water, 1% trifluoroacetic acid).

yield: 90 mg of a colorless oil (17%)

$^1$H (d6-DMSO, 300 MHz): 2.86 (s, 6H, N(CH$_3$)$_2$) 3.0–3.1 (m, 2H, —CH$_2$—), 3.3–3.4 (m, 2H, CH$_2$—), 3.4–3.5 (m, 2H, —CH$_2$—), 3.5–3.58 (m, 2H, —CH$_2$—), 4.75 (sextett, 1H CH—N), 7.3 (t, 2H, H$^{Phenylen}$), 7.45 (d, 1H, H$^7$), 7.85 (d,1H, H$^6$), 7.90 (s,1H, H$^4$), 7.90–8.00 (m, 2H, H$^{Phenylen}$)

Ex 402

4-FLUORO-N-[5-(1-HYDROXY-ETHYL)-INDAN-2-yl]-BENZAMIDE 400 mg (1.35 mmol) N-(5-acetyl-indan-2-yl)-4-fluoro-benzamide were dissolved in 10 ml of methanol, then 100 mg (2.7 mmol) sodium borohydride were added. The mixture was worked up by dropping onto ice/HCl, the resulting solid was filtered off.

yield: 300 mg (74%), mp.: 135° C.

There were obtained, in an analogous way:

Ex 403

4-FLUORO-N-[5-(HYDROXY-PHENYL-METHYL)-INDAN-2-yl]-BENZAMIDE mp.: 70° C.

Ex 404

4-FLUOR-N-(5-HYDROXY-INDAN-2-YL)-BENZAMIDE 1.45 g (5.08 mmol) 4-fluoro-N-(5-methoxy-indan-2-yl)-benzamide were dissolved in 50 ml of dichloromethane, 13 ml (12.7 mmol) boron tribromide (1M in dichloromethane) were added, the whole was stirred for 30 min at RT. The resulting mixture was poured onto 200 ml of ice water, the organic phase was washed twice with water, dried, evaporated and the residue obtained was subjected to chromatography on silica with a mixture of dichloromethane/methanol 98:2.

yield: 200 mg (16%), mp.: 199° C.

Ex 405

BENZENESULFONIC ACID 2-(4-FLUOROBENZOYLAMINO)-INDAN-5-YL ESTER 95 mg (0.35 mmol) 4-fluoro-N-(5-hydroxy-indan-2-yl)-benzamide were dissolved in 2 ml of pyridine, 120 mg (0.72 mmol) of benzenesulfonic acid chloride were added, and the mixture was stirred for 5 h at 70° C.

The mixture was dropped onto ice water extracted with ethyl acetate. The residue obtained after drying with Na$_2$SO$_4$ was subjected to chromatography on silica with a mixture of dichloromethane/methanol 98:2.

yield: 40 mg (41%)

$^1$H (d6-DMSO, 300 MHz): 2.91 (dd, 2H, —CH$_2$—), 3.22 (dd, 2H, —CH$_2$—), 4.70 (sextett, 1H CH—N), 6.75 (dd, 1H, H$^6$), 6.95 (d,1H, H$^4$), 7.20 (d,1H, H$^7$), 7.28 (t, 2H, H$^{Phenylen}$), 7.68 (t, 2H, H$^{Phenylen}$), 7.80–7.95 (m, 4H, H$^{Phenylen}$ and H$^{Phenyl}$), 8.68 (d, NH)

There was obtained, in an analogous way:

Ex 406

METHANESULFONIC ACID 2-(4-FLUOROBENZOYLAMINO)-INDAN-5-YL ESTER $^1$H (d6-DMSO, 300 MHz): 2.98 (dd, 2H, —CH$_2$—), 3.28 (dd, 2H, —CH$_2$—), 3.38 (s, 3H, CH$_3$) 4.73 (sextett, 1H CH—N), 7.16 (dd, 1H, H$^6$), 7.23 (d,1H, H$^4$), 7.25–7.35 (m,3H, H$^7$+H$^{Phenylen}$), 7.95 (ABdd, 2H, H$_{Phenylen}$), 8.70 (d, NH)

Ex 407

4-HYDROXYMETHYL-2-OXY-FURAZAN-3-CARBOXYLIC ACID INDAN-2-YLAMIDE

500 mg (2.95 mmoles) 2-aminoindane hydrochoride, 514 mg (2.95 mmoles) ethyl-4-hydroxymethyl-2-oxyfurazan-3-carboxylate and 298 mg (2.95 mmoles) triethylamine were stirred at 40° C. in 5 ml methanol for 4 h. The reaction mixture was poured on 20 g ice/diluted HCl and the resulting precipitate collected by filtration, yielding 495 mg 4-hydroxymethyl-2-oxy-furazan-3-carboxylic acid indan-2-ylamide as a white solid.

Mp.: 158° C. [M+H$^+$] measured: 276 retention-time: 4.71 condition: a

Ex 408

4-FLUORO-N-(4-IODO-INDAN-2-YL)-BENZAMIDE

500 mg (1.96 mmoles) N-indan-2-yl-4-fluoro-benzamide, 336 mg (2.74 mmoles) aluminum trichloride and 2080 mg (5.97 mmoles) benzyltrimethylammonium dichloroiodinate were stirred in 25 ml dry methylenchoride at RT for 18 h. Subsequently, the reaction mixture was poured on 40 g ice, the aqueous phase was extracted with methylenchoride and the combined organic phases were evaporated to dryness. The separation of the two isomers was achieved by chromatography on silica using n-heptane/ethylacetate 6:1 as eluent. Fraction 1:4-fluoro-N-(4-iodo-indan-2-yl)-benzamide Fraction 2:4-fluoro-N-(5-iodo-indan-2-yl)-benzamide.

[M+H$^+$] measured: 382 retention-time: 0.33 condition: c

Ex 409

4-FLUOR-N-(5-IODO-INDAN-2-YL)-BENZAMIDE

The compound was obtained according to example 408
[M+H$^+$] measured: 382 retention-time: 0.29 condition: d

Ex 410

4-FLUORO-N-{4-[2-(4-FLUORO-PHENYL)-VINYL]-INDAN-2-yl}-BENZAMIDE

150 mg (0.45 mmoles) 4-bromo-N-indan-2-yl-4-fluoro-benzamide, 1 mg palladium-(II)-acetate, 3.4 mg tri-o-tolyl phosphine and 88 mg (0.72 mmoles) para-fluorostyrene were combined in 2 ml triethylamine and stirred under reflux for 9 h. Subsequently, the reaction mixture was poured on a mixture of ice and diluted HCl, the mixture extracted with ethyl acetate and the resulting solution dried and evaporated to dryness. The residual oil was purified using prep. HPLC chromatography. (RP18, acetonitrile/water, 1% trifluoroacetic acid). 152 mg (90%) 4-fluoro-N-{4-[2-(4-fluoro-phenyl)-vinyl]-indan-2-yl}-benzamide were obtained.

[M+H$^+$] measured: 376 retention-time: 5.59 condition: a
There was obtained in an analogous way:

Ex 411

N-[4-(2-DIMETHYLCARBAMOYL-VINYL)-INDAN-2-YL]-4-FLUORO-BENZAMIDE

[M+H$^+$] measured: 353 retention-time: 3.57 condition: a

Ex 412

4-FLUORO-N-[4-(3-MORPHOLIN-4-YL-3-OXO-PROPENYL)-NDAN-2-YL]-BENZAMIDE

[M+H$^+$] measured: 395 retention-time: 4.53 condition: a

Ex 413

N-{4-[2-(4-CHLORO-PHENYLCARBAMOYL)-VINYL]-INDAN-2-YL}-4-FLUORO-BENZAMIDE

[M+H$^+$] measured: 435 retention-time: 5.33 condition: a

Ex 414

4-FLUORO-N-[4-(3-TRIFLUOROMETHYL-PHENYL)-INDAN-2-YL]-BENZAMIDE

150 mg (0.45 mmoles) 4-bromo-N-indan-2-yl-4-fluoro-benzamide, 102 mg (0.54 mmoles) 3-trifluoromethylbenzeneboronic acid, 211 mg (0.67 mmoles) barium hydroxide octahydrate and 20 mg tetrakis-triphenylphosphine-palladium were suspended in 10 ml 1,2-dimethoxyethane and 10 ml water and heated to reflux for 7 h. Subsequently, the reaction mixture was evaporated to dryness, the residue taken up in methylenchloride and extracted twice with water. The oil remaining after evaporation of the organic phase was purified using prep. HPLC chromatography. (RP18, acetonitrile/water, 1% trifluoroacetic acid). 80 mg (45%) of the title compound were obtained.

[M+H$^+$] measured: 400 retention-time: 5.36 condition: a
There was obtained in an analogous way:

Ex 415

N-[4-(3,5-DICHLORO-PHENYL)-INDAN-2-YL]-4-FLUORO-BENZAMIDE

[M+H$^+$] measured: 400 retention-time: 5.58 condition: a

Ex 416

4-FLUORO-N-(4-THIOPHEN-3-YL-INDAN-2-YL)-BENZAMIDE

[M+H$^+$] measured: 338 retention-time: 5.06 condition: a

Ex 417

N-[4-(5-CHLORO-THIOPHEN-2-YL)-INDAN-2-YL]-4-FLUORO-BENZAMIDE

[M+H$^+$] measured: 372 retention-time: 2.98 condition: b

Ex 418

N-[4-(2-CHLORO-PHEYNYL)-INDAN-2-YL]-4-FLUORO-BENZAMIDE

[M+H$^+$] measured: 366 retention-time: 2.85 condition: b

Ex 419

4-FLUORO-N-(4-PYRIDIN-3-YL-INDAN-2-YL)-BENZAMIDE; SALT WITH TRIFLUORO-ACETIC ACID

[M+H$^+$] measured: 333 retention-time: 1.78 condition: b

Ex 420

4-FLUORO-N-(4-PYRIDIN-4-YL-INDAN-2-YL)-BENZAMIDE; SALT WITH TRIFLUORO-ACETIC ACID

[M+H$^+$] measured: 333 retention-time: 1.77 condition: b

Ex 421

N-[4-(2,3-DICHLORO-PHENYL)-INDAN-2-YL]-4-FLUORO-BENZAMIDE

[M+H$^+$] measured: 400 retention-time: 2.96 condition: b

Ex 422

N-[4-(3,5-DIFLUORO-PHENYL)-INDAN-2-YL]-4-FLUORO-BENZAMIDE

[M+H$^+$] measured: 368 retention-time: 2.85 condition: b

Ex 423

N-[4-(3-CYANO-PHENYL)-INDAN-2-YL]-4-FLUORO-BENZAMIDE

[M+H$^+$] measured: 357 retention-time: 2.65 condition: b

Ex 424

N-[4-(2,3-DIFLUORO-PHENYL)-INDAN-2-YL]-4-FLUORO-BENZAMIDE

[M+H$^+$] measured: 368 retention-time: 2.79 condition: b

Ex 425

N-[4-(3-CARBAMOYLPHENYL)-INDAN-2-YL]-4-FLUORO-BENZAMIDE

[M+H$^+$] measured: 375 retention-time: 4.38 condition: a

Ex 426

5-OXO-1-PHENYL-4,5-DIHYDRO-1H-PYRAZOLE-3-CARBOXYLIC ACID INDAN-2-YLAMIDE prepared according to method B
[M+H$^+$] measured: 320 Rf (MTB)=0.3; (methyl tert.-butylether=MTB)

Ex 427

5-AMINO-1-PHENYL-1H-PYRAZOLE-4-CARBOXYLIC ACID INDAN-2-YLAMIDE prepared according to method B
[M+H$^+$] measured: 319 Rf (MTB/DIP 1:1)=0.2

Ex 428

N-(4-ETHYL-INDAN-2-YL)-4-FLUORO-BENZAMIDE 300 mg (0.87 mmoles) 4-bromo-N-indan-2-yl-4-fluoro-benzamide, 20 mg tetrakis-triphenylphosphine-palladium, a trace of 2,6-di-tert.-butyl-4-methylphenol and 310 mg (0.95 mmoles) tributylvinnylstannane in 7.5 ml toluene were heated to reflux for 4 h. Subsequently, 1 ml pyridine and 55 mg of pyridine hydrofluoric acid complex (70% HF) were added and the mixture stirred for 16 h. The resulting mixture was diluted with methyl-tert.-butylether, extracted with water, 1N HCl and saturated sodium hydrogen carbonate, the organic phases were dried and the oil remaining after evaporation purified using prep. HPLC chromatography. (RP 18, acetonitrile/water, 0.1% trifluoroacetic acid) yielding 108 mg (44%) of 4-fluoro-N-(4-vinyl-indan-2-yl)-benzamide. The latter was hydrogenated in ethanol with palladium on charcoal (10%, dry) to give, after prep. HPLC chromatography. (RP 18, acetonitrile/water, 1% trifluoroacetic acid) 45 mg (40%) of N-(4-ethyl-indan-2-yl)-4-fluoro-benzamide

[M+H$^+$] measured: 284 retention-time: 5.22 condition: a

Ex 429

N-(4,7-DIIODO-INDAN-2-YL)-4-FLUORO-BENZAMIDE 3.0 g 4-fluoro-N-indan-2-yl-benzamide were dissolved in 10 ml of trifluormethane sulfonic acid, cooled to 0° C. and 2.6 g N-iodosuccinimide added in three portions. Stirring was continued for 45 minutes at ambient temperature. The mixture was poured on ice, neutralized using saturated aqueous Na$_2$CO$_3$ solution and 50 ml of a saturated aqueous Na$_2$SO$_3$ solution added. The resulting mixture was extracted twice using 150 ml ethyl acetate each, dried using MgSO$_4$ and the solvent removed under reduced pressure. Chromatography on silica gel using ethyl acetate/n-heptane 1:4 yielded 200 mg of the desired compound as an amorphous solid. Rf=0.11.

[M+H$^+$] measured: 508

Ex 430

3-AMINO-1-PHENYL-1H-PYRAZOLE--CARBOXYLIC ACID INDAN-2-YLAMIDE a) 3-amino-1-phenyl-1H-pyrazole-4-carboxylic acid: 300 mg ethyl 3-amino-1-phenyl-1H-pyrazole-4-carboxylate were dissolved in 6 ml ethanol/THF 1:1 and 1.95 ml of an aqueous solution of NaOH added. Stirring was continued at ambient temperature for 2 days and the solvent removed under reduced pressure. The product was suspended in 5 ml of water and pH adjusted to pH=6 using aqueous solution of HCl. The product was filtered and dried under reduced pressure. Yield 200 mg of colorless crystals, m.p. 208–210° C. (decomposition); Rf (ethyl acetate/methanol 10:1)=0.53; MS (CI) 204 (M+1)+ b) 3-amino-1-phenyl-1H-pyrazole-4-carboxylic acid indan-2-ylamide was prepared using method B) Rf (CH$_2$Cl$_2$/DIP/MTB 5:5:2)=0.23.

[M+H$^+$] measured: 319

Ex 431

4-AMINO-5-OXO-1-PHENYL-2,5-DIHYDRO-1H-PYRROLE-3-CARBOXYLIC ACID INDAN-2-YLAMIDE a) 4-amino-5-oxo-1-phenyl-2,5-dihydro-1H-pyrrole-3-carboxylic acid was obtained following the procedure described above (example 430).

b) Rf (DIP)=0.08. The compound was then obtained using method B.

[M+H$^+$] measured: 334

Ex 432

N-INDAN-2-YL-3-PYTIDIN-3-YL-BENZAMIDE 100 mg of 3-bromo-N-indan-2-yl-benzamide, 88 mg bis-(pinacolato)-dibor, 93 mg potassium acetate and 48 mg PdCl(dppf) were dissolved in 6 ml DMF and stirred at 80° C. for 2 h. The solution was cooled to ambient temperature and 100 mg of 3-bromo-pyridine added. Then, further 24 mg of PdCl(dppf) were added and the mixture stirred at 80° C. for 3.5 h. The mixture was cooled to ambient temperature and diluted with 20 ml ethyl acetate. The crude mixture was washed three times with 5 ml of a saturated aqueous solution of Na$_2$CO$_3$ each and dried over MgSO$_4$. The solvents were removed under reduced pressure and the residue purified by chromatography on silica gel using MTB. Yield 60 mg of a viscous oil. Rf (MTB)=0.2.

[M+H$^+$] measured: 315

There were obtained in an analogous way:

Ex 433

N-INDAN-2-YL-3-PYRIDIN-2-YL-BENZAMIDE; SALT WITH TRIFLUOR-ACETIC ACID

[M+H$^+$] measured: 315 retention-time: 1.88 condition: b

Ex 434

N-INDAN-2-YL-3-PYRIDIN-4-YL-BENZAMIDE; SALT WITH TRIFLUOR-ACETIC ACID

[M+H$^+$] measured: 315 retention-time: 1.74 condition: b

Ex 435

N-INDAN-2-YL-4-PYRIDIN-3-YL-BENZAMIDE; SALT WITH TRIFLUORO-ACETIC ACID

[M+H$^+$] measured: 315 retention-time: 1.75 condition: b

Ex 436

N-INDAN-2-YL-4-PYRIDIN-2-YL-BENZAMIDE; SALT WITH TRIFLUORO-ACETIC ACID

[M+H$^+$] measured: 315 retention-time: 1.86 condition: b

Ex 437

N-INDAN-2-YL-4-PYRIDIN-4-YL-BENZAMIDE; SALT WITH TRIFLUORO-ACETIC ACID

[M+H$^+$] measured: 315 retention-time: 1.73 condition: b

Ex 438

N-INDAN-2-YL-2-PYRIDIN-4-YL-BENZAMIDE; SALT WITH TRIFLUORO-ACETIC ACID

[M+H$^+$] measured: 315 retention-time: 1.59 condition: b

Ex 439

4-FLUORO-N-(4-TRIFLUOROMETHYL-INDAN-2-YL)-BENZAMIDE a) 4-trifluoromethyl-indan-1-one: 4.5 g 3-(2-trifluoromethyl-phenyl)-propionic acid were dissolved in 15 ml SOCl$_2$ and the solution refluxed for 2 h. The volatiles were removed under reduced pressure and the residue dissolved in 50 ml of dry CH$_2$Cl$_2$. Again, the volatiles were removed under reduced pressure. The residue was dissolved using 100 ml of dry CH$_2$Cl$_2$ and divided into 10 equal parts. Each part was diluted with 20 ml dry CH$_2$Cl$_2$, cooled to −70° C. and 160 μl of trifluormethane sulfonic acid added. Slow warm-up over a period of 4 h was followed by stirring at ambient temperature for 18 h. The separate reaction mixtures were combined in 200 ml of a saturated aqueous solution of Na$_2$CO$_3$ and extracted three times with 100 ml CH$_2$Cl$_2$ each. The solution was dried using MgSO$_4$ and the solvent removed under reduced pressure. The residue was purified using chromatography on silica gel using ethyl acetate/n-heptane 1:8 as eluent. Yield 300 mg of a colourless oil. Rf=0.2; MS (CI): 201 (M+1)+.

b) 4-trifluoromethyl-indan-1,2-dione 2-oxime: 33 μl methanol, 1.5 ml CH$_2$Cl$_2$ and 2.6 ml n-heptane were mixed and 47 μl acetyl chloride added at 0° C. Next was the dropwise addition of 520 mg of 4-trifluoromethyl-indan-1-one in 2 ml CH$_2$Cl$_2$ at 0° C. followed by the addition of 335 mg of 3-methyl-butylnitrite. Stirring was continued for 2 h at 0° C. The crude reaction mixture was then diluted with 10 ml n-heptane, the CH$_2$Cl$_2$ removed under reduced pressure and the product filtered and dried under reduced pressure. Yield 270 mg, pale yellow crystals. m.p. 185–187° C.; MS (CI): 230 (M+1)+.

c) 4-trifluoromethyl-indan-2-ylamine: 460 mg of 4-trifluoromethyl-indan-1,2-dione 2-oxime were dissolved in 15 ml acetic acid, 500 μl H$_2$SO$_4$ (conc.) and 200 mg Pd/C (10%) added. The mixture was hydrogenated for 24 h (5 bar H$_2$). The catalyst was then removed by filtration, the acetic acid removed under reduced pressure and the mixture diluted with 30 ml of water. pH=9 was adjusted using a saturated aqueous solution of Na$_2$CO$_3$. The product was then extracted three times using 30 ml ethyl acetate each. The solution was dried using MgSO$_4$ and the solvent removed under reduced pressure. Yield 200 mg; Rf (ethyl acetate/methanol 10:1)=0.1; MS (CI): 202 (M+1)+.

d) 4-fluoro-N-(4-trifluoromethyl-indan-2-yl)-benzamid was prepared following method B). Yield 57 mg; Rf (DIP)=0.28; MS (CI): 324 (M+1)+

[M+H$^+$] measured: 324

Ex 440

5-AMINO-1-(6-ETHOXY-PYRIDAZIN-3-YL)-1H-PYRAZOLE-4-CARBOXYLIC ACID INDAN-2-YLAMIDE a) 5-amino-1-(6-ethoxy-pyridazin-3-yl)-1H-pyrazole-4-carboxylic acid: 1.0 g 5-amino-1-(6-chloro-pyridazin-3-yl)-1H-pyrazole-4-carboxylic acid ethyl ester were dissolved in 6 ml ethanol and 4.5 ml of a 1N aqueous solution of NaOH added. The mixture was refluxed for 2 h, the solvent was then removed under reduced pressure. 20 ml water were added to the residue and pH=6 adjusted using an aqueous solution of HCl. The aqueous solution was extracted three times with 100 ml ethyl acetate each. The solution was dried using MgSO$_4$ and the solvent removed under reduced pressure.
Yield 200 mg, viscous oil; Rf (DIP)=0.11; MS (CI): 250 (M+1)+.

b) 5-amino-1-(6-ethoxy-pyridazin-3-yl)-1H-pyrazole-4-carboxylic acid indan-2-ylamide was synthesized using method B). Rf (MTB/DIP 1:1)=0.26.
[M+H$^+$] measured: 365

Ex 441

1-PYRIDIN-2-YL-1H-BENZOIMIDAZOLE-5-CARBOXYLIC ACID INDAN-2-YLAMIDE a) 3-pyridin-2-yl-3H-benzoimidazole-5-carboxylic acid methyl ester as a mixture with 1-pyridin-2-yl-1H-benzoimidazole-5-carboxylic acid methyl ester: 1.0 g benzoimidazole-5-carboxylic acid methyl ester, 1.1 g 2-fluoropyridine and 3.7 g Cs$_2$CO$_3$ were dissolved in 60 ml of dry DMF. The mixture was stirred at 120° C. for 8 h. After cooling to ambient temperature, the mixture was poured into 200 ml of water and stirred at ambient temperature for 1 h. The precipitated product was filtrated and dried under reduced pressure. Yield 500 mg, pale yellow oil. Rf (MTB)=0.13; MS (ES+): 254 (M+1)+ b) 3-pyridin-2-yl-3H-benzoimidazole-5-carboxylic acid as a mixture with 1-pyridin-2-yl-1H-benzoimidazole-5-carboxylic acid: 400 mg of a mixture of esters a) were dissolved in 5 ml methanol and 1.9 ml of a 1N aqueous solution of NaOH added. The mixture was refluxed for 2 h, the solvent removed under reduced pressure. 10 ml of water were added to the residue and pH=6 adjusted using an aqueous solution of HCl. The precipitating product was filtered and dried under reduced pressure. Yield 280 mg. amorphous solid. Rf(EE)=0.14; MS (CI): 240 (M+1)+.

c) 3-pyridin-2-yl-3H-benzoimidazole-5-carboxylic acid indan-2-ylamide as a mixture with 1-pyridin-2-yl-1H-benzoimidazole-5-carboxylic acid indan-2-ylamide was synthesized using general procedure B). Rf (EE)=0.13; MS (ES+): 355 (M+1)+.
[M+H$^+$] measured: 355

CHROMATOGRAPHIC CONDITIONS (HPLC) FOR ABOVE EXAMPLES (unless indicated otherwise)

condition a   Merck Porospher 55 × 2 mm, 5μ, gradient: 95% H20 (0.05% TFA) to 95% acetonitrile, 4 min, 95% acetonitrile 1.5 min, 0.5 ml/min)
condition b   YMC J'Sphere ODS H80, 33 × 2.1 mm, 3μ, gradient: 90% H20 (0.05% TFA) to 95% acetonitrile, 2.5 min, 95% acetonitrile 0.8 min, 1 ml/min)
condition c   LiChroCart 55-2, PuroSpher STAR; RP 18 e (MERCK), solvent A: acetonitril/water (90:10) + 0.5% formic acid; solvent B: acetonitrile/water (90:10) + 0.5% formic acid; gradient: 95% B 0.5 min, 95% B to 5% B in 1.75 min, 5% B 2.5 min; 1 ml/min
condition d   TLC, Silica gel 60, F254 (Merck), Solvent: n-heptane: ethylacetate 1:1 retention times are given in minutes (for each condition)
Measurement of Activation of eNOS Transcription Activation of eNOS transcription was measured as described in detail in Li et al. "Activation of protein kinase C alpha and/or epsilon enhances transcription of the human endothelial nitric oxide synthase gene", Mol. Pharmacol. 1998; 53: 630–637.

Briefly, a 3.5 kB long fragment 5' of the starting codon of the eNOS gene was cloned, sequenced and cloned in firefly luciferase expression plasmids to monitor activation of the eNOS promoter by reporter gene activity. A human endothelial cell line stable transfected and expressing this promoter-reporter construct was used for compound testing. Cells were incubated for 18 h with compounds.

All compounds were dissolved in sterile DMSO. A final concentration of 0.5% DMSO in complete medium was allowed. Induction of reporter gene expression in these cells was measured using a standard luciferase assay system (Promega, Cat. No E150) according to the manufacturer's instructions. Luciferase induction in cells incubated with compounds were compared to those incubated with solvent alone. The ratio of both activities (transcription induction ratio, TIR) was plotted as a function of compound concentration. Typically, TIR values started at low concentrations at a ratio of 1, indicating no compound effect, and extended up to a maximum TIR value TIR(max) which indicates the increase of the eNOS transcription. EC$_{50}$ values of transcription induction ratios as a function of compound concentration were determined graphically.

The effect of compounds on eNOS-transcription were confirmed in a second assay based on eNOS protein detection. Primary human umbilical vein cord endothelial cells (HUVEC) were isolated and cultivated according to standard procedures. Confluent cells were incubated with compounds for 18 h and the effect on eNOS protein expression determined by a quantitative Westernblotting procedure. After incubation with the compounds, HUVEC were lyzed in ice-cold lysis buffer containing 10 mM Tris-HCl, pH 8.0, 1% SDS and protease inhibitors. The lyzate was subjected to a standard denaturating polyacrylamid gel electrophoresis and blotted to nitrocellulose membranes. Using a specific primary monoclonal antibody (Transduction Laboratories, UK) and alkaline phosphatase labelled secondary antibody (Jackson Labs), a specific eNOS protein band was visualized and quantified based on a chemifluorescence detection method.

The results are shown in the table below.

| Compound No: | EC-50 (μM) | TIR(max) |
|---|---|---|
| 1a | 6.0 | 2.80 |
| 1b | 0.2 | 3.00 |
| 4  | 3.0 | 2.95 |

-continued

| Compound No: | EC-50 (µM) | TIR(max) |
|---|---|---|
| 5 | 30 | 2.50 |
| 6 | 1.2 | 2.55 |
| 7 | 0.1 | 2.57 |
| 8 | 8.0 | 2.20 |
| 21 | 0.8 | 4.10 |
| 22 | 7.0 | 2.10 |
| 23 | 5.0 | 2.20 |
| 24 | 2.5 | 2.88 |
| 25 | 12 | 2.70 |
| 26 | 0.9 | 3.80 |
| 27 | 0.2 | 3.60 |
| 28 | 2.5 | 4.40 |
| 29 | 0.8 | 3.80 |
| 30 | 3.0 | 2.94 |
| 31 | 6.0 | 3.05 |
| 32 | 1.7 | 4.00 |
| 33 | 4.0 | 3.30 |
| 34 | 1.7 | 3.40 |
| 41 | 0.18 | 2.4 |
| 61 | 0.7 | 2.60 |
| 66 | 0.14 | 2.7 |
| 69 | 0.4 | 4.20 |
| 73 | 0.7 | 4.00 |
| 185 | 27 | 2.4 |
| 187 | 4.4 | 2.5 |
| 189 | 10 | 2.2 |
| 203 | 16 | 2.7 |
| 216 | 0.7 | 2.8 |
| 230 | 0.820 | 4 |
| 233 | 13 | 2.5 |
| 236 | 22 | 2 |
| 237 | 7.7 | 2.5 |
| 243 | 0.110 | 2.8 |
| 246 | 0.670 | 2.5 |
| 248 | 7.8 | 2.8 |
| 249 | 15 | 2.5 |
| 250 | 58 | 2.5 |
| 251 | 13 | 2.6 |
| 253 | 13 | 2.2 |
| 256 | 11 | 2.5 |
| 257 | 4.3 | 2.7 |
| 262 | 5.8 | 2.8 |
| 263 | 13 | 2.5 |
| 264 | 0.580 | 2.9 |
| 265 | 0.183 | 2.7 |
| 266 | 22 | 2.5 |
| 267 | 2.8 | 2.5 |
| 268 | 0.485 | 3 |
| 272 | 1.6 | 2.9 |
| 273 | 2.6 | 2.8 |
| 274 | 21 | |
| 275 | 0.559 | 3 |
| 276 | 0.157 | 3 |
| 277 | 4.1 | 3 |
| 281 | 0.684 | 3 |
| 282 | 16 | 2.3 |
| 283 | 15 | 2.5 |
| 286 | 26 | 2.6 |
| 287 | 13 | 2.9 |
| 289 | 0.142 | 2.6 |
| 291 | 0.238 | 2.8 |
| 292 | 0.039 | 2.9 |
| 293 | 14 | 1.7 |
| 294 | 14 | 2.2 |
| 295 | 0.846 | 2.4 |
| 296 | 13 | 2.5 |
| 302 | 27 | 2.8 |
| 306 | 0.263 | 2.7 |
| 312 | 16 | 2.2 |
| 314 | 12 | 2.2 |
| 315 | 16 | 2.2 |
| 317 | 0.197 | 2.9 |
| 319 | 25 | 2.4 |
| 320 | 12 | 3 |
| 321 | 9.6 | 2.5 |
| 322 | 23 | 2.3 |
| 324 | 2.1 | 1.7 |
| 327 | 2.6 | 2.5 |
| 328 | 24 | 2.4 |
| 329 | 2.2 | 1.5 |
| 330 | 12 | 2.2 |
| 331 | 0.147 | 2.8 |
| 332 | 4.0 | 2 |
| 335 | 0.943 | 2.7 |
| 341 | 22 | 2.5 |
| 342 | 0.287 | 3 |
| 346 | 26 | 2.6 |
| 350 | 0.523 | 2.9 |
| 358 | 4.7 | 2.5 |
| 360 | 10 | 2.6 |
| 361 | 21 | 2.5 |
| 364 | 2.1 | 2.9 |
| 365 | 0.250 | 3 |
| 366 | 37 | 2.5 |
| 368 | 17 | 2.5 |
| 372 | 1.6 | 2.7 |
| 375 | 8.0 | 2.3 |
| 376 | 5.3 | 2.4 |
| 380 | 2.3 | 2.6 |
| 381 | 12 | 2.5 |
| 382 | 21 | 2.5 |
| 386A | 5.1 | 3.3 |
| 386B | 0.309 | 2.5 |
| 387 | 32 | 2.6 |
| 388 | 1.1 | 2.4 |
| 396A | 0.6 | 3.55 |
| 397 | 30 | 1.7 |
| 398B | 30 | 3.46 |
| 404 | 12 | 3.50 |
| 405 | 30 | 2.80 |
| 408 | 11 | 2.5 |
| 411 | 2.0 | 2.5 |
| 412 | 1.0 | 2.5 |
| 413 | 8.5 | 2.5 |
| 427 | 3.7 | 2.5 |
| 428 | 0.841 | 2.8 |
| 429 | 0.6 | 2.8 |
| 432 | 9.6 | 2.5 |
| 433 | 19 | 2.6 |
| 435 | 14 | 2.5 |
| 436 | 18 | 2.6 |
| 439 | 8.9 | 2.6 |

Animal Models

All animals experiments were performed in accordance to the German animal protection law and to the guidelines for the use of experimental animals as given by the Guide for the Care and Use of Laboratory Animals of the US National Institutes of Health.

Animals and Treatment (Experiments A–C)

ApoE and eNOS deficient mice (C57BL/6J background, Jackson Laboratory, Bar Harbor, Me.) were used. All animals were 10–12 weeks of age and weighed 22 to 28 g. Three days before surgery mice were divided into 4 groups (apoE control, n=10–12; apoE with test compounds, n=10–12; eNOS control, n=10–12; eNOS with test compounds, n=10–12) and received either a standard rodent chow (containing 4% fat and 0.001% cholesterol; in the following designated as placebo group) or a standard rodent chow+test compound (10 or 30 mg/kg/d p.o.).

A Anti-hypertensive Effect in ApoE Knockout Mice

Blood-pressure was determined in conscious mice using a computerized tail-cuff system (Visitech Systems, Apex, N.C.). After treatment of ApoE deficient mice and eNOS deficient mice with the test compounds the blood pressure was compared to the results obtained with a placebo treatment.

For compound 21, after 4 months treatment of ApoE deficient mice blood pressure was significantly p<0.05) lowered in the 30 mg/kg/d group compared to placebo treatment (92±5 mmHg versus 115±2 mmHg). No blood pressure reduction could be observed at similar dosing in eNOS deficient mice after 4 weeks treatment.

B Inhibition of Neointima Formation and Atherogenesis (Femoral Artery Cuff)

After 3 day treatment of ApoE deficient mice with the respective compound, (10 mg/kg/d pressed in chow), animals were anesthetized with an intraperitoneal injection of pentobarbital (60 mg/kg) followed by an intramuscular injection of xylazin (2 mg/kg) and a cuff was placed around the femoral artery as described in Moroi et al. (J. Clin. Invest. 101:1225–32, 1998). Briefly, the left femoral artery was dissected. A non-occlusive 2.0 mm polyethylene cuff made of PE-50 tubing (inner diameter 0.56 mm, outer diameter 0.965 mm, Becton Dickinson, Mountain View, Calif.) was placed around the artery and tied in place with two 7-0 sutures. The right femoral artery was isolated from the surrounding tissues but a cuff was not placed. Treatment with the respective compound was continued for 14 days after surgery. Then the animals were sacrificed. The aorta were taken for determination of vascular eNOS expressions by quantitative western blotting. Both femoral arteries were harvested, fixed in formalin and embedded in paraffin. 20 cross sections (10 μm) were cut from the cuffed portion of the left femoral artery and from the corresponding segment of the right artery. Sections were subjected to standard hematoxylin and eosin staining. Morphometric analyses were performed using an image analysis computer program (LeicaQwin, Leica Imaging Systems, Cambridge, GB). For each cross section the area of the lumen, the neointima and the media were determined. To this end, the neointima was defined as the area between the lumen and the internal elastic lamina and the media was defined as the area between the internal and the external elastic lamina. The ratio between the area of the neointima and the area of the media was expressed as the neointima/media ratio.

The compounds according to the present invention reduce the maladaptive neo-intima formation in this model. Compound 21 reduced the neo-intima formation by a factor of 2, decreasing the neointima to media ratio from 0.39±0.07 in the placebo group to 0.170±0.04 in the compound group. In parallel, vascular eNOS expression was enhanced by a factor of 2.1. No effect of the compounds according to the present invention could be demonstrated in a similar setup using eNOS deficient mice instead of ApoE knockout mice.

Prevention of Atherosclerotic Plaque Formation in Chronic Treatment

ApoE deficient mice were treated for 16 weeks with the respective compound pressed in chow and finally sacrificed. Aortas were removed from each mouse, fixed in formalin and embedded in paraffin. Plaque formation was measured via lipid lesion formation in the aortas (from aortic arch to diaphragm) and was analyzed by oil red O staining. For quantifying the effect of the respective compound on vascular eNOS expression the femoral arteries were used in this experiment.

The compounds according to the present invention reduce plaque formation. With respect to compound 21, plaque formation was significantly reduced (5.2±1% versus 13.3±2.6 in the placebo group, values in overall plaque size in % of total surface). Vascular eNOS expression was found to be 1.75 fold up-regulated in the treatment group.

D Improvement of Coronary Function in Diseased ApoE Deficient Mice

Old Male wild-type C57BL/6J mice (Charles River Wiga GmbH, Sulzfeld), and apoE deficient mice (C57BL/6J background, Jackson Laboratory, Bar Harbor, Me.) 6 month of age and weighing 28 to 36 g were used in the experiments. Mice were divided into 3 groups (C57BL/6, n=8; apoE control, n=8; apoE with respective compound, n=8) and received for 8 weeks either a standard rodent chow (containing 4% fat and 0.001% cholesterol) or a standard rodent chow+respective compound (30 mg/kg/d p.o.).

Mice were anesthetized with sodium pentobarbitone (100 mg/kg i.p.), and the hearts were rapidly excised and placed into ice-cold perfusion buffer. The aorta was cannulated and connected to a perfusion apparatus (HUGO SACHS ELECTRONICS, Freiburg, Germany) which was started immediately at a constant perfusion pressure of 60 mm Hg. Hearts were perfused in a retrograde fashion with modified Krebs bicarbonate buffer, equilibrated with 95% $O_2$ and 5% $CO_2$ and maintained at 37.5° C.

A beveled small tube (PE 50) was passed through a pulmonary vein into the left ventricle and pulled through the ventricular wall, anchored in the apex by a fluted end, and connected to a tip-micromanometer (Millar 1.4 French). The left atrium was cannulated through the same pulmonary vein and the heart switched to the working mode with a constant preload pressure of 10 mm Hg and an afterload pressure of 60 mm Hg. Aortic outflow and atrial inflow were continuously measured using ultrasonic flow probes (HSE/Transonic Systems Inc.). Coronary flow was calculated as the difference between atrial flow and aortic flow. All hemodynamic data were digitized at a sampling rate of 1000 Hz and recorded with a PC using specialized software (HEM, Notocord).

Hearts were allowed to stabilize for 30 min. All functional hemodynamic data were measured during steady state, and during volume- and pressure loading.

Left ventricular function curves were constructed by varying pre-load pressure. For acquisition of pre-load curves, afterload was set at 60 mm Hg and pre-load was adjusted in 5 mm Hg steps over a range of 5 to 25 mm Hg. Hearts were allowed to stabilize at baseline conditions between pressure- and volume-loading.

Isolated hearts from ApoE deficient animals displayed a lower coronary flow in this setup compared to C57B16 wildtype mice (3.6 ml/min versus 4.95 ml/min). Treatment of ApoE deficient animals with the compounds according to the present invention increased coronary flow. They also improved pre-load dependent coronary flow and reduced the incidence of ventricular arrhythmias as an indicator for anti-ischemic efficacy. With respect to compound 21, coronary flow was improved to 5 ml/min comparable to the levels of non-diseased wildtype mice, and the improvement in pre-load dependent coronary flow and the reduction of the incidence of ventricular arrhythmics were also observed.

We claim:

1. An acylated indanyl amine according to the general formula (I) in any of its stereoisomeric forms or a mixture thereof in any ratio or a pharmaceutically acceptable salt thereof

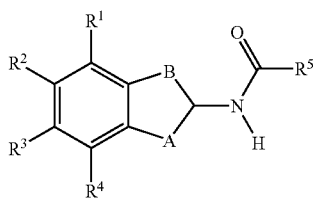 (I)

wherein
R¹ and R⁴ are independently from each other selected from the group consisting of:
H;
unsubstituted and at least monosubstituted $C_1$–$C_{10}$-alkyl, $C_2$–$C_{10}$-alkenyl and $C_2$–$C_{10}$-alkynyl, the substituents of which are selected from the group consisting of F, OH, $C_1$–$C_8$-alkoxy, ($C_1$–$C_8$-alkyl)mercapto, CN, COOR⁶, CONR⁷R⁸, and unsubstituted and at least monosubstituted phenyl, the substituents of which are selected from the group consisting of halogens, pseudohalogens, $C_1$–$C_3$-alkyl, $C_1$–$C_3$-alkoxy and $CF_3$;
unsubstituted and at least monosubstituted phenyl, the substituents of which are selected from the group consisting of halogens, pseudohalogens, $C_1$–$C_3$-alkyl, $C_1$–$C_3$-alkoxy and $CF_3$;
R⁹CO;
CONR¹⁰R¹¹;
COOR¹²;
$CF_3$;
halogens;
pseudohalogens;
NR¹³R¹⁴;
OR¹⁵;
$S(O)_mR^{16}$;
$SO_2NR^{17}R^{18}$;
and $NO_2$;
R² and R³ independently from each other selected from the group consisting of:
H;
halogens;
pseudohalogens;
unsubstituted and at least monosubstituted $C_1$–$C_{10}$-alkyl the substituents of which are selected from the group consisting of OH and phenyl;
OH;
$C_1$–$C_{10}$-alkoxy;
phenoxy;
$S(O)_mR^{19}$;
$CF_3$;
CN;
$NO_2$;
($C_1$–$C_{10}$-alkyl)amino;
di($C_1$–$C_{10}$-alkyl)amino;
($C_1$–$C_6$-alkyl)-CONH—;
unsubstituted and at least monosubstituted phenyl-CONH— and phenyl-$SO_2$—O—, the substituents of which are selected from the group consisting of halogens, pseudohalogens, $CH_3$ and methoxy;
($C_1$–$C_6$-alkyl)$SO_2$—O—;
unsubstituted and at least monosubstituted ($C_1$–$C_6$-alkyl)CO, the substituents of which are selected from the group consisting of F and di($C_1$–$C_3$-alkyl)amino;
and phenyl-CO, the phenyl part of which can be substituted by one or more substituents from the group consisting of $C_1$–$C_3$-alkyl, halogens and methoxy;
A is selected from the group consisting of $CH_2$, CHOH and CH—($C_1$–$C_3$-alkyl);
B is selected from the group consisting of $CH_2$ and CH—($C_1$–$C_3$-alkyl);
R⁵ is a benzo[1,3] dioxole group optionally substituted with one or more substituents selected from the group consisting of:
halogens;
pseudohalogens;
$NH_2$;
unsubstituted and at least monosubstituted $C_1$–$C_{10}$-alkyl, $C_2$–$C_{10}$-alkenyl, $C_2$–$C_{10}$-alkynyl, $C_1$–$C_{10}$-alkoxy, ($C_1$–$C_{10}$-alkyl)amino, and di($C_1$–$C_{10}$-alkyl)amino, the substituents of which are selected from the group consisting of F, OH, $C_1$–$C_8$-alkoxy, aryloxy, ($C_1$–$C_8$-alkyl)mercapto, $NH_2$, ($C_1$–$C_8$-alkyl)amino; and di($C_1$–$C_8$-alkyl)amino; $C_3$–$C_5$-alkandiyl;
phenyl;
aryl-substituted $C_1$–$C_4$-alkyl;
$CF_3$;
$NO_2$;
OH;
phenoxy;
benzyloxy;
($C_1$–$C_{10}$-alkyl)COO;
$S(O)_mR^{20}$;
SH;
phenylamino;
benzylamino;
($C_1$–$C_{10}$-alkyl)-CONH—;
($C_1$–$C_{10}$-alkyl)-CON($C_1$–$C_4$-alkyl)-;
phenyl-CONH—;
phenyl-CON($C_1$–$C_4$-alkyl)-;
($C_1$–$C_{10}$-alkyl)-CO;
phenyl-CO;
$CF_3$—CO;
—$OCH_2O$—;
—$OCF_2O$—;
—$OCH_2CH_2O$—;
—$CH_2CH_2O$—;
COOR²¹;
CONR²²R²³;
$CNH(NH_2)$;
$SO_2NR^{24}R^{25}$;
$R^{26}SO_2NH$—;
$R^{27}SO_2N(C_1$–$C_6$-alkyl)-;
and wherein all aryl, phenyl, aryl-containing, phenyl-containing groups, which are optionally present in the said substituents of the benzo[1,3]dioxole group can be substituted by one or more substituents selected from the group consisting of halogens, pseudohalogens, $C_1$–$C_3$-alkyl, OH, $C_1$–$C_3$-alkoxy, and $CF_3$;
R⁶ is selected from the group consisting of:
H;
$C_1$–$C_{10}$-alkyl, which can be substituted by one or more substituents selected from the group consisting of F, $C_1$–$C_8$-alkoxy, and di($C_1$–$C_8$-alkyl)amino;
aryl-($C_1$–$C_4$-alkyl) optionally substituted by one or more substituents selected from the group consisting of halogens, $C_1$–$C_4$-alkoxy, and di($C_1$–$C_6$-alkyl)amino;
R⁷ is selected from the group consisting of:
H;

$C_1$–$C_{10}$-alkyl which can be substituted by one or more substituents selected from the group consisting of F, $C_1$–$C_8$-alkoxy, di($C_1$–$C_8$-alkyl)amino and phenyl;
phenyl;
indanyl;
and wherein each of the aforementioned aromatic groups can be unsubstituted or carry one or more substituents from the group consisting of halogens, pseudohalogens, $C_1$–$C_3$-alkyl, $C_1$–$C_3$-alkoxy and $CF_3$;
$R^8$ is H or $C_1$–$C_{10}$-alkyl;
$R^9$ is selected from the group consisting of:
  $C_1$–$C_{10}$-alkyl which can be unsubstituted or carry one or more substituents from the group consisting of: F, ($C_1$–$C_4$)-alkoxy, di($C_1$–$C_3$-alkyl)amino;
  and unsubstituted and at least monosubstituted phenyl and heteroaryl, the substituents of which are selected from the group consisting of $C_1$–$C_3$-alkyl, $C_1$–$C_3$-alkoxy, halogens, pseudohalogens, and $CF_3$;
$R^{10}$ independently has the same meaning as $R^7$;
$R^{11}$ independently has the same meaning as $R^8$;
$R^{12}$ independently has the same meaning as $R^6$;
$R^{13}$ is selected from the group consisting of:
  H;
  $C_1$–$C_6$-alkyl;
  unsubstituted and substituted phenyl, benzyl, ($C_1$–$C_6$-alkyl)-CO, and phenyl-CO, the substituents of which are selected from the group consisting of halogens, pseudohalogens, $C_1$–$C_3$-alkyl, $C_1$–$C_3$-alkoxy, and $CF_3$,
and wherein one or more of these substituents can be present;
$R^{14}$ independently has the same meaning as $R^{13}$;
$R^{15}$ is selected from the group consisting of:
  H;
  $C_1$–$C_{10}$-alkyl;
  ($C_1$–$C_3$-alkoxy)-$C_1$–$C_3$-alkyl;
  and substituted and unsubstituted benzyl, phenyl, the substituents of which are selected from the group consisting of halogens, pseudohalogens, $C_1$–$C_3$-alkyl, $C_1$–$C_3$-alkoxy, and $CF_3$, and wherein one or more of these substituents can be present;
$R^{16}$ is selected from the group consisting of:
  $C_1$–$C_{10}$-alkyl which can be substituted by one or more substituents selected from the group consisting of F, OH, $C_1$–$C_8$-alkoxy, aryloxy, ($C_1$–$C_8$-alkyl)mercapto, ($C_1$–$C_8$-alkyl)amino and di($C_1$–$C_8$-alkyl)amino;
  $CF_3$;
  and substituted and unsubstituted phenyl, the substituents of which are selected from the group consisting of halogens, pseudohalogens, $C_1$–$C_3$-alkyl, $C_1$–$C_3$-alkoxy and $CF_3$, and wherein one or more of these substituents can be present;
$R^{17}$ independently has the same meaning as $R^7$;
$R^{18}$ independently has the same meaning as $R^8$;
$R^{19}$ independently has the same meaning as $R^{16}$;
$R^{20}$ independently has the same meaning as $R^{16}$;
$R^{21}$ independently has the same meaning as $R^6$;
$R^{22}$ independently has the same meaning as $R^7$;
$R^{23}$ independently has the same meaning as $R^8$;
$R^{24}$ independently has the same meaning as $R^7$;
$R^{25}$ independently has the same meaning as $R^8$;
$R^{26}$ independently has the same meaning as $R^{16}$;
$R^{27}$ independently has the same meaning as $R^{16}$;
aryl is phenyl, naphth-1-yl or naphth-2-yl; and
m is 0, 1 or 2.

2. An acylated indanyl amine in any of its stereoisomeric forms or a mixture thereof in any ratio or a pharmaceutically acceptable salt thereof according to claim 1, wherein in the formula (I):
$R^1$ is selected from the group consisting of: H; $C_1$–$C_4$-alkyl; $C_1$–$C_4$-alkoxy; $CF_3$; halogens; pseudohalogens; ($C_1$–$C_4$-alkyl)-S(O)$_m$—; and unsubstituted and at least monosubstituted phenyl, the substituents of which are selected from the group consisting of halogens, pseudohalogens, $C_1$–$C_3$-alkyl, $C_1$–$C_3$-alkoxy and $CF_3$;
$R^2$ and $R^3$ are independently from each other selected from the group consisting of: H; halogens; pseudohalogens; and $C_1$–$C_3$-alkyl;
$R^4$ independently has the same meaning as $R^1$;
A is selected from the group consisting of $CH_2$ and CHOH;
B is selected from the group consisting of $CH_2$ and CH—$CH_3$;
$R^5$ is a benzo[1,3] dioxole group optionally substituted with one or more substituents selected from the group consisting of: halogens; CN; $NH_2$; unsubstituted and at least monosubstituted $C_1$–$C_8$-alkyl, $C_2$–$C_8$-alkenyl, $C_2$–$C_8$-alkynyl, $C_1$–$C_8$-alkoxy, ($C_1$–$C_8$-alkyl)amino, and di($C_1$–$C_8$-alkyl)amino, the substituents of which are selected from the group consisting of F, $C_1$–$C_6$-alkoxy, phenoxy, ($C_1$–$C_6$-alkyl)mercapto, $NH_2$, ($C_1$–$C_6$-alkyl)amino, and di($C_1$–$C_6$-alkyl)amino; $C_3$–$C_5$-alkandiyl; phenyl; phenyl-substituted $C_1$–$C_2$-alkyl; $CF_3$; OH; phenoxy; benzyloxy; ($C_1$–$C_6$-alkyl)COO; S(O)$_m$($C_1$–$C_6$)-alkyl; S(O)$_m$-phenyl; SH; phenylamino; benzylamino; ($C_1$–$C_6$-alkyl)-CONH—; ($C_1$–$C_6$-alkyl)-CON($C_1$–$C_4$-alkyl)-; phenyl-CONH—; phenyl-CON($C_1$–$C_4$-alkyl)-; ($C_1$–$C_6$-alkyl)-CO; phenyl-CO; $CF_3$—CO; —$OCH_2O$—; —$OCF_2O$—; —$OCH_2CH_2O$—, —$CH_2CH_2O$—; COO($C_1$–$C_6$-alkyl); —$CONH_2$; —CONH($C_1$–$C_6$-alkyl); —CON(di($C_1$–$C_6$-alkyl)); CNH($NH_2$); —$SO_2NH_2$; —$SO_2$NH($C_1$–$C_6$-alkyl); —$SO_2$NH(phenyl); —$SO_2$N(di($C_1$–$C_6$-alkyl)); ($C_1$–$C_6$-alkyl)$SO_2$NH—; ($C_1$–$C_6$-alkyl)$SO_2$N($C_1$–$C_6$-alkyl)-; phenyl-$SO_2$NH—; phenyl-$SO_2$N($C_1$–$C_6$-alkyl)-; and phenyl and wherein all phenyl-containing groups, which are optionally present in the said substituents of the benzo[1,3]dioxole group can be substituted by one or more substituents selected from the group consisting of halogens, pseudohalogens, $C_1$–$C_3$-alkyl, OH, $C_1$–$C_3$-alkoxy, and $CF_3$; and
m is 0 or 2.

3. An acylated indanyl amine in any of its stereoisomeric forms or a mixture thereof in any ratio or a pharmaceutically acceptable salt thereof according to claim 1, wherein in the formula (I):
$R^1$ is H, halogen or $C_1$–$C_4$-alkyl;
$R^2$ and $R^3$ are each H;
$R^4$ independently has the same meaning as $R^1$;
A is $CH_2$;
$R^5$ is a benzo[1,3]dioxole group substituted with one or more substituents selected from the group consisting of: halogens; CN; $NH_2$; unsubstituted and at least monosubstituted $C_1$–$C_6$-alkyl, $C_2$–$C_6$-alkenyl, $C_2$–$C_6$-alkynyl, $C_1$–$C_3$-alkoxy, ($C_1$–$C_4$-alkyl)amino, and di($C_1$–$C_4$-alkyl)amino, the substituents of which are selected from the group consisting of F, $C_1$–$C_3$-alkoxy, ($C_1$–$C_3$-alkyl)mercapto, and $NH_2$; $C_3$–$C_5$-alkandiyl; phenyl; phenyl-substituted $C_1$–$C_2$-alkyl; $CF_3$; OH; ($C_1$–$C_4$-alkyl)COO; S(O)$_m$ ($C_1$–$C_4$)-alkyl; ($C_1$–$C_4$-alkyl)-CONH—; ($C_1$–$C_4$-alkyl)-CON($C_1$–$C_4$-alkyl)-; ($C_1$–$C_4$-alkyl)-CO; phenyl-CO; $CF_3$—CO;

—OCH₂O—; —OCF₂O—; —OCH₂CH₂O—; —CH₂CH₂O—; COO(C₁–C₆-alkyl); —CONH₂; —CONH(C₁–C₄-alkyl); —CON(di(C₁–C₄-alkyl)); CNH(NH₂); —SO₂NH₂; —SO₂NH(C₁–C₄-alkyl); —SO₂NH(phenyl); —SO₂N(di(C₁–C₄-alkyl)); (C₁–C₄-alkyl)SO₂NH—; and (C₁–C₄-alkyl)SO₂N (C₁–C₄-alkyl)-; and wherein all phenyl and phenyl-containing groups, which are optionally present in the said substituents of the benzo[1,3] dioxole group can be substituted by one or more substituents selected from the group consisting of halogens, pseudohalogens, C₁–C₃-alkyl, OH, C₁–C₃-alkoxy, and CF₃; and m is 0 or 2.

4. An acylated indanyl amine in any of its stereoisomeric forms or a mixture thereof in any ratio or a pharmaceutically acceptable salt thereof according to claim 1, wherein in the formula (I):

R¹ is H, halogen or C₁–C₄-alkyl;

R² and R³ are each H;

R⁴ independently has the same meaning as R¹;

A and B are each CH₂;

R⁵ is benzo[1,3] dioxole group optionally with one or more substituents selected from the group consisting of: F; Cl; Br; C₁–C₃-alkyl; C₁–C₃-alkoxymethyl; 2-amino-3,3,3-trifluoro-propyl-; CF₃; C₃–C₅-alkandiyl; phenyl; benzyl; OH; C₁–C₃-alkoxy; phenoxy; trifluoromethoxy; 2,2,2-trifluoroethoxy; (C₁–C₄-alkyl) COO; (C₁–C₃-alkyl)mercapto; phenylmercapto; (C₁–C₃-alkyl)sulfonyl; phenylsulfonyl; NH₂; (C₁–C₄-alkyl)amino; di(C₁–C₄-alkyl)amino; (C₁–C₃-alkyl)-CONH—; (C₁–C₃-alkyl)-SO₂NH—; (C₁–C₃-alkyl)-CO; phenyl-CO; —OCH₂O—; —OCF₂O—; —CH₂CH₂O—; COO(C₁–C₄-alkyl); —CONH₂; —CONH(C₁–C₄-alkyl); —CON(di(C₁–C₄-alkyl)); CN; —SO₂NH₂; —SO₂NH(C₁–C₄-alkyl); and —SO₂N(di(C₁–C₄-alkyl)); and wherein all phenyl, phenyl-containing groups which are optionally present in said benzo[1,3] dioxole group can be substituted by one or more substituents selected from the group consisting of halogens, pseudohalogens, C₁–C₃-alkyl, OH, C₁–C₃-alkoxy, and CF₃.

5. An acylated indanyl amine in any of its stereoisomeric forms or a mixture thereof in any ratio or a pharmaceutically acceptable salt thereof according to claim 1, wherein in the formula (I):

R¹ is H, halogen or C₁–C₄-alkyl;

R², R³ and R⁴ are each H;

A and B are each CH₂;

R⁵ is selected from the group consisting of: benzo[1,3] dioxol-5-yl, and 2,2-difluoro-benzo[1,3]dioxol-5-yl.

6. An acylated indanyl amine or a pharmaceutically acceptable salt thereof according to claim 1, which is 2,2-difluoro-benzo[1,3]dioxole-5-carboxylic acid indan-2-ylamide.

7. A pharmaceutical preparation comprising an effective dose of at least one compound of the formula (I) as defined in claim 1 in any of its stereoisomeric forms or a mixture thereof in any ratio and/or a pharmaceutically acceptable salt thereof and a pharmaceutically acceptable carrier.

8. A pharmaceutical preparation according to claim 7, which pharmaceutical preparation is in the form of a pill, tablet, lacquered tablet, sugar-coated tablet, granule, hard or soft gelatin capsule, aqueous, alcoholic or oily solution, syrup, emulsion or suspension, suppository, solution for injection or infusion, ointment, tincture, spray, transdermal therapeutic systems, nasal spray, aerosol mixture, microcapsule, implant or rod.

9. The acylated indanyl amine according to claim 1 selected from the group consisting of benzo[1,3]dioxol-5-carboxylic-acid (5-nitro-indan-2-yl)-amide, benzo[1,3]dioxol-5-carboxylic-acid (6-chlor-1-hydroxy-indan-2-yl)-amide, 2,2-difluoro-benzo[1,3]dioxol-5-carboxylic acid indan-2-ylamide, and benzo[1,3]dioxol-5-carboxylic acid indan 2-yl-amide.

10. The acylated indanyl amine according to claim 9, which is 2,2-difluoro-benzo[1,3]dioxol-5-carboxylic acid indan-2-ylamide.

11. A pharmaceutical preparation comprising an effective dose of at least one compound of claim 9 and a pharmaceutically acceptable carrier.

12. A pharmaceutical preparation according claim 11, which pharmaceutical preparation is in the form of a pill, tablet, lacquered tablet, sugar-coated tablet, granule, hard or soft gelatin capsule, aqueous, alcoholic or oily solution, syrup, emulsion or suspension, suppository, solution for injection or infusion, ointment, tincture, spray, transdermal therapeutic systems, nasal spray, aerosol mixture, microcapsule, implant or rod.

13. A method of treating in a mammal a disease selected from the group consisting of stable or unstable angina pectoris, coronary heart disease, acute coronary syndrome, heart failure, Myocardial infarction, thrombosis, peripheral artery occlusive disease, endothelial dysfunction, atherosclerosis, restenosis, endothelial damage after PTCA, hypertension, and diabetes complications, which method comprises administering to said mammal a physiologically active amount of a compound according to the general formula (I) as defined in claim 1, in any of its stereoisomeric forms or a mixture thereof in any ratio or a pharmaceutically acceptable salt thereof.

14. A method of treating in a mammal a disease selected from the group consisting of stable or unstable angina pectoris, coronary heart disease, acute coronary syndrome, heart failure, myocardial infarction, thrombosis, peripheral artery occlusive disease, endothelial dysfunction, atherosclerosis, restenosis, endothelial damage after PTCA, hypertension, and diabetes complications, which method comprises administering to said mammal a physiologically active amount of a compound according to the general formula (I) as defined in claim 2, in any of its stereoisomeric forms or a mixture thereof in any ratio or a pharmaceutically acceptable salt thereof.

15. A method of treating in a mammal a disease selected from the group consisting of stable or unstable angina pectoris, coronary heart disease, acute coronary syndrome, heart failure, myocardial infarction, thrombosis, peripheral artery occlusive disease, endothelial dysfunction, atherosclerosis, restenosis, endothelial damage after PTCA, hypertension, and diabetes complications, which method comprises administering to said mammal a physiologically active amount of a compound according to the general formula (I) as defined in claim 3, in any of its stereoisomeric or a mixture thereof in any ratio or a pharmaceutically acceptable salt thereof.

16. A method of treating in a mammal a disease selected from a the group consisting of stable or unstable angina pectoris, coronary heart disease, acute coronary syndrome, heart failure, myocardial infarction, thrombosis, peripheral artery occlusive disease, endothelial dysfunction, atherosclerosis, restenosis, endothelial damage after PTCA, hypertension, and diabetes complications, which method comprises administering to said mammal a physiologically active amount of a compound according to the general formula (I) as defined in claim 4, in any of its stereoisomeric forms or a mixture thereof in any ratio or a pharmaceutically acceptable salt thereof.

17. A method of treating in a mammal a disease selected from the group consisting of stable or unstable angina pectoris, coronary heart disease, acute coronary syndrome, heart failure, myocardial infarction, thrombosis, peripheral artery occlusive disease, endothelial dysfunction, atherosclerosis, restenosis, endothelial damage after PTCA, hypertension, and which method comprises administering to said mammal a physiologically active amount of a compound according to the general formula (I) as defined in claim 5, in any of its stereoisomeric forms or a mixture thereof in any ratio or a pharmaceutically acceptable salt thereof.

18. A method of treating in a mammal a disease selected from the group consisting of stable or unstable angina pectoris, coronary heart disease, acute coronary syndrome, heart failure, myocardial infarction, thrombosis, peripheral artery occlusive disease, endothelial dysfunction, atherosclerosis, restenosis, endothelial damage after PTCA, hypertension, and which method comprises administering to said mammal a physiologically active amount of a compound according to the general formula (I) as defined in claim 6, in any of its stereoisomeric forms or a mixture thereof in any ratio or a pharmaceutically acceptable salt thereof.

19. The method according to any one of claims 13–18, wherein the mammal is human.

20. The method according to any one of claims 13–18 wherein the disease is selected from the group consisting of unstable angina pectoris, acute coronary syndrome, heart failure, thrombosis, peripheral artery occlusive disease, restenosis, and endothelial damage after PTCA.

21. The method according to any one of claims 13–18 wherein the disease is selected from the group consisting of stable angina pectoris, coronary heart disease, myocardial infarction, endothelial dysfunction, atherosclerosis, and diabetes complications.

22. The method of claim 21 wherein the disease is coronary heart disease.

23. The method of claim 20 wherein the disease is heart failure.

24. The method of claim 21 wherein the disease is atherosclerosis.

25. The method of claim 20 wherein the disease is peripheral artery occlusive disease.

26. A method of treating in a mammal a disease selected from the group consisting of stable or unstable angina pectoris, coronary heart disease, acute coronary syndrome, heart failure, myocardial infarction, thrombosis, peripheral artery occlusive disease, endothelial dysfunction, atherosclerosis, restenosis, endothelial damage after PTCA, hypertension, and diabetes complications, which method comprises administering to said mammal a physiologically active amount of a compound according to the general formula (I) as defined in claim 9.

27. A method of treating in a mammal a disease selected from the group consisting of stable unstable angina pectoris, coronary heart disease, acute coronary syndrome, heart failure, myocardial infarction, thrombosis, peripheral artery occlusive disease, endothelial dysfunction, atherosclerosis, restenosis, endothelial damage after PTCA, hypertension, and diabetes complications, which method comprises administering to said mammal a physiologically active amount of a compound according to the general formula (I) as defined in claim 10.

28. The method according to any one of claims 26 and 27, wherein the mammal is a human.

29. The method according to any one of claims 26 and 27, wherein the disease is selected from the group consisting of unstable angina pectoris, acute coronary syndrome, heart failure, thrombosis, peripheral artery occlusive disease, restenosis, and endothelial damage after PTCA.

30. The method according to any one of claims 26 and 27, wherein the disease is selected from the group consisting of stable angina pectoris, coronary heart disease, myocardial infarction, endothelial dysfunction, atherosclerosis, and diabetes complications.

31. The method of claim 30 wherein the disease is coronary heart disease.

32. The method of claim 29 wherein the disease is heart failure.

33. The method of claim 30 wherein the disease is atherosclerosis.

34. The method of claim 29 wherein the disease is peripheral artery occlusive disease.

\* \* \* \* \*

UNITED STATES PATENT AND TRADEMARK OFFICE
CERTIFICATE OF CORRECTION

PATENT NO. : 7,179,839 B2
APPLICATION NO. : 10/073160
DATED : February 20, 2007
INVENTOR(S) : Hartmut Strobel et al.

It is certified that error appears in the above-identified patent and that said Letters Patent is hereby corrected as shown below:

Title Page, Item (74), in column 2, in "Attorney, Agent, or Firm" line 1, delete "Ronald G. Ort" and insert -- Joseph D. Rossi; Robert J. Kajubi and Ronald G. Ort --, therefor.

In column 4, line 54, after "$R^7$;" insert -- $R^{25}$ independently has the same meaning as $R^8$; --.

In column 4, line 55, delete "$R^8$;" and insert -- $R^{16}$; --, therefor.

In column 12, line 50, delete "faryl," and insert -- furyl, --, therefor.

In column 13, line 67, delete "—$OCF_2$—;" and insert -- —$OCF_2O$—; --, therefor.

In column 14, line 6, delete "$C_3$-$C_3$-alkyl," and insert -- $C_1$-$C_3$-alkyl, --, therefor.

In column 19, line 42, delete "$C_{10}$-$C_3$-alkyl," and insert -- $C_1$-$C_3$-alkyl, --, therefor.

In column 65, line 62-63, delete
"4-FLUORO-N-(5-(2-METHANSULFONYLAMINO)-INDAN-2-YL) BENZAMIDE" and insert
-- 4-FLUORO-N-(5-(2-METHYLPROPIONYLAMINO)-INDAN-2-YL) BENZAMIDE --, therefor.

In column 81, line 41, in claim 1, after "$R^3$" insert -- are --.

In column 82, line 52, in claim 1, before "phenyl-" insert -- and --.

In column 83, line 4, in claim 1, after "phenyl;" insert -- and --.

In column 83, line 15-16, in claim 1, delete "phenyl and heteroaryl," and insert -- phenyl, --, therefor.

In column 83, line 38, in claim 1, delete "phenyl," and insert -- and phenyl, --, therefor.

Signed and Sealed this
Sixteenth Day of October, 2012

David J. Kappos
*Director of the United States Patent and Trademark Office*

CERTIFICATE OF CORRECTION (continued)

U.S. Pat. No. 7,179,839 B2

In column 84, line 40, in claim 2, before "phenyl-$SO_2$N" insert -- and --.

In column 84, line 41, in claim 2, delete "and phenyl and wherein all" and insert -- and wherein all phenyl and --, therefor.

In column 84, line 56, in claim 3, below "A is $CH_2$;" insert -- B is $CH_2$; --.

In column 84, line 56, in claim 3, after "group" insert -- optionally --.

In column 85, line 22, in claim 4, after "optionally" insert -- substituted --.

In column 85, line 36, in claim 4, delete "phenyl," and insert -- phenyl and --, therefor.

In column 86, line 56, in claim 15, after "stereoisomeric" insert -- forms --.

In column 86, line 60, in claim 16, after "from" delete "a".

In column 87, line 10, in claim 17, after "and" insert -- diabetes complications, --.

In column 87, line 13, in claim 27, after "stable" insert -- or --.

In column 87, line 21, in claim 18, after "and" insert -- diabetes complications, --.

In column 87, line 27, in claim 19, after "is" insert -- a --.